(12) United States Patent
Haseba et al.

(10) Patent No.: US 8,475,887 B2
(45) Date of Patent: *Jul. 2, 2013

(54) OPTICALLY ISOTROPIC LIQUID CRYSTAL MEDIUM, AND OPTICAL DEVICE

(75) Inventors: Yasuhiro Haseba, Chiba (JP); Kohki Sago, Chiba (JP); Takafumi Kuninobu, Chiba (JP)

(73) Assignees: JNC Corporation, Tokyo (JP); JNC Petrochemical Corporation, Tokyo (JP)

(*) Notice: Subject to any disclaimer, the term of this patent is extended or adjusted under 35 U.S.C. 154(b) by 173 days.

This patent is subject to a terminal disclaimer.

(21) Appl. No.: 12/992,674

(22) PCT Filed: May 8, 2009

(86) PCT No.: PCT/JP2009/058680
§ 371 (c)(1),
(2), (4) Date: Nov. 15, 2010

(87) PCT Pub. No.: WO2009/139330
PCT Pub. Date: Nov. 19, 2009

(65) Prior Publication Data
US 2011/0069245 A1    Mar. 24, 2011

(30) Foreign Application Priority Data
May 15, 2008 (JP) .................. 2008-128359

(51) Int. Cl.
| | |
|---|---|
| C09K 19/34 | (2006.01) |
| C09K 19/12 | (2006.01) |
| C09K 19/32 | (2006.01) |
| C09K 19/30 | (2006.01) |
| C09K 19/20 | (2006.01) |
| C09K 19/38 | (2006.01) |
| C09K 19/54 | (2006.01) |
| G02F 1/133 | (2006.01) |

(52) U.S. Cl.
USPC ........... 428/1.1; 252/299.01; 252/299.61; 252/299.62; 252/299.63; 252/299.66; 252/299.67; 252/299.5

(58) Field of Classification Search
USPC .......... 428/1.1; 252/299.01, 299.61, 299.62, 252/299.63, 299.66, 299.67, 299.5
See application file for complete search history.

(56) References Cited

U.S. PATENT DOCUMENTS

| | | | | |
|---|---|---|---|---|
| 7,722,783 | B2* | 5/2010 | Haseba et al. | 252/299.01 |
| 7,976,913 | B2* | 7/2011 | Hiraoka et al. | 428/1.1 |
| 8,012,369 | B2* | 9/2011 | Saito et al. | 252/299.6 |
| 8,071,182 | B2* | 12/2011 | Yanai et al. | 428/1.1 |
| 8,147,929 | B2* | 4/2012 | Saito | 428/1.1 |
| 8,221,854 | B2* | 7/2012 | Czanta et al. | 428/1.1 |
| 2006/0006363 | A1 | 1/2006 | Heckmeier et al. | |
| 2006/0050354 | A1 | 3/2006 | Heckmeier et al. | |
| 2009/0135368 | A1* | 5/2009 | Haseba et al. | 349/183 |
| 2010/0127213 | A1* | 5/2010 | Czanta et al. | 252/299.61 |
| 2011/0193022 | A1* | 8/2011 | Tanaka et al. | 252/299.61 |
| 2011/0242473 | A1* | 10/2011 | Haseba et al. | 349/139 |
| 2011/0315925 | A1* | 12/2011 | Hiraoka et al. | 252/299.61 |

FOREIGN PATENT DOCUMENTS

| | | |
|---|---|---|
| DE | 102008016053 A1 * | 10/2008 |
| EP | 1690917 | 8/2006 |
| JP | 2000-327632 | 11/2000 |
| JP | 2003-327966 | 11/2003 |
| JP | 2004-059772 | 2/2004 |
| JP | 2004-182949 | 7/2004 |
| JP | 2005-157109 | 6/2005 |
| JP | 2005-336477 | 12/2005 |
| JP | 2006-089622 | 4/2006 |
| JP | 2006-127707 | 5/2006 |
| JP | 2006-299084 | 11/2006 |
| WO | 2005-080529 | 9/2005 |
| WO | 2005-090520 | 9/2005 |
| WO | 2006-063662 | 6/2006 |
| WO | WO 2008102641 A1 * | 8/2008 |

OTHER PUBLICATIONS

Kikuchi et al, "Polymer-Stabilized Liquid Crystal Blue Phases", in Nature Materials, vol. 1, Sep. 2, 2002, pp. 64-68.
Hisakado et al, "Large Electro-Optic Kerr Effect in Polymer-Stabilized Liquid-Crystalline Blue Phases", in Advanced Materials, vol. 17, Jan. 6, 2005, pp. 96-98.
Haseba et al., "Electro-Optic Effects of the Optically Isotropic State Induced by the Incorporative Effects of a Polymer Network and the Chirality of Liquid Crystal" in Journal of the SID, vol. 14/6, Sep. 22, 2006, pp. 551-556.

* cited by examiner

Primary Examiner — Shean C Wu
(74) Attorney, Agent, or Firm — J.C. Patents

(57) ABSTRACT

A liquid crystal medium having a wide temperature range of a liquid crystal phase, a large optical anisotropy, and a large dielectric anisotropy and having an optically isotropic liquid crystal phase is provided. The liquid crystal medium is characterized by containing a liquid crystal compound having a pyrimidine ring and a linking group —$CF_2O$— and a chiral dopant, and exhibiting an optically isotropic liquid crystal phase.

42 Claims, 1 Drawing Sheet

OPTICALLY ISOTROPIC LIQUID CRYSTAL MEDIUM, AND OPTICAL DEVICE

BACKGROUND OF THE INVENTION

1. Field of the Invention

The present invention generally relates to a liquid crystal medium useful as a material for an optical device, in particular, to a liquid crystal medium having a wide temperature range of a liquid crystal phase, a large dielectric anisotropy, and an optical anisotropy. Additionally, the present invention further relates to an optical device using the liquid crystal medium, and in particular, to an optical device that can be used in a wide temperature range and driven at a low voltage, and is capable of achieving a high-speed electro-optical response.

2. Description of Related Art

Liquid crystal display (LCD) devices utilizing liquid crystal compositions are widely used in displays of clocks, calculators, word processors, and the like. These LCD devices utilize optical anisotropy, dielectric anisotropy and the like of liquid crystal compounds. The operation modes of the LCD devices are known to mainly include phase change (PC), twisted nematic (TN), super twisted nematic (STN), bistable twisted nematic (BTN), electrically controlled birefringence (ECB), optically compensated bend (OCB), in-plane switching (IPS), and vertical alignment (VA) and the like, which utilize one or more polarizers for display. Moreover, in recent years, more attentions have been paid to the mode where an electric field is applied to an optically isotropic liquid crystal phase to enable the liquid crystal phase to exhibit electrically controlled birefringence (Patent References 1-9, and Non-patent References 1-3).

Moreover, wavelength variable filters, wavefront control elements, liquid-crystal lenses, aberration correction elements, aperture control elements, and optical head apparatuses and the like utilizing the electrically controlled birefringence in a blue phase which is one of the optically isotropic liquid crystal phases have been proposed (Patent References 10-12).

According to the driving mode, the devices are classified into passive matrix (PM) and active matrix (AM) types. The PM type is further classified into static type and multiplex type, and the AM type is further classified into thin film transistor (TFT) type and metal-insulator-metal (MIM) type.

Such LCD devices contain a liquid crystal composition having suitable physical properties. In order to improve the characteristics of an LCD device, it is preferred that the liquid crystal composition has suitable physical properties. A liquid crystal compound as a component of the liquid crystal composition needs to have the following general properties:

(1) stable chemical properties and stable physical properties;

(2) a high clearing point (i.e., liquid crystal phase-isotropic phase transition temperature);

(3) a low lower-limit temperature of a liquid crystal phase (i.e., nematic phase, cholesteric phase, smectic phase, and optically isotropic liquid crystal phase such as blue phase);

(4) excellent compatibility with other liquid crystal compounds;

(5) a suitable dielectric anisotropy; and (6) a suitable optical anisotropy.

Particularly, for an optically isotropic liquid crystal phase, a liquid crystal compound having a large dielectric anisotropy and a large optical anisotropy is preferred, in view of lowering the driving voltage.

When a liquid crystal composition containing a liquid crystal compound having stable chemical and physical properties as described in (1) is used in an LCD device, the voltage holding ratio is improved.

Further, a liquid crystal composition containing a liquid crystal compound having a high clearing point or a low lower-limit temperature of a liquid crystal phase as described in (2) and (3), may have an expanded temperature range of a nematic phase or an optically isotropic liquid crystal phase, thus being used in display devices in a wider temperature range. A single liquid crystal compound exhibits properties which are difficult to function, thus it is generally used in mixture with a number of other liquid crystal compounds to prepare a liquid crystal composition. Therefore, a liquid crystal compound having good compatibility with other liquid crystal compounds as described in (4) is preferably used in LCD devices. In recent years, LCD devices with superior display performance, such as, contrast, display capacity, and response time, are especially required in the industry. In addition, as for the liquid crystal material used, a liquid crystal composition having a low driving voltage is required. Furthermore, in order to drive optical devices driven in an optically isotropic liquid crystal phase with a low voltage, a liquid crystal compound with a large dielectric anisotropy and a large optical anisotropy is preferred.

As for the optically isotropic polymer/liquid crystal composite materials disclosed in Patent References 1-3 and Non-patent References 1-3, the voltages needed for operation of the devices are high. Although optically isotropic liquid crystal compositions and polymer/liquid crystal composite materials expected to have an operation voltage lower than the voltages described above are disclosed in Patent References 4-9, an optically isotropic liquid crystal composition and a polymer/liquid crystal composite material containing a compound having a pyrimidine ring and a linking group —$CF_2O$— of the present application have not been reported.

REFERENCES IN PRIOR ART

Patent References

[Patent Reference 1] Japanese Patent Publication No. 2003-327966
[Patent Reference 2] International Publication No. 2005/90520 pamphlet
[Patent Reference 3] Japanese Patent Publication No. 2005-336477
[Patent Reference 4] Japanese Patent Publication No. 2006-89622
[Patent Reference 5] Japanese Patent Publication No. 2006-299084
[Patent Reference 6] Japanese Patent Publication No. 2006-506477
[Patent Reference 7] Japanese Patent Publication No. 2006-506515
[Patent Reference 8] International Publication No. 2006/063662 pamphlet
[Patent Reference 9] Japanese Patent Publication No. 2006-225655
[Patent Reference 10] Japanese Patent Publication No. 2005-157109
[Patent Reference 11] International Publication No. 2005/80529 pamphlet
[Patent Reference 12] Japanese Patent Publication No. 2006-127707

Non-Patent References

[Non-patent Reference 1] Nature Materials, 1, 64, (2002)
[Non-patent Reference 2] Adv. Mater., 17, 96, (2005)
[Non-patent Reference 3] Journal of the SID, 14, 551, (2006)

SUMMARY OF THE INVENTION

Issues to be Solved by the Present Invention

The present invention is directed to a liquid crystal medium, which is stable to heat and light, and has a wide temperature range of a liquid crystal phase, a large optical anisotropy, a large dielectric anisotropy, and also an optically isotropic liquid crystal phase. The present invention is further directed to various optical devices containing the liquid crystal medium, which can be used in a wide temperature range, and have a short response time, a high contrast, and a low driving voltage.

Means for Solving the Issues

The present invention provides a liquid crystal medium (liquid crystal composition or polymer/liquid crystal composite) and an optical device containing the liquid crystal medium.

[1] A liquid crystal composition, containing a compound of Formula (1) and a chiral dopant, and exhibiting an optically isotropic liquid crystal phase:

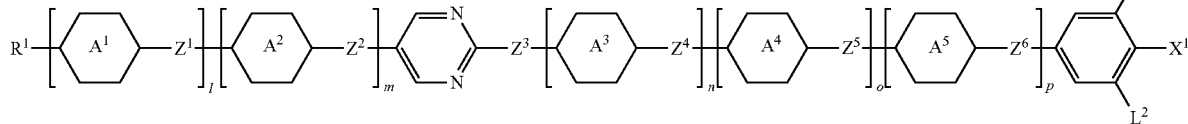
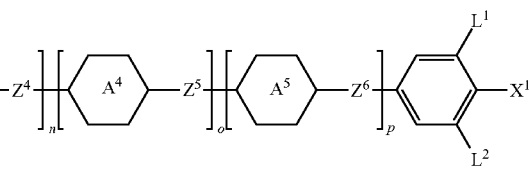

(1)

(in Formula (1), $R^1$ is hydrogen or a $C_{1-20}$ alkyl, in which arbitrary —$CH_2$— in the alkyl may be replaced by —O—, —S—, —COO—, —OCO—, —CH=CH—, —CF=CF—, or —C≡C—, and arbitrary hydrogen in the alkyl and the alkyl with arbitrary —$CH_2$— replaced by —O—, —S—, —COO—, —OCO—, —CH=CH—, —CF=CF—, or —C≡C— may be replaced by halogen or a $C_{1-3}$ alkyl; rings $A^1$, $A^2$, $A^3$, $A^4$, and $A^5$ are independently a benzene ring, naphthalene ring, thiophene ring, piperidine ring, cyclohexene ring, bicyclo-octane ring, tetrahydronaphthalene ring, or a cyclohexane ring, in which arbitrary hydrogen in the rings may be replaced by halogen, a $C_{1-3}$ alkyl, a $C_{1-3}$ alkoxy, or a $C_{1-3}$ haloalkyl, —$CH_2$— in the rings may be replaced by —O— or —S—, —CH= may be replaced by —N=; $Z^1$, $Z^2$, $Z^3$, $Z^4$, $Z^5$, and $Z^6$ are independently a single bond or a $C_{1-4}$ alkylene, in which arbitrary —$CH_2$— in the alkylene may be replaced by —O—, —S—, —COO—, —OCO—, —CSO—, —OCS—, —CH=CH—, —CF=CF—, or —C≡C— and arbitrary hydrogen in the alkylene and the alkylene with arbitrary —$CH_2$— replaced by —O—, —S—, —COO—, —OCO—, —CSO—, —OCS—, —CH=CH—, —CF=CF—, or —C≡C— may be replaced by halogen, provided that at least one of $Z^1$, $Z^2$, $Z^3$, $Z^4$, $Z^5$, and $Z^6$ is —$CF_2$O—; $L^1$ and $L^2$ are independently hydrogen or halogen; $X^1$ is hydrogen, halogen, —C≡N, —N=C=S, —C≡C—C≡N, —$SF_5$, or a $C_{1-10}$ alkyl, in which arbitrary —$CH_2$— in the alkyl may be replaced by —O—, —S—, —CH=CH—, or —C≡C—, and arbitrary hydrogen in the alkyl and the alkyl with arbitrary —$CH_2$— replaced by —O—, —S—, —CH=CH—, or —C≡C— may be replaced by halogen; and l, m, n, o, and p are independently 0 or 1, and l+m+n+o+p≦4).

[2] The liquid crystal composition according to item [1], in which in Formula (1), $R^1$ is a $C_{1-20}$ alkyl, a $C_{2-21}$ alkenyl, a $C_{2-21}$ alkynyl, a $C_{1-19}$ alkoxy, a $C_{2-20}$ alkenyloxy, a $C_{1-19}$ alkylthio, a $C_{1-19}$ alkenylthio, or —$(CH_2)_v$—CH=$CF_2$, where v is 0 or an integer of 1-19; $X^1$ is hydrogen, halogen, —C≡N, —N=C=S, —$SF_5$, —$CH_2$F, —$CHF_2$, —$CF_3$, —$(CH_2)_2$—F, —$CF_2CH_2$F, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F, —$(CF_2)_5$—F, —$OCH_2$F, —$OCHF_2$, —$OCF_3$, —O—$(CH_2)_2$—F, —$OCF_2CH_2$F, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —O$(CH_2)_4$—F, —O—$(CF_2)_4$—F, —O—$(CH_2)_5$—F, —O—$(CF_2)_5$—F, —CH=CHF, —CH=$CF_2$, —CF=CHF, —CH=$CHCH_2$F, —CH=$CHCF_3$, —$(CH_2)_2$—CH=$CF_2$, —$CH_2$CH=$CHCF_3$, or —CH=$CHCF_2CF_3$.

[3] The liquid crystal composition according to item [1] or [2], in which in Formula (1), $Z^1$, $Z^2$, $Z^3$, $Z^4$, $Z^5$, and $Z^6$ are independently a single bond, —$CH_2CH_2$—, —CH=CH—, —COO—, —$CF_2$O—, —$CH_2$O—, or —$OCH_2$—.

[4] The liquid crystal composition according to any one of items [1] to [3], in which the rings $A^1$, $A^2$, $A^3$, $A^4$, and $A^5$ are independently one of the groups of Formulas (RG-1)-(RG-15), $Y^1$, $Y^2$, $Y^3$, and $Y^4$ are independently hydrogen or halogen, and fn1, fn2, fn3, and fn4 are independently 0, 1, 2, or 3:

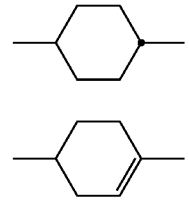
(RG-1)

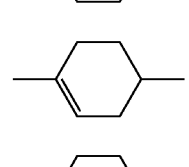
(RG-2)

(RG-3)

(RG-4)

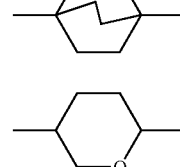
(RG-5)

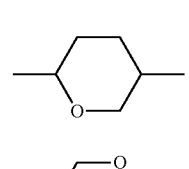
(RG-6)

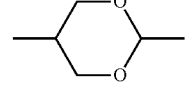
(RG-7)

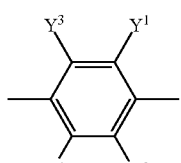 (RG-8)
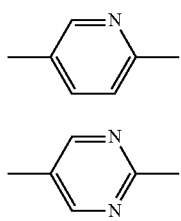 (RG-9)
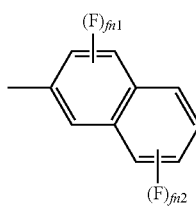 (RG-10)
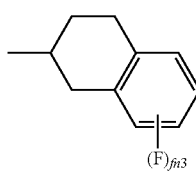 (RG-11)
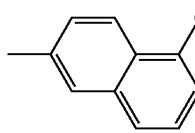 (RG-12)
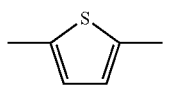 (RG-13)
 (RG-14)
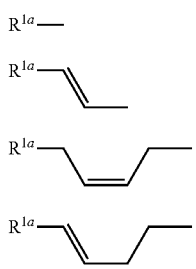 (RG-15)
[5] The liquid crystal composition according to any one of items [1] to [4], in which $R^1$ is any one of the groups of Formulas (CHN-1)-(CHN-19), and $R^{1a}$ is hydrogen or a $C_{1-20}$ alkyl:
$R^{1a}$— (CHN-1)
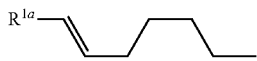 (CHN-2)
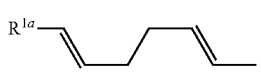 (CHN-3)
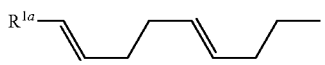 (CHN-4)
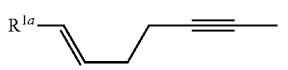 (CHN-5)
 (CHN-6)
(CHN-7)
 (CHN-8)
(CHN-9)
(CHN-10)
$R^{1a}$•O— (CHN-11)
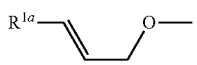 (CHN-12)
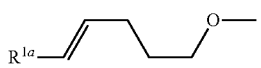 (CHN-13)
$R^{1a}$•S— (CHN-14)
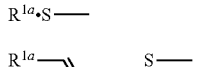 (CHN-15)
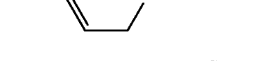 (CHN-16)
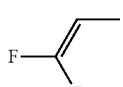 (CHN-17)
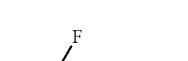 (CHN-18)
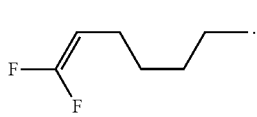 (CHN-19)

[6] The liquid crystal composition according to item [1], containing at least one compound selected from the group consisting of compounds of Formulas (1-1)-(1-8):
in which $R^1$ is any one of the groups of Formulas (CHN-1)-(CHN-19), $R^{1a}$ is hydrogen or a $C_{1-20}$ alkyl; rings $A^1$, $A^2$, $A^3$, $A^4$, and $A^5$ are independently a group of Formula (RG-1),
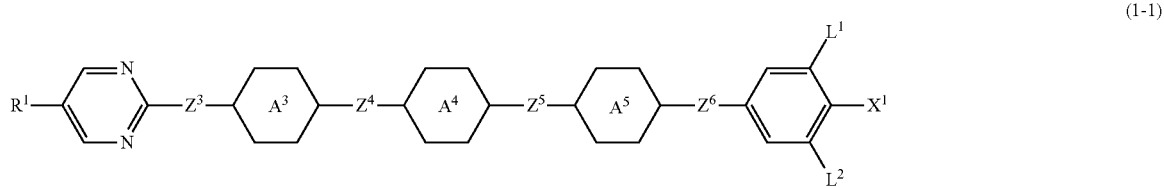
(1-1)
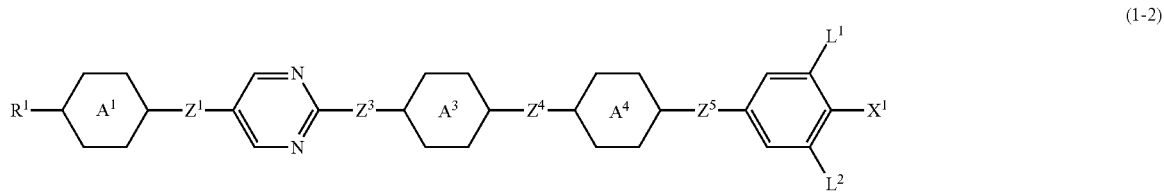
(1-2)
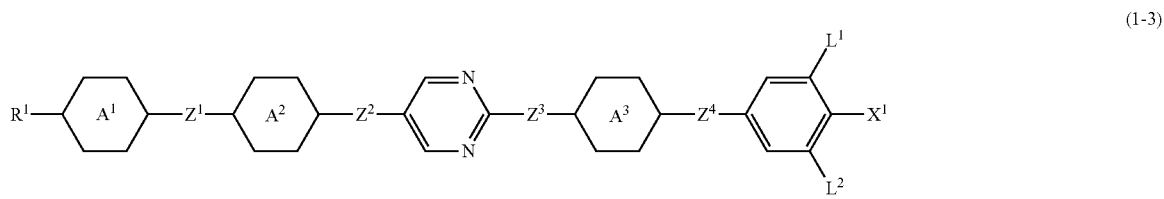
(1-3)
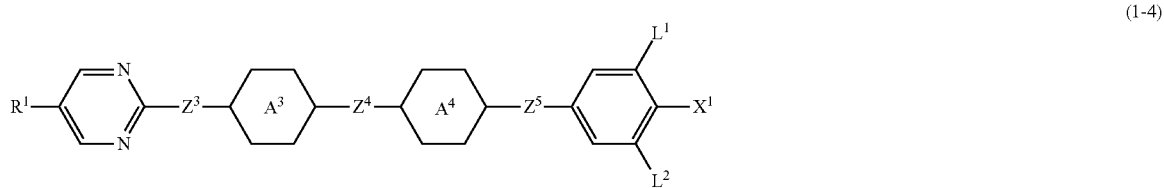
(1-4)
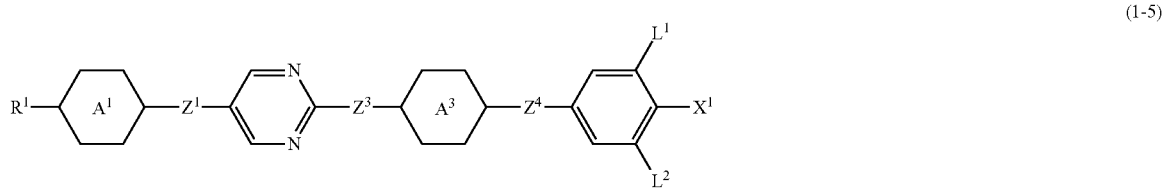
(1-5)
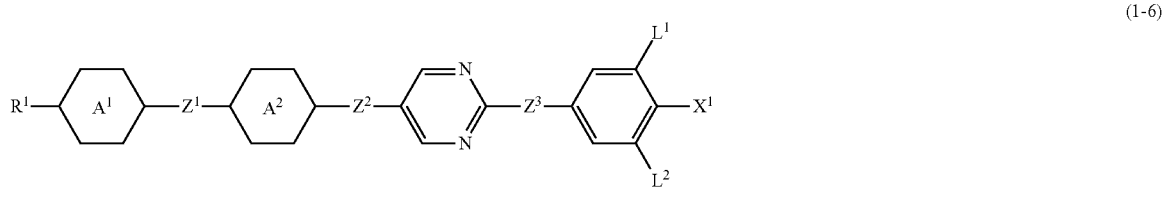
(1-6)
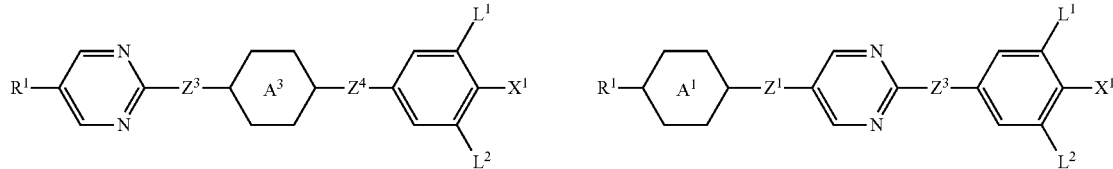
(1-7) (1-8)

(RG-5), (RG-7), (RG-8-1)-(RG-8-5), (RG-9), (RG-10), (RG-11-1), (RG-13), or (RG-15); $Z^1$, $Z^2$, $Z^3$, $Z^4$, $Z^5$, and $Z^6$ are independently a single bond, —CH$_2$CH$_2$—, —CH=CH—, —C≡C—, —COO—, —CF$_2$O—, —CH$_2$O—, or —OCH$_2$—; $L^1$ and $L^2$ are independently hydrogen, fluorine, or chlorine; $X^1$ is fluorine, chlorine, —C≡N, —CF$_3$, —CHF$_2$, —CH$_2$F, —OCF$_3$, —OCHF$_2$, —OCH$_2$F, or —C≡C—CF$_3$:
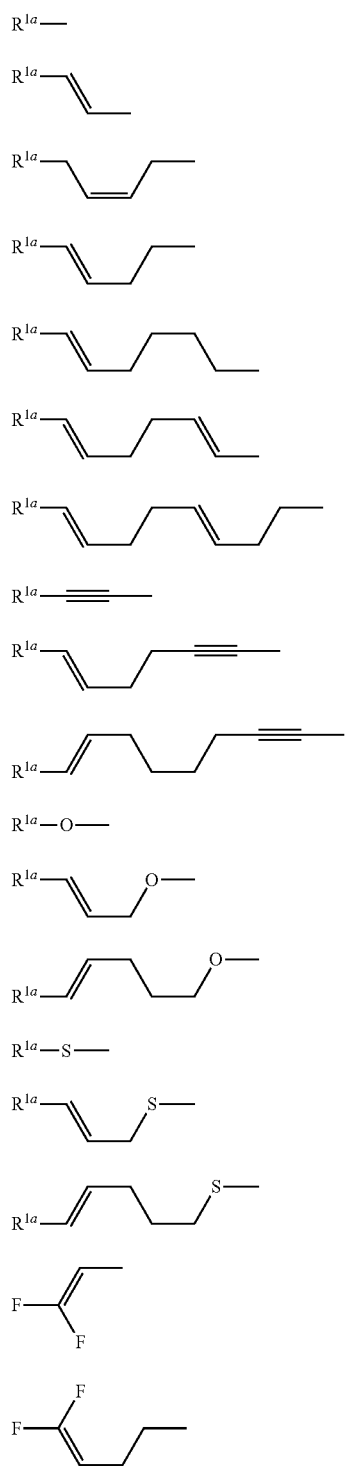
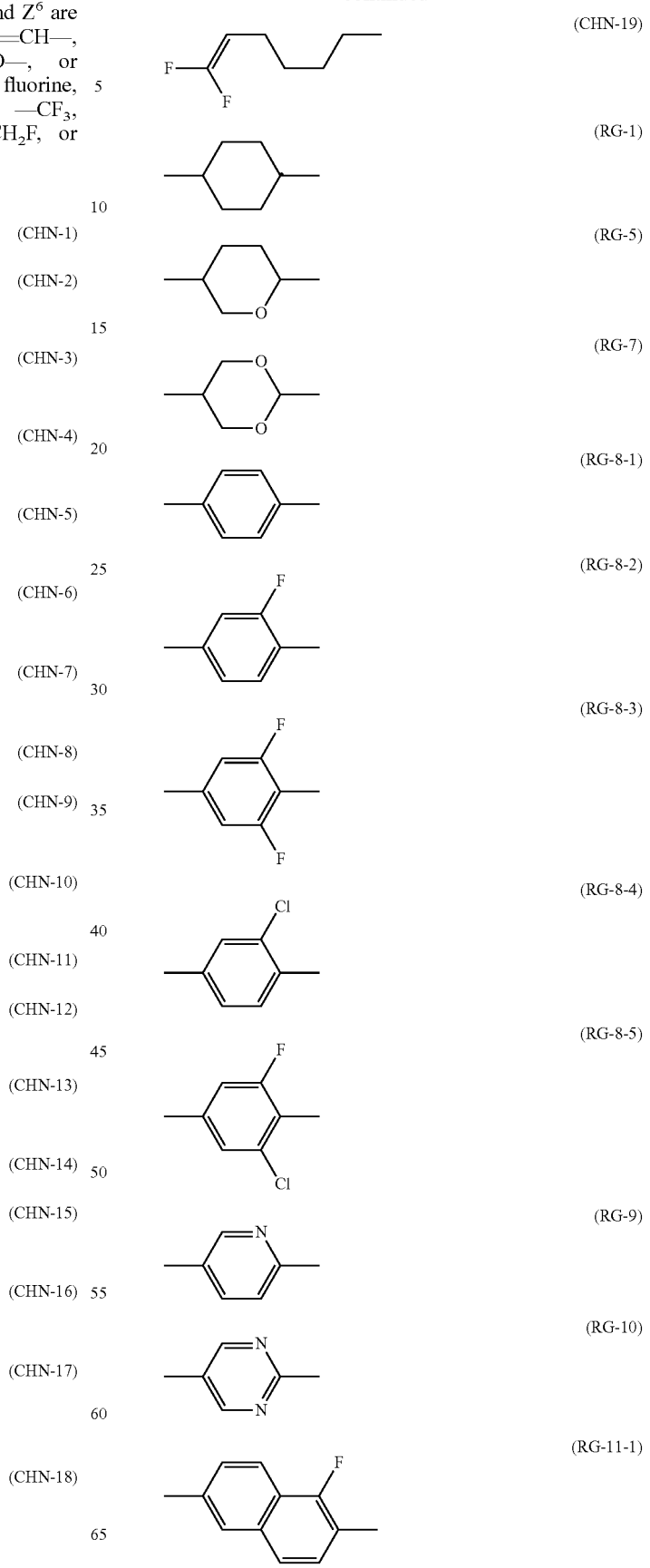

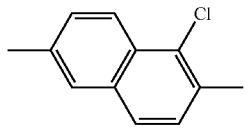
(RG-13)

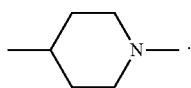
(RG-15)

[7] The liquid crystal composition according to item [6], in which in Formulas (1-1)-(1-8), $Z^3$ is a single bond.

[8] The liquid crystal composition according to item [7], in which in Formulas (1-1)-(1-8), at least one of $Z^1$, $Z^2$, $Z^3$, $Z^4$, $Z^5$, and $Z^6$ is —CF$_2$O—, and the others are a single bond.

[9] The liquid crystal composition according to any one of items [6] to [8], in which in Formulas (1-1)-(1-9), $R^1$ is any one of the groups of Formulas (CHN-1), (CHN-2), (CHN-4), and (CHN-6)-(CHN-8), and $R^{1a}$ is hydrogen or a $C_{1-20}$ alkyl:

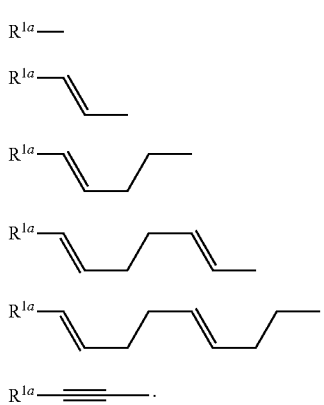

(CHN-1)
(CHN-2)
(CHN-4)
(CHN-6)
(CHN-7)
(CHN-8)

[10] The liquid crystal composition according to any one of items [1] to [9], further containing at least one compound selected from the group consisting of compounds of Formulas (2), (3), and (4):

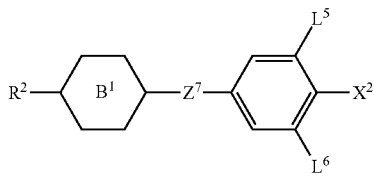
(2)

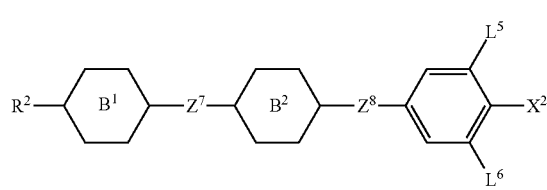
(3)

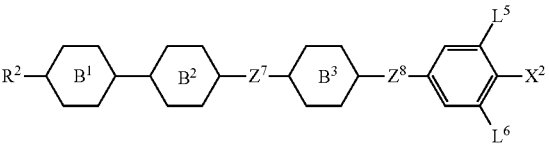
(4)

in which $R^2$ is a $C_{1-10}$ alkyl or a $C_{2-10}$ alkenyl, in which arbitrary —CH$_2$— in the alkyl and the alkenyl may be replaced by —O—, and arbitrary hydrogen in the alkyl, the alkenyl, or the alkyl and the alkenyl with arbitrary —CH$_2$— replaced by —O— may be replaced by fluorine; $X^2$ is fluorine, chlorine, —OCF$_3$, —OCHF$_2$, —CF$_3$, —CHF$_2$, —CH$_2$F, —OCF$_2$CHF$_2$, or —OCF$_2$CHFCF$_3$; rings $B^1$, $B^2$, and $B^3$ are independently 1,4-cyclohexylene, 1,3-dioxane-2,5-diyl, pyrimidine-2,5-diyl, tetrahydropyrane-2,5-diyl, 1,4-phenylene, naphthalene-2,6-diyl, 1,4-phenylene with arbitrary hydrogen replaced by fluorine, or naphthalene-2,6-diyl with arbitrary hydrogen replaced by fluorine or chlorine; $Z^7$ and $Z^8$ are independently —(CH$_2$)$_2$—, —(CH$_2$)$_4$—, —COO—, —CF$_2$O—, —OCF$_2$—, —CH=CH—, —C≡C—, —CH$_2$O—, or a single bond, in which when at least one of the rings $B^1$-$B^3$ is pyrimidine-2,5-diyl, each of $Z^7$ and $Z^8$ is not —CF$_2$O—; and $L^5$ and $L^6$ are independently hydrogen or fluorine.

[11] The liquid crystal composition according to any one of items [1] to [9], further containing at least one compound selected from the group consisting of compounds of Formula (5):

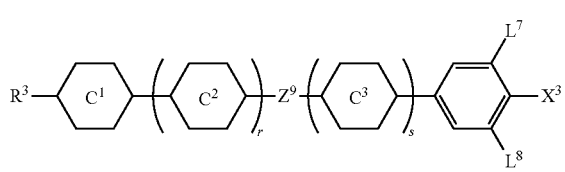
(5)

in which $R^3$ is a $C_{1-10}$ alkyl or a $C_{2-10}$ alkenyl, in which arbitrary —CH$_2$— in the alkyl and the alkenyl may be replaced by —O—, and arbitrary hydrogen in the alkyl, the alkenyl, or the alkyl and the alkenyl with arbitrary —CH$_2$— replaced by —O— may be replaced by fluorine; $X^3$ is —C≡N or —C≡C—C≡N; rings $C^1$, $C^2$ and $C^3$ are independently 1,4-cyclohexylene, 1,4-phenylene, 1,4-phenylene with arbitrary hydrogen replaced by fluorine, naphthalene-2,6-diyl, naphthalene-2,6-diyl with arbitrary hydrogen replaced by fluorine or chlorine, 1,3-dioxane-2,5-diyl, tetrahydropyrane-2,5-diyl, or pyrimidine-2,5-diyl; $Z^9$ is —(CH$_2$)$_2$—, —COO—, —CF$_2$O—, —OCF$_2$—, —C≡C—, —CH$_2$O—, or a single bond, in which when at least one of the rings $C^1$-$C^3$ is pyrimidine-2,5-diyl, $Z^9$ is not —CF$_2$O—; $L^7$ and $L^8$ are independently hydrogen or fluorine; and r is 1 or 2, s is 0 or 1, and r+s=0, 1, or 2.

[12] The liquid crystal composition according to any one of items [1] to [9], further containing at least one compound selected from the group consisting of compounds of Formulas (6), (7), (8), (9), and (10):

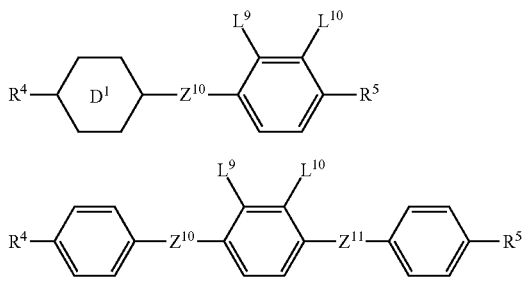

(6)

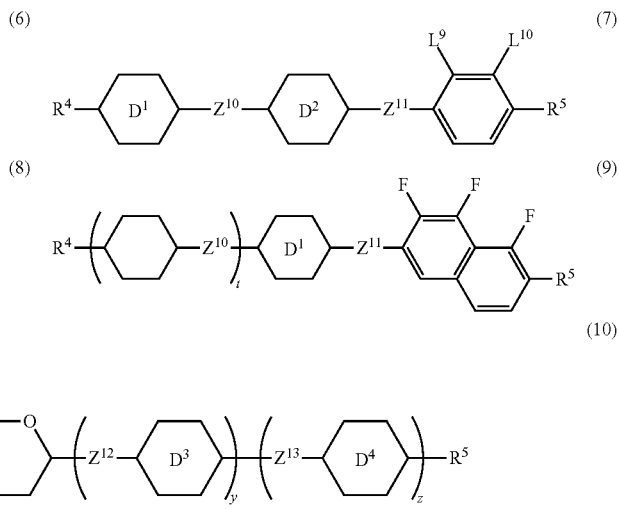

(7)

(8)

(9)

(10)

in which $R^4$ and $R^5$ are independently a $C_{1-10}$ alkyl or a $C_{2-10}$ alkenyl, in which arbitrary —$CH_2$— in the alkyl and the alkenyl may be replaced by —O—, and arbitrary hydrogen in the alkyl, the alkenyl, or the alkyl and the alkenyl with arbitrary —$CH_2$-replaced by —O— may be replaced by fluorine; rings $D^1$, $D^2$, $D^3$, and $D^4$ are independently 1,4-cyclohexylene, 1,4-cyclohexenylene, 1,4-phenylene, 1,4-phenylene with arbitrary hydrogen replaced by fluorine, tetrahydropyrane-2,5-diyl, or decalin-2,6-diyl; $Z^{10}$, $Z^{11}$, $Z^{12}$, and $Z^{13}$ are independently —$(CH_2)_2$—, —COO—, —$CH_2O$—, —$OCF_2$—, —$OCF_2(CH_2)_2$—, or a single bond; $L^9$ and $L^{10}$ are independently fluorine or chlorine; and t, u, x, y, and z are independently 0 or 1, and u+x+y+z is 1 or 2.

[13] The liquid crystal composition according to any one of items [1] to [9], further containing at least one compound selected from the group consisting of compounds of Formulas (11), (12), and (13):

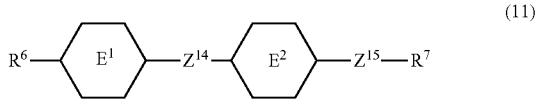

(11)

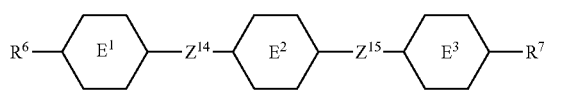

(12)

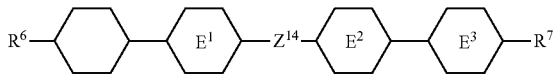

(13)

in which $R^6$ and $R^7$ are independently a $C_1$-10 alkyl or a $C_2$-10 alkenyl, in which arbitrary —$CH_2$— in the alkyl and the alkenyl may be replaced by —O—, and arbitrary hydrogen in the alkyl, the alkenyl, or the alkyl and the alkenyl with arbitrary —$CH_2$-replaced by —O— may be replaced by fluorine; rings $E^1$, $E^2$, and $E^3$ are independently 1,4-cyclohexylene, pyrimidine-2,5-diyl, 1,4-phenylene, 2-fluoro-1,4-phenylene, 3-fluoro-1,4-phenylene, or 2,5-difluoro-1,4-phenylene; $Z^{14}$ and $Z^{15}$ are independently —COO—, —$(CH_2)_2$—, —CH=CH—, or a single bond, in which when at least one of the rings $E^1$-$E^3$ is pyrimidine-2,5-diyl, each of $Z^{14}$ and $Z^{15}$ is not —$CF_2O$—.

[14] The liquid crystal composition according to item [10], further containing at least one compound selected from the group consisting of compounds of Formula (5) according to item [11].

[15] The liquid crystal composition according to item [10], further containing at least one compound selected from the group consisting of compounds of Formulas (11), (12), and (13) according to item [13].

[16] The liquid crystal composition according to item [11], further containing at least one compound selected from the group consisting of compounds of Formulas (11), (12), and (13) according to item [13].

[17] The liquid crystal composition according to item [12], further containing at least one compound selected from the group consisting of compounds of Formulas (11), (12), and (13) according to item [13].

[18] The liquid crystal composition according to any one of items [1] to [9], further containing at least one compound selected from the group consisting of compounds of Formulas (15), (16), (17), and (18):

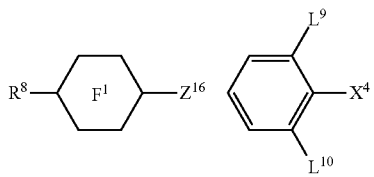

(15)

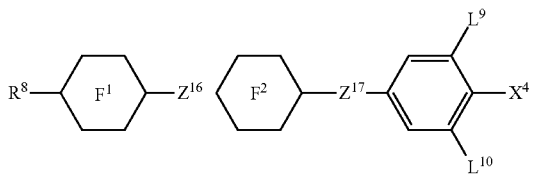

(16)

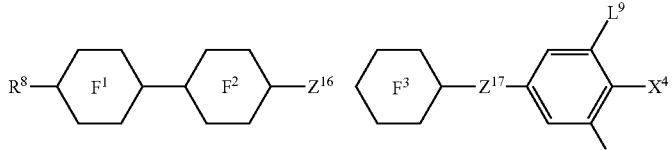

(17)

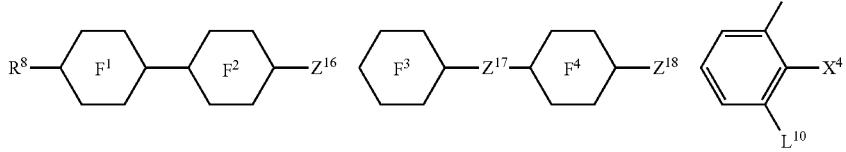

(18)

in which $R^8$ is a $C_{1-10}$ alkyl, a $C_{2-10}$ alkenyl, or a $C_{2-10}$ alkynyl, in which arbitrary —$CH_2$— in the alkyl, the alkenyl, and the alkynyl may be replaced by —O—, and arbitrary hydrogen in the alkyl, the alkenyl, the alkynyl, or the alkyl, the alkenyl, and the alkynyl with arbitrary —$CH_2$— replaced by —O— may be replaced by fluorine; $X^4$ is fluorine, chlorine, —$SF_5$, —$OCF_3$, —$OCHF_2$, —$CF_3$, —$CHF_2$, —$CH_2F$, —$OCF_2CHF_2$, or —$OCF_2CHFCF_3$; rings $F^1$, $F^2$, $F^3$, and $F^4$ are independently 1,4-cyclohexylene, 1,3-dioxane-2,5-diyl, pyrimidine-2,5-diyl, tetrahydropyrane-2,5-diyl, 1,4-phenylene, naphthalene-2,6-diyl, 1,4-phenylene with arbitrary hydrogen replaced by fluorine or chlorine, or naphthalene-2,6-diyl with arbitrary hydrogen replaced by fluorine or chlorine; $Z^{16}$, $Z^{17}$, and $Z^{18}$ are independently —$(CH_2)_2$—, —$(CH_2)_4$—, —COO—, —$CF_2O$—, —$OCF_2$—, —CH=CH—, —C≡C—, —$CH_2O$—, or a single bond, in which when at least one of the rings $F^1$-$F^4$ is pyrimidine-2,5-diyl, each of $Z^{16}$, $Z^{17}$, and $Z^{18}$ is not —$CF_2O$—; and $L^9$ and $L^{10}$ are independently hydrogen or fluorine.

[19] The liquid crystal composition according to any one of items [1] to [9], further containing at least one compound selected from the group consisting of compounds of Formula (19):

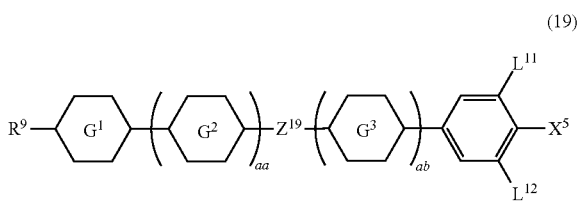

(19)

in which $R^9$ is a $C_{1-10}$ alkyl, a $C_{2-10}$ alkenyl, or a $C_{2-10}$ alkynyl, in which arbitrary —$CH_2$— in the alkyl, the alkenyl, and the alkynyl may be replaced by —O—, and arbitrary hydrogen in the alkyl, the alkenyl, the alkynyl, or the alkyl, the alkenyl, and the alkynyl with arbitrary —$CH_2$— replaced by —O— may be replaced by fluorine; $X^5$ is —C≡N, —N=C=S, or —C≡C—C≡N; rings $G^1$, $G^2$, and $G^3$ are independently 1,4-cyclohexylene, 1,4-phenylene, 1,4-phenylene with arbitrary hydrogen replaced by fluorine or chlorine, naphthalene-2,6-diyl, naphthalene-2,6-diyl with arbitrary hydrogen replaced by fluorine or chlorine, 1,3-dioxane-2,5-diyl, tetrahydropyrane-2,5-diyl, or pyrimidine-2,5-diyl; $Z^{19}$ is —$(CH_2)_2$—, —COO—, —$CF_2O$—, —$OCF_2$—, —C≡C—, —$CH_2O$—, or a single bond, in which when at least one of the rings $G^1$-$G^3$ is pyrimidine-2,5-diyl, $Z^{19}$ is not —$CF_2O$—; $L^{11}$ and $L^{12}$ are independently hydrogen or fluorine; aa is 0, 1, or 2, ab is 0 or 1, aa+ab is 0, 1 or 2.

[20] The liquid crystal composition according to any one of items [1] to [19], containing at least one antioxidant and/or UV absorbent.

[21] The liquid crystal composition according to any one of items [1] to [20], in which the optically isotropic liquid crystal phase does not exhibit two or more colors of diffracted light.

[22] The liquid crystal composition according to any one of items [1] to [20], in which the optically isotropic liquid crystal phase exhibits two or more colors of diffracted light.

[23] The liquid crystal composition according to item [21] or [22], obtained by adding the chiral dopant into a composition having a temperature difference between an upper-limit temperature and a lower-limit temperature of 3° C.-150° C. of co-existence of a chiral nematic phase and a non-liquid crystal isotropic phase.

[24] The liquid crystal composition according to item [21] or [22], obtained by adding the chiral dopant into a composition having a temperature difference between an upper-limit temperature and a lower-limit temperature of 5° C.-150° C. of co-existence of a chiral nematic phase and a non-liquid crystal isotropic phase.

[25] The liquid crystal composition according to item [21] or [22], obtained by adding the chiral dopant into a composition having a temperature difference between an upper-limit temperature and a lower-limit temperature of 3° C.-150° C. of co-existence of a nematic phase and a non-liquid crystal isotropic phase.

[26] The liquid crystal composition according to any one of items [1] to [25], in which a content of the chiral dopant is 1 wt %-40 wt % based on the total weight of the liquid crystal composition.

[27] The liquid crystal composition according to any one of items [1] to [25], in which a content of the chiral dopant is 5 wt %-15 wt % based on the total weight of the liquid crystal composition.

[28] The liquid crystal composition according to items [26] or [27], exhibiting a chiral nematic phase at any temperature in the range of 70° C. to −20° C., and having a helical pitch of 700 nm or less within at least a part of the temperature range.

[29] The liquid crystal composition according to any one of items [26] to [28], in which the chiral dopant contains at least one compound selected from the group of compounds of Formulas (K1)-(K5):

(K1)

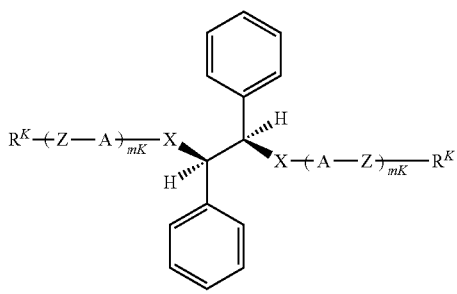

(K2)

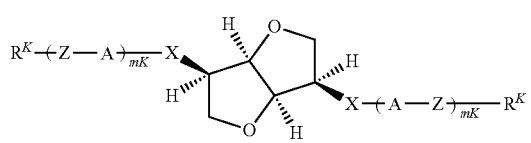

(K3)

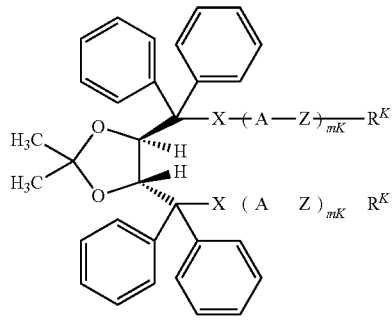

(K4)

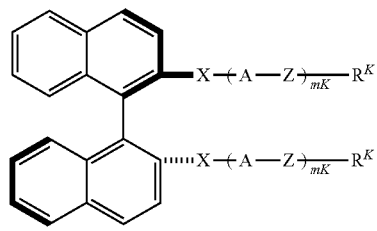

(K5)

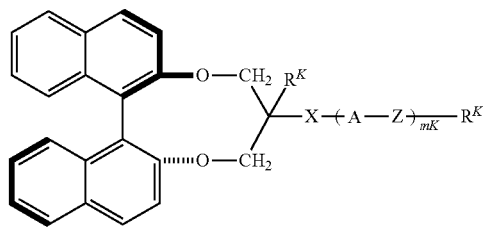

(in Formulas (K1)-(K5), $R^K$ is independently hydrogen, halogen, —N=C=O, —N=C=S, or a $C_{1-20}$ alkyl, in which arbitrary —$CH_2$— in the alkyl may be replaced by —O—, —S—, —COO—, —OCO—, —CH=CH—, —CF=CF—, or —C≡C—, and arbitrary hydrogen in the alkyl and the alkyl with arbitrary —$CH_2$— replaced by —O—, —S—, —COO—, —OCO—, —CH=CH—, —CF=CF—, or —C≡C— may be replaced by halogen; A is independently an aromatic or non-aromatic 3- to 8-membered ring, or a fused ring having 9 or more carbon atoms, in which arbitrary hydrogen in the rings may be replaced by halogen, a $C_{1-3}$ alkyl, or a haloalkyl, —$CH_2$— in the rings may be replaced by —O—, —S—, or —NH—, and —CH= may be replaced by —N=; and Z is independently a single bond or a $C_{1-8}$ alkylene, in which arbitrary —$CH_2$— may be replaced by —O—, —S—, —COO—, —OCO—, —CSO—, —OCS—, —N=N—, —CH=N—, —N=CH—, —CH=CH—, —CF=CF—, or —C≡C—, and arbitrary hydrogen may be replaced by halogen;

X is independently a single bond, —COO—, —OCO—, —$CH_2O$—, —$OCH_2$—, —$CF_2O$—, —$OCF_2$—, or —$CH_2CH_2$—; and mK is independently an integer of 1-4).

[30] The liquid crystal composition according to any one of items [26] to [28], in which the chiral dopant contains at least one compound selected from the group consisting of compounds of Formulas (K2-1)-(K2-8) and Formulas (K5-1)-(K5-3):

(K2-1)

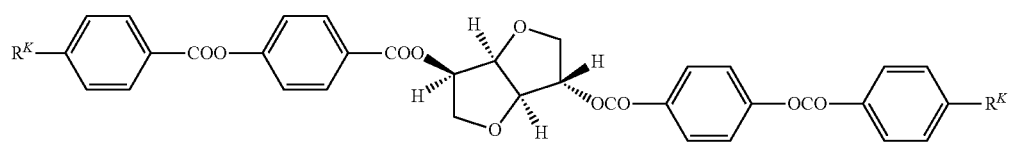

(K2-2)

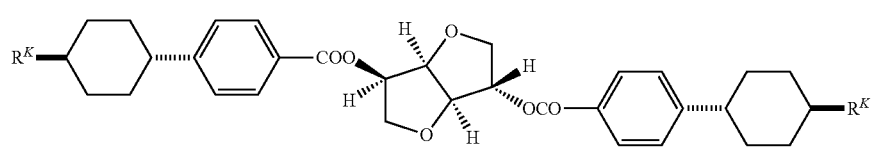

(K2-3)

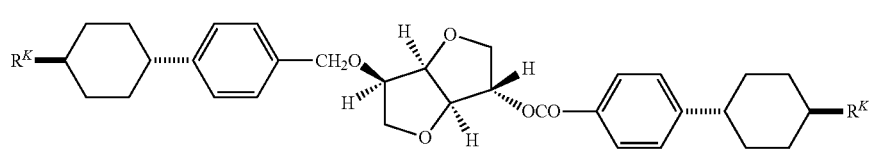

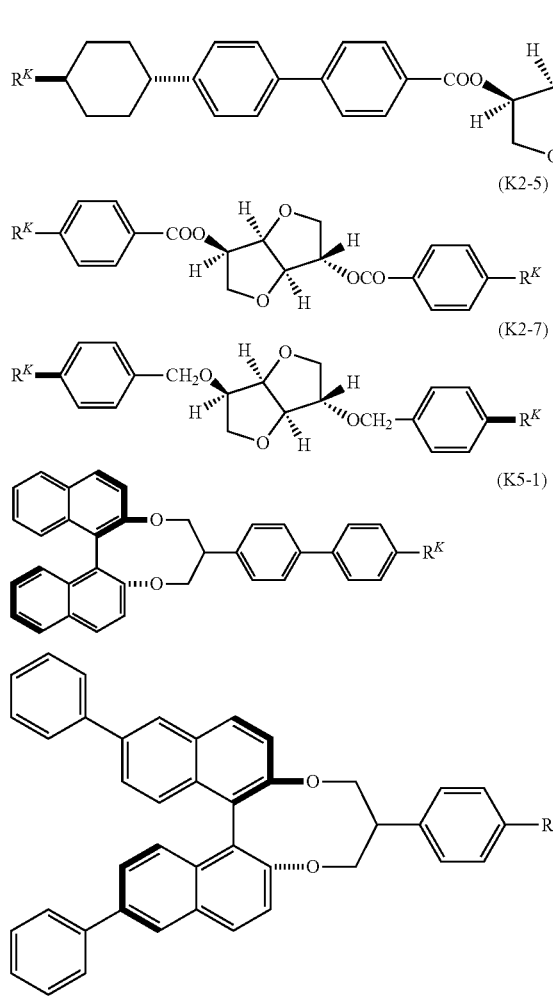
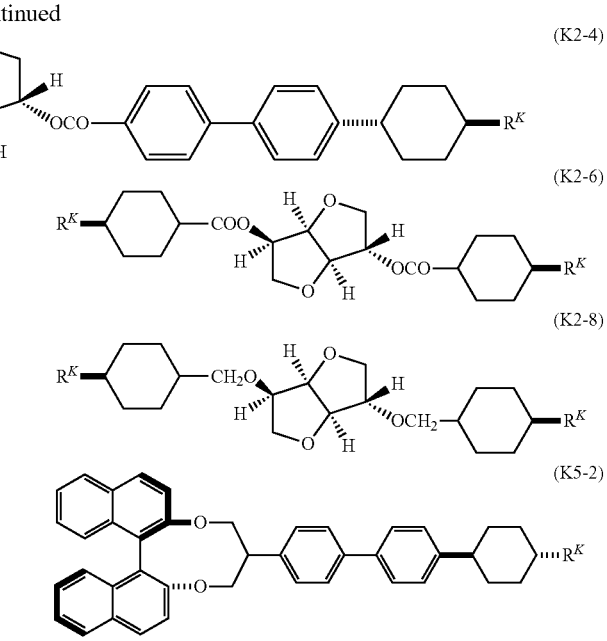

($R^K$ is independently a $C_{3-10}$ alkyl, in which —$CH_2$— adjacent to the ring in the alkyl may be replaced by —O—, and arbitrary —$CH_2$— may be replaced by —CH=CH—).

[31] A mixture, containing the liquid crystal composition according to any one of items [1] to [30] and a polymerizable monomer.

[32] The mixture according to item [31], in which the polymerizable monomer is a photopolymerizable monomer or a thermal-polymerizable monomer.

[33] A polymer/liquid crystal composite material, obtained by polymerizing the mixture according to item [31] or [32], for use in a device driven in an optically isotropic liquid crystal phase.

[34] The polymer/liquid crystal composite material according to item [33], obtained by polymerizing the mixture according to item [31] or [32] in a non-liquid crystal isotropic phase or an optically isotropic liquid crystal phase.

[35] The polymer/liquid crystal composite material according to item [33], in which the polymer contained in the polymer/liquid crystal composite material has a mesogen moiety.

[36] The polymer/liquid crystal composite material according to any one of items [33] to [35], in which the polymer contained in the polymer/liquid crystal composite material has a cross-linked structure.

[37] The polymer/liquid crystal composite material according to any one of items [33] to [36], in which a content of the liquid crystal composition is 60-99 wt %, and a content of the polymer is 1-40 wt %.

[38] An optical device, containing a liquid crystal medium disposed between substrates having electrodes disposed on either or both surfaces thereof and an electric field-applying means for applying an electric field to the liquid crystal medium via the electrodes, in which the liquid crystal medium is the liquid crystal composition according to any one of items [26] to [30] or the polymer/liquid crystal composite material according to any one of items [33] to [37].

[39] An optical device, containing a set of substrates having electrodes disposed on either or both surfaces thereof, at least one of which being transparent, a liquid crystal medium disposed between the substrates, a polarizer disposed outside of the substrates, and an electric field-applying means for applying an electric field to the liquid crystal medium via the electrodes, in which the liquid crystal medium is the liquid crystal composition according to any one of items [26] to [30] or the polymer/liquid crystal composite material according to any one of items [33] to [37].

[40] The optical device according to item [39], in which on at least one of the set of substrates, the electrodes are constructed in a manner such that an electric field is applied in at least two directions.

[41] The optical device according to item [39], in which on one or two of the set of substrates disposed in parallel with each other, the electrodes are constructed in a manner such that an electric field is applied in at least two directions.

[42] The optical device according to any one of items [38] to [41], in which the electrodes are disposed in a matrix form to form pixel electrodes, and each pixel is provided with an active element being a thin film transistor (TFT).

According to the present invention, the so-called liquid crystal medium is a general term of a liquid crystal composition and a polymer/liquid crystal composite. Furthermore, the so-called optical device refers to various devices using electro-optic effect to achieve the function of optical modulation or optical switching, for example, display devices (LCD devices), and optical modulation devices used in optical communication systems, optical information processing or various sensor systems. As for the optical modulation with changes in refractive index caused by applying a voltage to an optically isotropic liquid crystal medium, the Kerr effect is known. The so-called Kerr effect is a phenomenon that a electrically controlled birefringence value $\Delta n(E)$ is proportional to square of electric field E, that is, $\Delta n(E)=K\lambda E^2$ (K: Ken coefficient (Kerr constant), $\lambda$: wavelength) in a material exhibiting the Kerr effect. Here, the so-called electrically controlled birefringence value refers to an optical anisotropy value induced by applying an electric field to an isotropic medium.

The terms used in this specification are defined as follows. The liquid crystal compound is a general term of a compound having a liquid crystal phase such as nematic phase and smectic phase and a compound having no liquid crystal phase but being useful as a component of a liquid crystal composition. The chiral dopant is an optical active compound, which is added to impart the necessary twisted molecular arrangement to a liquid crystal composition. The LCD device is a general term of an LCD panel and an LCD module. The liquid crystal compound, the liquid crystal composition, and the LCD device are sometimes simply called as the compound, the composition, and the device, respectively. Furthermore, for example, the upper-limit temperature of the liquid crystal phase is the liquid crystal phase-isotropic phase transition temperature, and sometimes only simply called as the clearing point or upper-limit temperature, and the lower-limit temperature of the liquid crystal phase is sometimes only simply called as the lower-limit temperature. The compound of Formula (1) is sometimes simply called as Compound (1), and this abbreviation also applies to a compound of Formula (2) etc. In Formulas (1)-(19), the symbols B, D, and E surrounded by hexagons are corresponding to rings B, D, and E, respectively. The compound content by percentage is weight percent (wt %) based on the total weight of the composition. A plurality of identical symbols such as ring $A^1$, $Y^1$, or B are included in the same or different formulas; however, the groups represented by these symbols can be identical or different.

"Arbitrary" denotes not only arbitrary position, but also arbitrary number, except for the case when the number is 0. The expression that arbitrary A may be replaced by B, C, or D not only means arbitrary A may be replaced by B, arbitrary A may be replaced by C, and arbitrary A may be replaced by D, but also means that a plurality of A may be replaced by at least two of B-D. For example, the alkyl in which arbitrary —CH$_2$— may be replaced by —O— or —CH=CH— includes alkyl, alkenyl, alkoxy, alkoxyalkyl, alkoxyalkenyl, alkenyloxyalkyl, and the like. Furthermore, in the present invention, the case in which two contiguous —CH$_2$— are replaced by —O— to form —O—O— is unsuitable, and the case in which the terminal —CH$_2$— in an alkyl is replaced by —O— is also unsuitable. The present invention will be further described below. The terminal groups, rings, and bonding groups of the compound of Formula (1) will also be illustrated with preferred examples.

Effects of the Invention

The liquid crystal composition of the present invention is stable to heat and light, and has a high upper-limit temperature and a low lower-limit temperature of an optically isotropic liquid crystal phase, and a low driving voltage when being used in a device driven in an optically isotropic liquid crystal phase. The polymer/liquid crystal composite material of the present invention has a material of an optically isotropic liquid crystal phase, exhibits a high upper-limit temperature and a low lower-limit temperature of an optically isotropic liquid crystal phase, and has a low driving voltage when being used in a device driven in an optically isotropic liquid crystal phase.

The optical device of the present invention driven in an optically isotropic liquid crystal phase has a wide usable temperature range, a short response time, a high contrast, and a low driving voltage.

Figure 1:
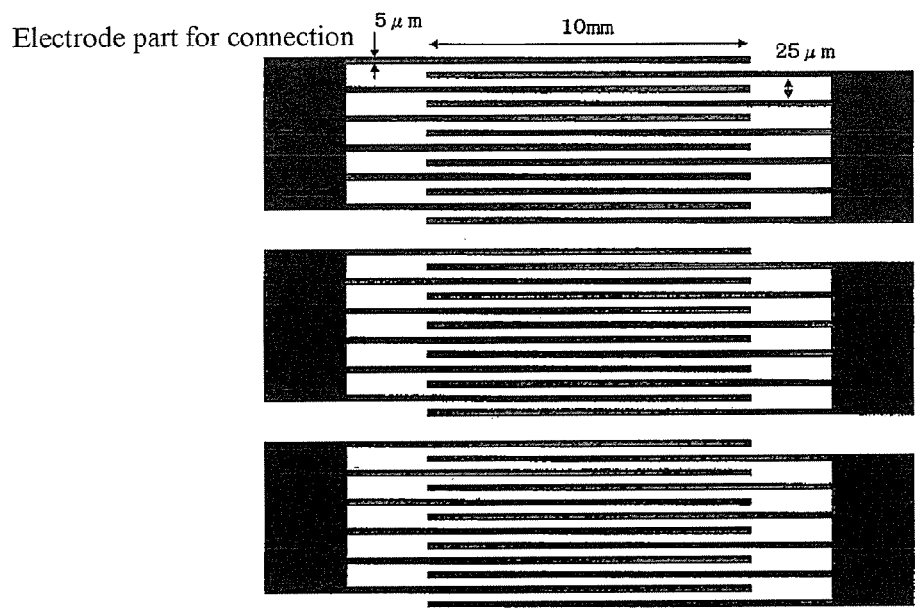
FIG. 1 shows a comb-like electrode substrate used in an Example.

DESCRIPTION OF THE EMBODIMENTS 1-1 Compound (1)

The liquid crystal composition having an optically isotropic liquid crystal phase of the present invention contains a compound of Formula (1) as Component A. A first aspect of the present invention is a composition only containing the Component A or a composition containing the Component A and other components not specifically disclosed in the specification. First, the compound of Formula (1) is described.

(1)

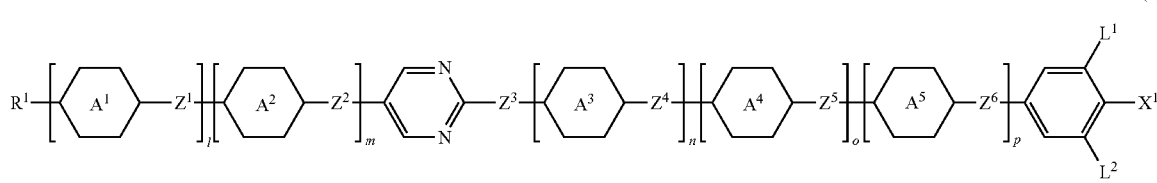

In Formula (1), $R^1$ is hydrogen or a $C_{1-20}$ alkyl, in which arbitrary —CH$_2$— in the alkyl may be replaced by —O—, —S—, —COO—, —OCO—, —CH=CH—, —CF=CF—, or —C≡C—, and arbitrary hydrogen in the alkyl and the alkyl with arbitrary —CH$_2$— replaced by —O—, —S—, —COO—, —OCO—, —CH=CH—, —CF=CF—, or —C≡C— may be replaced by halogen or a $C_{1-3}$ alkyl.

For example, examples of the group formed by substituting arbitrary —CH$_2$— in CH$_3$(CH$_2$)$_3$— with —O—, —S—, or —CH=CH— are CH$_3$(CH$_2$)$_2$O—, CH$_3$—O—(CH$_2$)$_2$—, CH$_3$—O—CH$_2$—O—, CH$_3$(CH$_2$)$_2$S—, CH$_3$—S—(CH$_2$)$_2$—, CH$_3$—S—CH$_2$—S—, CH$_2$=CH—(CH$_2$)$_3$—, CH$_3$—CH=CH—(CH$_2$)$_2$—, CH$_3$—CH=CH—CH$_2$O—, and CH₃CH₂C≡C—. For example, examples of the group formed by substituting arbitrary hydrogen in CH₃(CH₂)₃— or CH₃(CH₂)₃— with arbitrary —CH₂— replaced by —O—, —C≡C—, or —CH═CH— with halogen are ClCH₂(CH₂)₃—, CF₂═CH—(CH₂)₃—, CH₂F(CH₂)₂O—, and CH₂FCH₂C≡C—.

As for such a $R^1$, a linear group is preferred to a branched group. Even when $R^1$ is a branched group, a group having optical activity is preferred. A preferred stereo configuration of —CH═CH— in alkenyl depends on the position of the double bond. A trans configuration is preferred for such an alkenyl having a double bond at an odd position, such as —CH═CHCH₃, —CH═CHC₂H₅, —CH═CHC₃H₇, —CH═CHC₄H₉, —C₂H₄CH═CHCH₃, and —C₂H₄CH═CHC₂H₅. A cis configuration is preferred for such an alkenyl having a double bond at an even position, such as —CH₂CH═CHCH₃, —CH₂CH═CHC₂H₅, and —CH₂CH═CHC₃H₇. An alkenyl compound having a preferred stereo configuration has a high upper-limit temperature, or a wide temperature range of a liquid crystal phase, as illustrated in detail in *Mol. Cryst. Liq. Cryst.*, 1985, 131, 109; and *Mol. Cryst. Liq. Cryst.*, 1985, 131, 327.

The alkyl may be linear or branched, and specific examples include —CH₃, —C₂H₅, —C₃H₇, —C₄H₉, —C₅H₁₁, —C₆H₁₃, —C₇H₁₅, —C₈H₁₇, —C₉H₁₉, —C₁₀H₂₁, —C₁₁H₂₃, —C₁₂H₂₅, —C₁₃H₂₇, —C₁₄H₂₉, and —C₁₅H₃₁.

The alkoxyl may be linear or branched, and specific examples include —OCH₃, —OC₂H₅, —OC₃H₇, —OC₄H₉, —CO₅H₁₁, —CO₆H₁₃, and —CO₇H₁₅, —CO₈H₁₇, —OC₉H₁₉, —OC₁₀H₂₁, —OC₁₁H₂₃, —OC₁₂H₂₅, —OC₁₃H₂₇, and —OC₁₄H₂₉.

The alkoxyalkyl may be linear or branched, and specific examples include —CH₂OCH₃, —CH₂OC₂H₅, —CH₂OC₃H₇, —(CH₂)₂—OCH₃, —(CH₂)₂—OC₂H₅, —(CH₂)₂—OC₃H₇, —(CH₂)₃—OCH₃, —(CH₂)₄—OCH₃, and —(CH₂)₅—OCH₃.

The alkenyl may be linear or branched, and specific examples include —CH═CH₂, —CH═CHCH₃, —CH₂CH═CH₂, —CH═CHC₂H₅, —CH₂CH═CHCH₃, —(CH₂)₂—CH═CH₂, —CH═CHC₃H₇, —CH₂CH═CHC₂H₅, —(CH₂)₂—CH═CHCH₃, and —(CH₂)₃—CH═CH₂.

The alkenyloxy may be linear or branched, and specific examples include —OCH₂CH═CH₂, —OCH₂CH═CHCH₃, and —OCH₂CH═CHC₂H₅.

The alkynyl may be linear or branched, and specific examples include —C≡CCH₃, —CH₂C≡CH, —C≡CC₂H₅, —CH₂C≡CCH₃, —(CH₂)₂—C≡CH, —C≡CC₃H₇, —CH₂C≡CC₂H₅, —(CH₂)₂—C≡CCH₃, and —C≡C(CH₂)₅.

Preferably, $R^1$ has a structure of Formulas (CHN-1)-(CHN-19). Here, $R^{1a}$ is hydrogen or a $C_{1-20}$ alkyl. Preferably, $R^1$ has a structure of Formulas (CHN-1)-(CHN-4) or Formulas (CHN-6)-(CHN-8), and a structure of Formulas (CHN-1), (CHN-4), (CHN-5), and (CHN-7) is more preferred, in view of voltage holding ratio.

$R^{1a}$— (CHN-1)

 (CHN-2)

 (CHN-3)

 (CHN-4)

$R^{1a}$ (CHN-5)

$R^{1a}$ (CHN-6)

$R^{1a}$ (CHN-7)

$R^{1a}$ (CHN-8)

$R^{1a}$ (CHN-9)

$R^{1a}$ (CHN-10)

$R^{1a}$—O— (CHN-11)

$R^{1a}$ O— (CHN-12)

$R^{1a}$ O— (CHN-13)

$R^{1a}$—S— (CHN-14)

$R^{1a}$ S— (CHN-15)

$R^{1a}$ S— (CHN-16)

(CHN-17)

(CHN-18)

(CHN-19)

In Formula (1), rings $A^1$, $A^2$, $A^3$, $A^4$, and $A^5$ are independently a benzene ring, a naphthalene ring, a thiophene ring, a cyclohexene ring, a bicyclo-octane ring, a tetrahydronaphthalene ring, or a cyclohexane ring, in which arbitrary hydrogen in the rings may be replaced by halogen, a $C_{1-3}$ alkyl, alkoxy, or haloalkyl, —CH₂— in the rings may be replaced by —O—, or —S—, and —CH═ may be replaced by —N═. Preferred examples of the rings $A^1$, $A^2$, $A^3$, $A^4$, and $A^5$ are structures of Formulas (RG-1)-(RG-15), $Y^1$, $Y^2$, $Y^3$, and $Y^4$ are independently hydrogen or halogen, and fn1, fn2, fn3, and fn4 are independently 0, 1, 2, or 3.

 (RG-1)

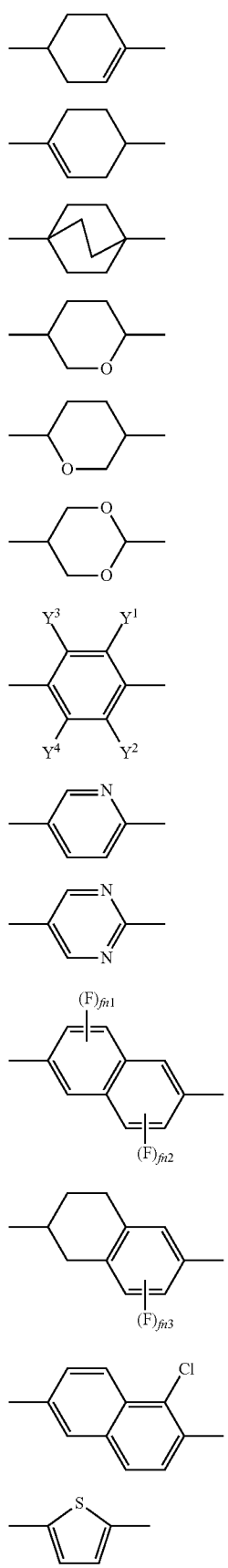
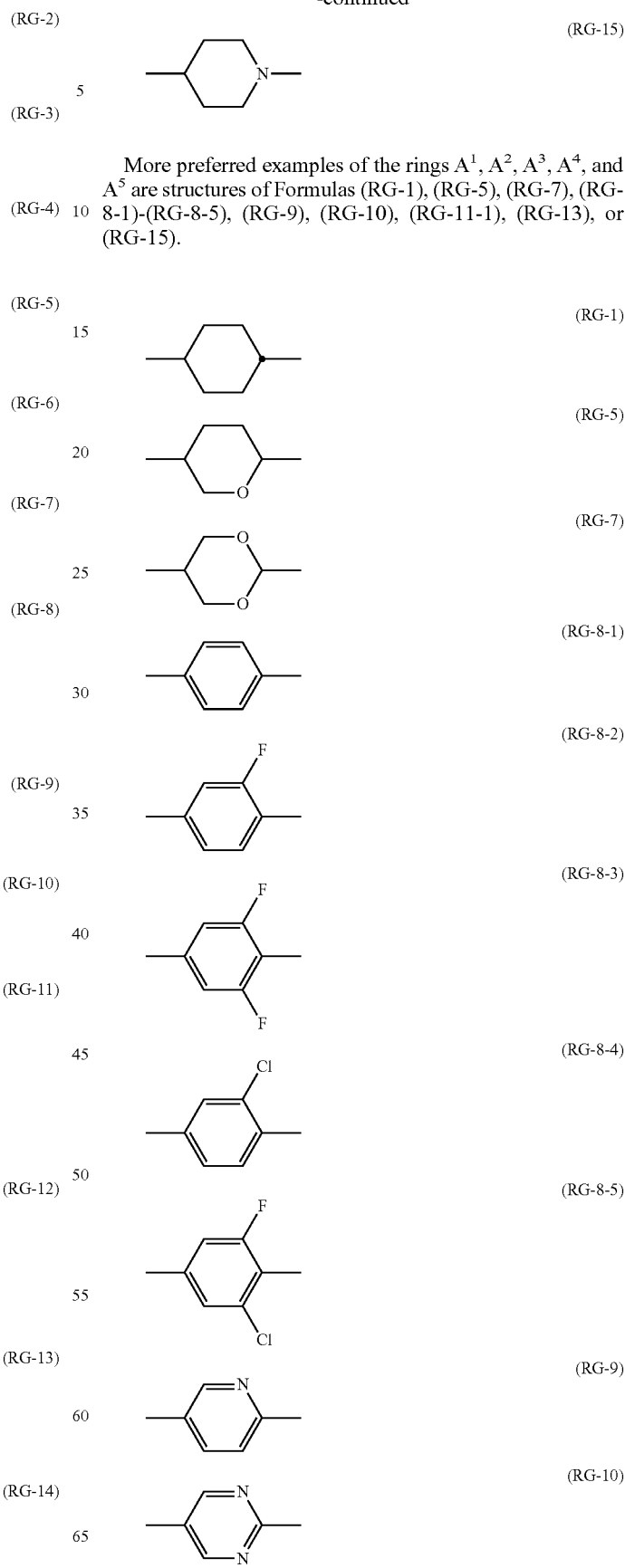
More preferred examples of the rings $A^1$, $A^2$, $A^3$, $A^4$, and $A^5$ are structures of Formulas (RG-1), (RG-5), (RG-7), (RG-8-1)-(RG-8-5), (RG-9), (RG-10), (RG-11-1), (RG-13), or (RG-15).

(RG-11-1)

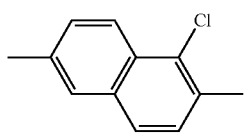
(RG-13)

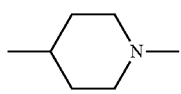
(RG-15)

In Formula (1), $Z^1$, $Z^2$, $Z^3$, $Z^4$, $Z^5$ and $Z^6$ are independently a single bond and a $C_{1-4}$ alkylene, in which arbitrary —$CH_2$— in the alkylene may be replaced by —O—, —S—, —COO—, —OCO—, —CSO—, —OCS—, —CH=CH—, —CF=CF—, or —C≡C—, and arbitrary hydrogen in the alkylene and the alkylene with arbitrary —$CH_2$— replaced by —O—, —S—, —COO—, —OCO—, —CSO—, —OCS—, —CH=CH—, —CF=CF—, or —C≡C— may be replaced by halogen, provided that at least one of $Z^1$, $Z^2$, $Z^3$, $Z^4$, $Z^5$, and $Z^6$ is —$CF_2$O—.

Preferred examples of $Z^1$, $Z^2$, $Z^3$, $Z^4$, $Z^5$, and $Z^6$ are a single bond, —$CH_2CH_2$—, —CH=CH—, —C≡C—, —COO—, —$CF_2$O—, —$CH_2$O—, or —$OCH_2$—. In the bonds, as for the stereo configuration of the double bond of bonding groups, such as, —CH=CH—, —CF=CF—, —CH=CH—$(CH_2)_2$—, and —$(CH_2)_2$—CH=CH—, trans configuration is superior to cis configuration. Preferably, $Z^1$, $Z^2$, $Z^3$, $Z^4$, $Z^5$, and $Z^6$ are a single bond, —COO—, and —$CF_2$O—, and a single bond and —$CF_2$O— are particularly preferred, in view of voltage holding ratio.

In Formula (1), $L^1$ and $L^2$ are independently hydrogen or halogen, and preferably, hydrogen or fluorine.

In Formula (1), $X^1$ is hydrogen, halogen, —C≡N, —N=C=S, —C≡C—C≡N, —$SF_5$, or a $C_{1-10}$ alkyl, in which arbitrary —$CH_2$— in the alkyl may be replaced by —O—, —S—, —CH=CH—, and arbitrary hydrogen in the alkyl and the alkyl with arbitrary —$CH_2$— replaced by —O—, —S—, —CH=CH—, or —C≡C— may be replaced by halogen.

Specific examples of alkyl with arbitrary hydrogen replaced by halogen are —$CH_2F$, —$CHF_2$, —$CF_3$, —$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F, and —$(CF_2)_5$—F.

Specific examples of alkoxy with arbitrary hydrogen replaced by halogen are —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —$O(CH_2)_4$—F, —O—$(CF_2)_4$—F, —O—$(CH_2)_5$—F, and —O—$(CF_2)_5$—F.

Specific examples of alkenyl with arbitrary hydrogen replaced by halogen are —CH=CHF, —CH=$CF_2$, —CF=CHF, —CH=$CHCH_2F$, —CH=$CHCF_3$, —$(CH_2)_2$—CH=$CF_2$, —$CH_2CH$=$CHCF_3$, and —CH=$CHCF_2CF_3$.

Specific examples of $X^1$ are hydrogen, fluorine, chlorine, —C≡N, —N=C=S, —$SF_5$, —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$CH_2F$, —$CHF_2$, —$CF_3$, —$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F, —$(CF_2)_5$—F, —$OCH_3$, —$OC_2H_5$, —$OC_3H_7$, —$OC_4H_9$, —$OC_5H_{11}$, —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —$O(CH_2)_4$—F, —O—$(CF_2)_4$—F, —O—$(CH_2)_5$—F, —O—$(CF_2)_5$—F, —CH=$CH_2$, —CH=$CHCH_3$, —$CH_2CH$=$CH_2$, —CH=$CHC_2H_5$, —$CH_2CH$=$CHCH_3$, —$(CH_2)_2$—CH=$CH_2$, —CH=$CHC_3H_7$, —$CH_2CH$=$CHC_2H_5$, —$(CH_2)_2$—CH=$CHCH_3$, —$(CH_2)_3$—CH=$CH_2$, —CH=CHF, —CH=$CF_2$, —CF=CHF, —CH=$CHCH_2F$, —CH=$CHCF_3$, —$(CH_2)_2$—CH=$CF_2$, —$CH_2CH$=$CHCF_3$, and —CH=$CHCF_2CF_3$.

Preferred examples of $X^1$ are fluorine, chlorine, —C≡N, —$CF_3$, —$CHF_2$, —$CH_2F$, —$OCF_3$, —$OCHF_2$, and —$OCH_2F$. Most preferred examples of $X^1$ are fluorine, chlorine, —$CF_3$, and —$OCF_3$.

In Formula (1), l, m, n, o, and p are independently 0 or 1, l+m+n+o+p≦4, more preferably l+m+n+o+p≦3, and most preferably l+m+n+o+p≦2.

In Formula (1), structures of Formulas (1-1)-(1-8) are preferred.

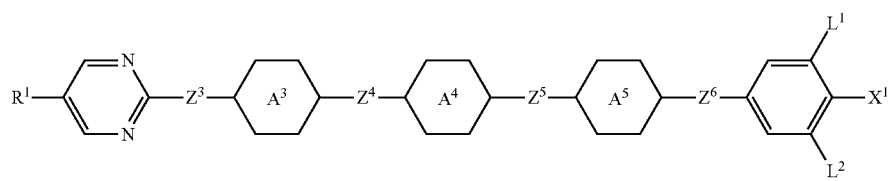
(1-1)

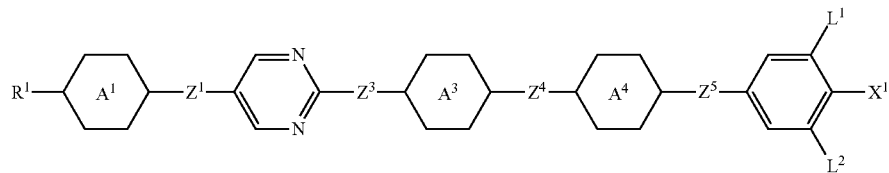
(1-2)

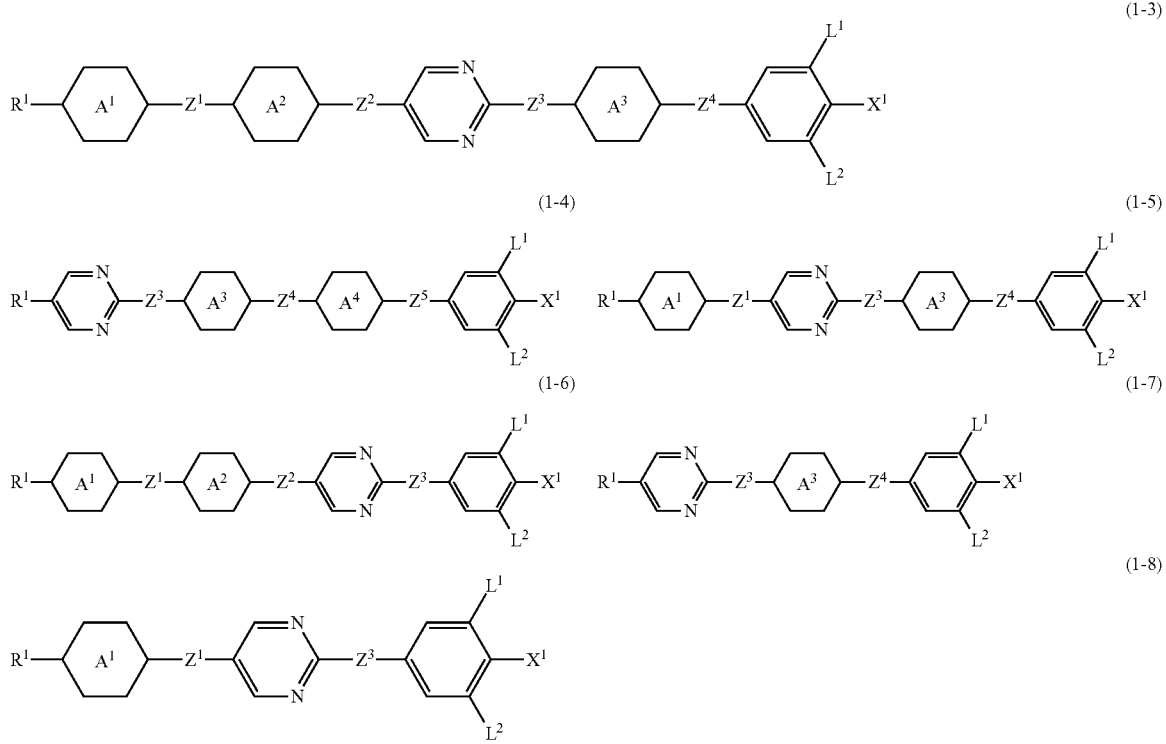

In the formulas, $R^1$ is a structure of any one of Formulas (CHN-1)-(CHN-19), $R^{1a}$ is hydrogen or a $C_{1-20}$ alkyl; rings $A^1, A^2, A^3, A^4$, and $A^5$ are independently one of structures of Formulas (RG-1)-(RG-15), $Y^1, Y^2, Y^3$, and $Y^4$ are independently hydrogen or halogen, fn1, fn2, fn3, and fn4 are independently 0, 1, 2, or 3; $Z^1, Z^2, Z^3, Z^4, Z^5$, and $Z^6$ are independently a single bond, —$CH_2CH_2$—, —CH=CH—, —COO—, —$CF_2O$—, —$CH_2O$—, or —$OCH_2$—, provided that at least one of $Z^1, Z^2, Z^3, Z^4, Z^5$, and $Z^6$ is —$CF_2O$—; $L^1$ and $L^2$ are independently hydrogen, fluorine, or chlorine; $X^1$ is fluorine, chlorine, —$CF_3$, —$CHF_2$, —$CH_2F$, —$OCF_3$, —$OCHF_2$, —$OCH_2F$, or —C≡C—$CF_3$.

1-2 Properties of Compound (1)

Compound (1) used in the present invention is further described in detail. Compound (1) is a liquid crystal compound having a pyrimidine ring and a linking group —$CF_2O$—, which has very stable physical and chemical properties under the conditions where the device is conventionally used, and has an excellent compatibility with other liquid crystal compounds. The composition containing such a compound is stable under the conditions where the device is conventionally used. Therefore, the composition containing the compound has an expanded temperature range of an optically isotropic liquid crystal phase, and thus can be used in a display device in a wide temperature range. Moreover, due to large dielectric anisotropy and large optical anisotropy, the compound may be used as a component for lowering the driving voltage of a composition driven in an optically isotropic liquid crystal phase.

By properly selecting the combination of l, m, n, o, and p, the types of rings $A^1$-$A^5$, the left terminal group $R^1$, the groups on the most right benzene ring and substitution positions thereof ($L^1, L^2$ and $X^1$), or the bonding groups $Z^1$-$Z^6$ in Compound (1), the physical properties such as clearing point, optical anisotropy, and dielectric anisotropy can be adjusted at will. The effects of the combination of l, m, n, o, and p, the types of rings $A^1$-$A^5$, the left terminal group $R^1$, the right terminal group $X^1$, the bonding groups $Z^1$-$Z^6$, and $L^1$-$L^2$ on the physical properties of Compound (1) will be described below.

Generally, the larger the value of 1+m+n+o+p is, the higher the clearing point of the compounds is, and the smaller the value of 1+m+n+o+p is, the lower the melting point of the compounds is.

The more the aromatic rings in rings $A^1$-$A^5$ is, the larger the optical anisotropy is. The structures of Formulas (RG-7), (RG-8-2)-(RG-8-5), (RG-9), (RG-10), and (RG-15) are effective in exhibiting a large dielectric anisotropy, the structures of Formulas (RG-8-1)-(RG-8-5), (RG-9), (RG-10), (RG-11-1), (RG-13), and (RG-15) are effective in exhibiting a large optical anisotropy, and the structures of Formulas (RG-1) and (RG-5) contribute to exhibition of good compatibility.

When $R^1$ is linear, Compound (1) has a wide temperature range of a liquid crystal phase and a low viscosity. When $R^1$ is branched, Compound (1) has good compatibility with other liquid crystal compounds. The compound in which $R^1$ is an optically active group may be used as a chiral dopant. The compound in which $R^1$ is a non-optically active group may be used as a component of the composition. When $R^1$ is an alkenyl, a preferred stereo configuration depends on the position of the double bond. An alkenyl compound having a preferred stereo configuration has a high upper-limit temperature or a wide temperature range of a liquid crystal phase When the bonding groups $Z^1, Z^2, Z^3, Z^4, Z^5$, and $Z^6$ are a single bond, —$CH_2CH_2$—, —CH=CH—, —$CF_2O$—, —$OCF_2$—, —$CH_2O$—, —$OCH_2$—, —CF=CF—, —$(CH_2)_3$—O—, —O—$(CH_2)_3$—, —$(CH_2)_2$—$CF_2O$—, —$OCF_2$—$(CH_2)_2$—, or —$(CH_2)_4$—, Compound (1) has a low viscosity. When the bonding groups are a single bond, —$(CH_2)_2$—, —$CF_2O$—, —$OCF_2$—, or —CH=CH—, Compound (1) has a further lower viscosity. When the bonding groups are —CH═CH—, Compound (1) has a wide temperature range of a liquid crystal phase and a large elastic constant ratio $K_{33}/K_{11}$ ($K_{33}$: bend elastic constant, $K_{11}$: splay elastic constant). When the bonding groups are —C≡C—, Compound (1) has a large optical anisotropy. When the bonding groups are —COO—, —CF$_2$O—, Compound (1) has a large dielectric anisotropy. When $Z^1$, $Z^2$, $Z^3$, $Z^4$, $Z^5$, and $Z^6$ are a single bond, —(CH$_2$)$_2$—, —CH$_2$O—, —CF$_2$O—, —OCF$_2$—, or —(CH$_2$)$_4$—, Compound (1) has stable chemical properties, and is unlikely to be deteriorated.

When the right terminal group $X^1$ is fluorine, chlorine, —N═C═S, —SF$_5$, —CF$_3$, —CHF$_2$, —CH$_2$F, —OCF$_3$, —OCHF$_2$, or —OCH$_2$F, Compound (1) has a large dielectric anisotropy. When $X^1$ is —C≡N, —N═C═S, or alkenyl, Compound (1) has a large optical anisotropy. When $X^1$ is fluorine, chlorine, —CF$_3$, —CHF$_2$, —CH$_2$F, —OCF$_3$, —OCHF$_2$, or —OCH$_2$F, Compound (1) has stable chemical properties.

When $L^1$ and $L^2$ are both fluorine, $X^1$ is fluorine, chlorine, —N═C═S, —SF$_5$, —CF$_3$, —CHF$_2$, —CH$_2$F, —OCF$_3$, —OCHF$_2$, or —OCH$_2$F, Compound (1) has a large dielectric anisotropy. When $L^1$ is fluorine and $X^1$ is —CF$_3$ or —OCF$_3$, when $L^1$ and $L^2$ are both fluorine and $X^1$ is —CF$_3$ or —OCF$_3$, or when $L^1$, $L^2$ and $X^1$ all are fluorine, Compound (1) has a large dielectric anisotropy, a wide temperature range of a liquid crystal phase, and stable chemical properties, and thus is unlikely to be deteriorated.

As described above, a compound with target properties can be obtained by properly selecting the ring structures, the types of the terminal groups, bonding groups, and the like.

1-3 Specific Examples of Compound (1)

Preferred examples of Compound (1) are Formulas (1-1)-(1-8). More preferred examples are Formulas (1-1A)-(1-1C), (1-2A)-(1-2B), (1-3A), (1-4A)-(1-4C), (1-5A)-(1-5C), (1-6A)-(1-6C), (1-7A).

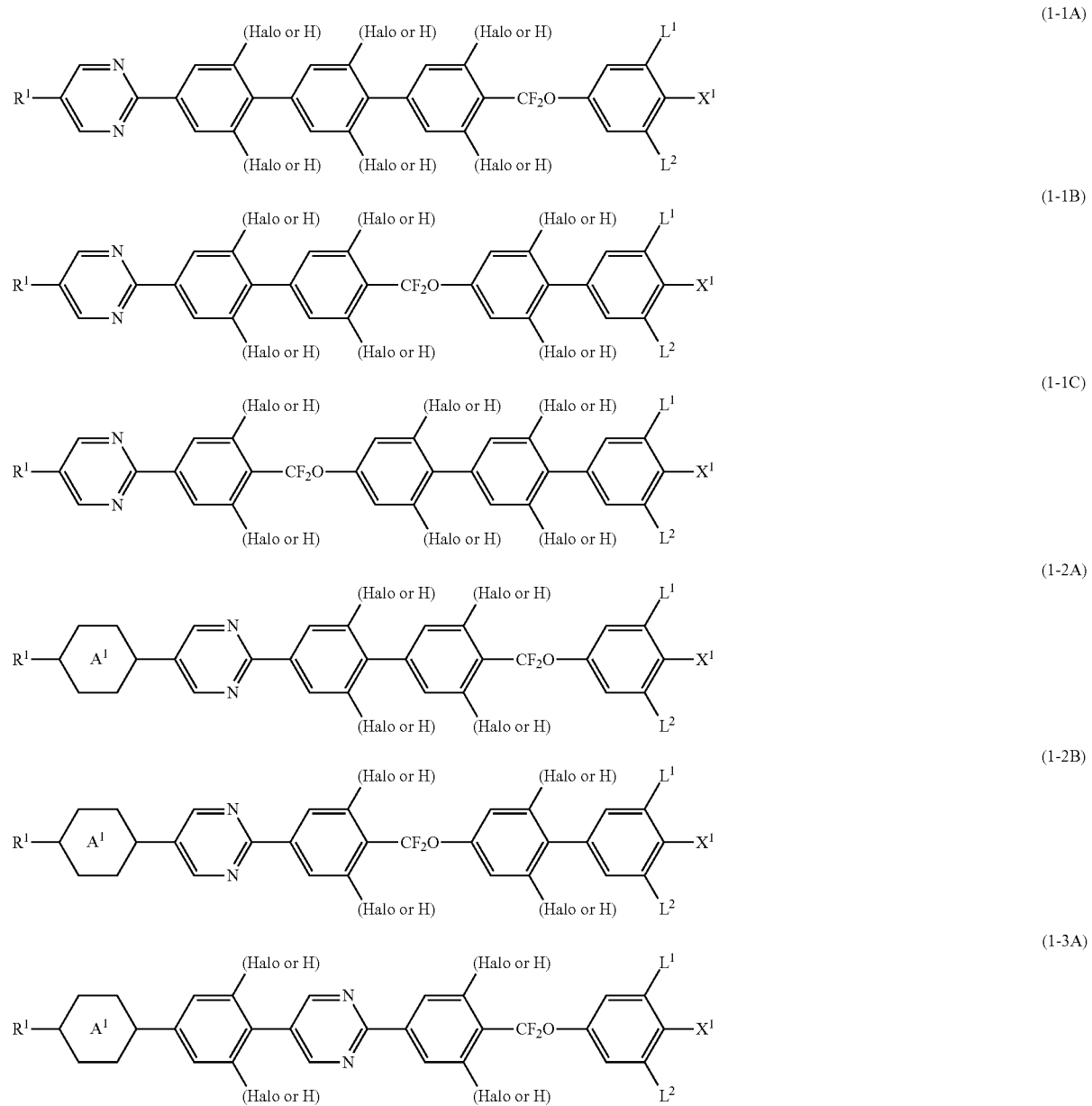

-continued

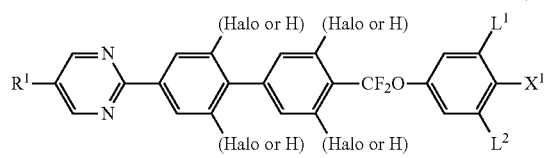
(1-4A)

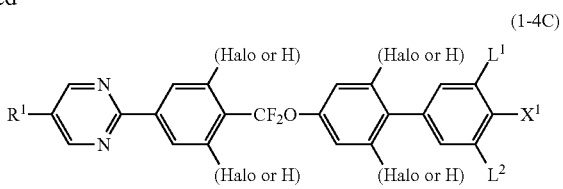
(1-4C)

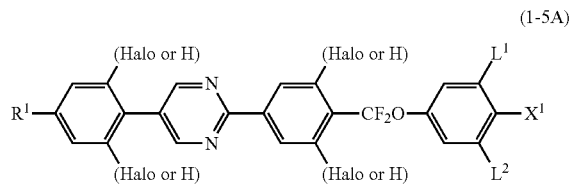
(1-5A)

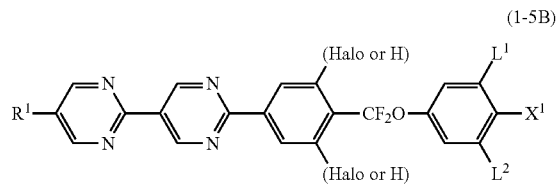
(1-5B)

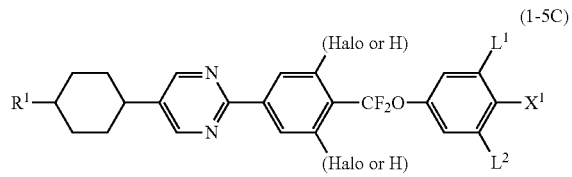
(1-5C)

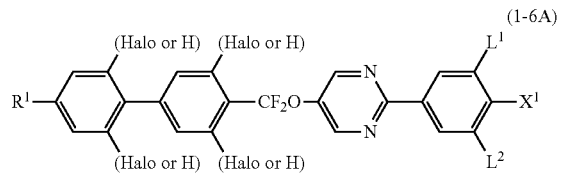
(1-6A)

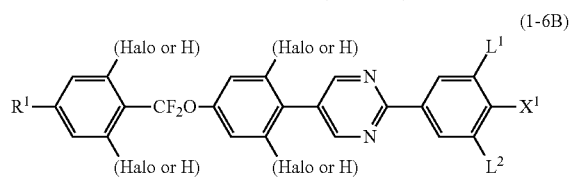
(1-6B)

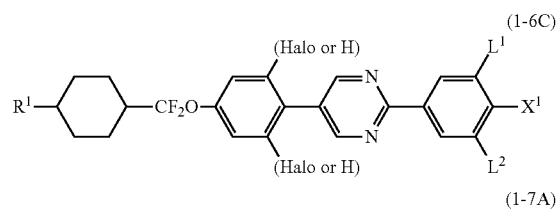
(1-6C)

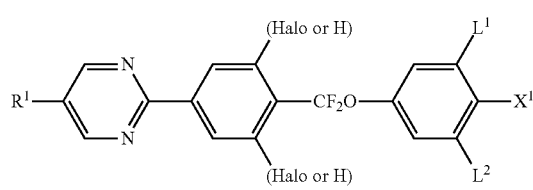
(1-7A)

(in the formulas, $R^1$ is a chain selected from Formulas (CHN-1), (CHN-2), (CHN-4), and (CHN-6)-(CHN-8); ring $A^1$ is a ring selected from Formulas (RG-7), (RG-8-1)-(RG-8-5), (RG-10), (RG-13), and (RG-15); and $X^1$ is fluorine, chlorine, —$CF_3$, —$CHF_2$, —$CH_2F$, —$OCF_3$, —$OCHF_2$, or —C≡C—$CF_3$).

1-4 Synthesis of Compound (1)

Next, the synthesis of Compound (1) is described. Compound (1) may be synthesized by a suitable combination of organic synthesis methods. The methods for introducing target terminal groups, rings, and bonding groups into a starting compound are described in, for example, *Organic Syntheses*, John Wiley & Sons, Inc, *Organic Reactions*, John Wiley & Sons, Inc, *Comprehensive Organic Synthesis*, Pergamon Press, New Lectures on Experimental Chemistry (Maruzen).

1-4-1 Methods for Synthesizing Compound (1)

There are many methods for synthesizing the compounds of Formula (1), and they may be synthesized from commercially available reagents, with properly reference to examples in the specification, or documents and books. Hereafter, a preferred synthesis sequence of representative compounds (of General Formula (112) is disclosed.

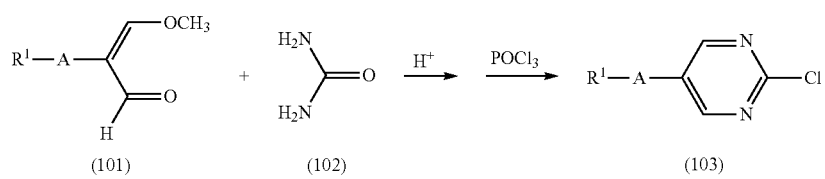

-continued

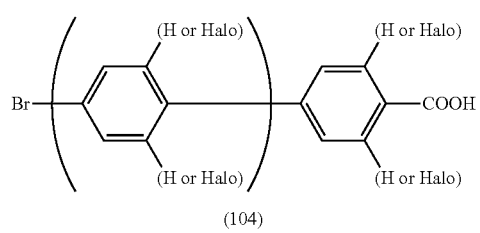
(104)

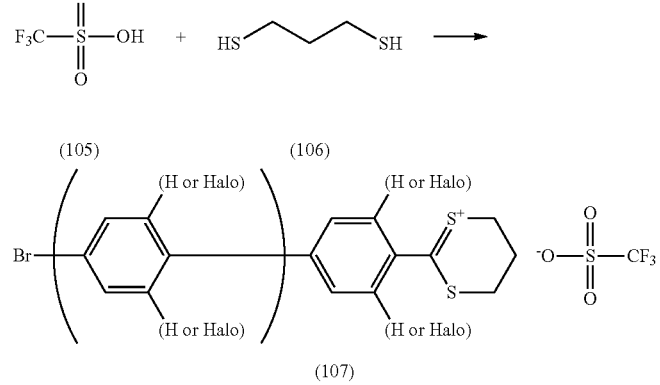
(105) (106)
(107)

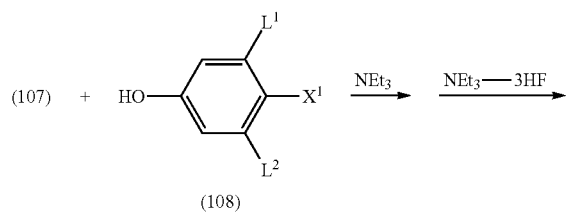
(108)

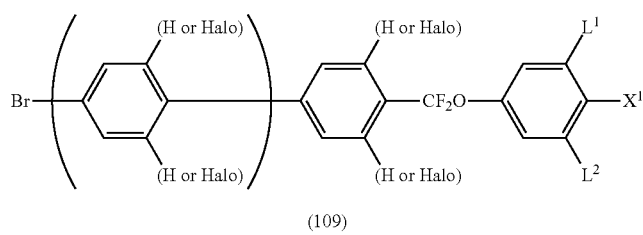
(109)

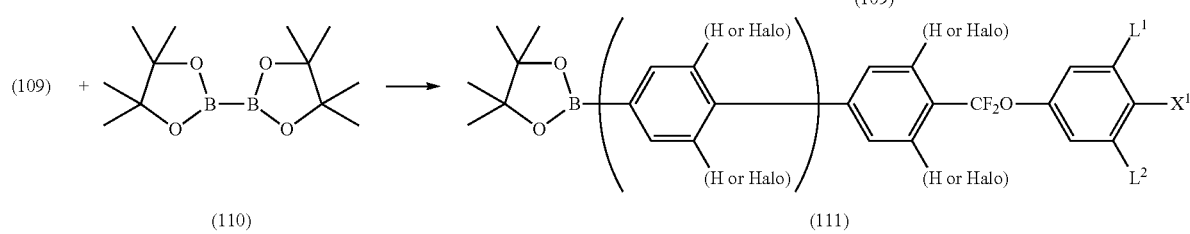
(110) (111)

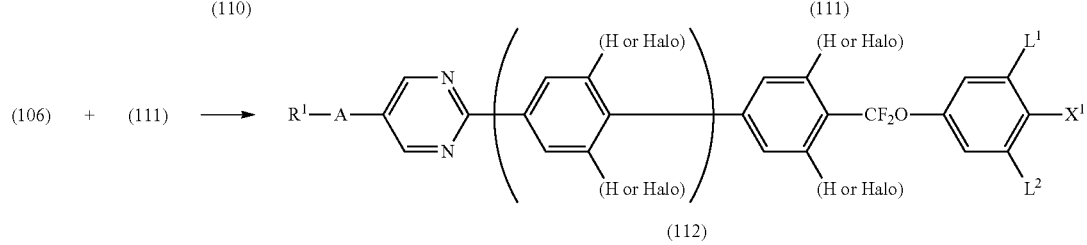
(106) + (111) →
(112)

(in the formula, A represents:

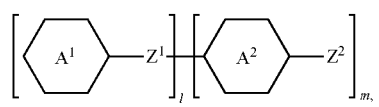

$A^1$, $A^2$, $Z^1$, $Z^2$, l, and m have the same meaning as described above, $R^1$, $L^1$, $L^2$, $X^1$, and (H or Halo) have the same meaning as described above).

Under acidic conditions, a compound of Formula (101) is reacted with urea, and the resultant is reacted with a chloride reagent such as phosphoryl chloride, to obtain a compound of Formula (103). In Formula (103), l and m in A both are 0, and $R^1$ is an alkyl, and the compound is commercially available depending on the length of the alkyl chain. According to the methods recorded in Journal of Fluorine Chemistry 112 (2001) (P73-81) and Japanese Patent Publication No. 2003-525286, Compound (104) is reacted with 1,3-dimercaptopropane and triflic acid, to obtain Compound (107). A mixture of Compound (108) and trimethylamine is dropped into Compound (107), which are reacted with triethylamine tris(hydrogen fluoride) at a low temperature and then treated with bromine, to obtain Compound (109). Compound (109) and Compound (110) are reacted in presence of a catalyst such as tetrakistriphenylphosphine, to obtain Compound (111).

Compound (103) and Compound (111) are reacted in presence of a catalyst such as tetrakistriphenylphosphine, to obtain Compound (112).

2 Compounds (2)-(13)

A second aspect of the present invention is a liquid crystal composition, obtained by adding a component selected from the Components B, C, D, and E shown below into the compound of Formula (1) (i.e., Component A). Compared with a composition containing Component A alone, the liquid crystal composition may be freely adjusted for the driving voltage, the temperature range of a liquid crystal phase, the optical anisotropy value, the dielectric anisotropy value, and viscosity.

The component to be added into the Component A is preferably obtained by mixing Component B, C, or D, where Component B contains at least one compound selected from the group consisting of Formulas (2), (3), and (4), Component C contains at least one compound selected from the group consisting of Formula (5), and Component D contains at least one compound selected from the group consisting of Formulas (6), (7), (8), (9), and (10).

Moreover, by mixing Component E containing at least one compound selected from the group consisting of Formulas (11), (12), and (13), the threshold voltage, the temperature range of a liquid crystal phase, the optical anisotropy value, the dielectric anisotropy value, and the viscosity may be adjusted.

Moreover, for each component of the liquid crystal composition used in the present invention, an analogue containing isotopes of each element may be used due to the small difference in physical properties.

In Component B above, preferred examples of the compound of Formula (2) are Formulas (2-1)-(2-16), preferred examples for the compound of Formula (3) are Formulas (3-1)-(3-112), and preferred examples for the compound of Formula (4) are Formulas (4-1)-(4-52).

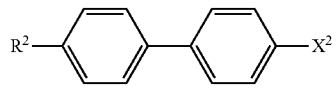

(2-1)

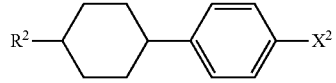

(2-2)

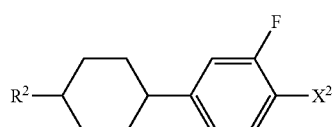

(2-3)

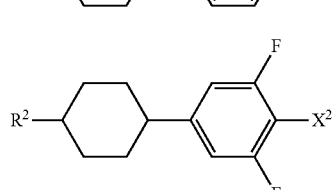

(2-4)

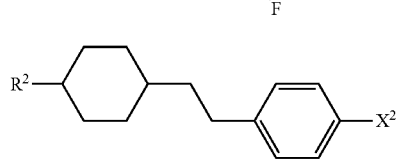

(2-5)

-continued

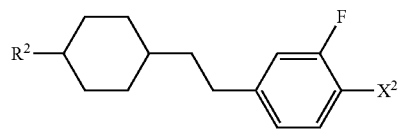

(2-6)

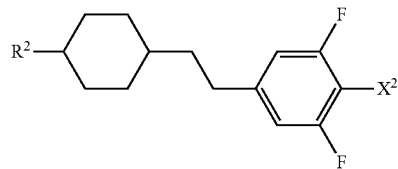

(2-7)

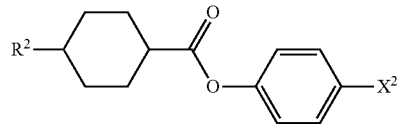

(2-8)

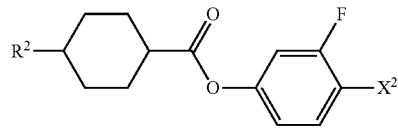

(2-9)

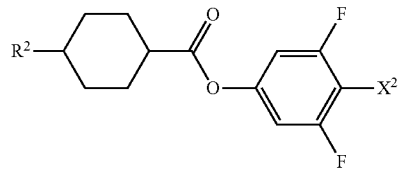

(2-10)

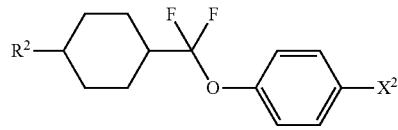

(2-11)

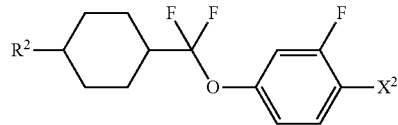

(2-12)

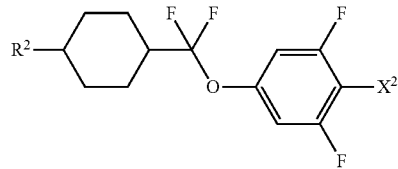

(2-13)

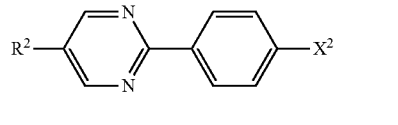

(2-14)

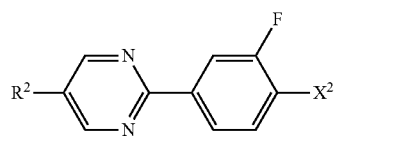

(2-15)

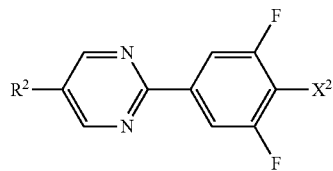
(2-16)
(3-1)
(3-2)
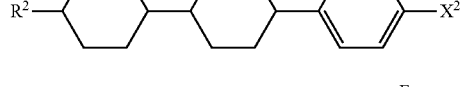
(3-3)
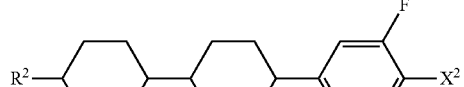
(3-4)
(3-5)
(3-6)
(3-7)
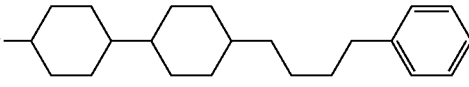
(3-8)
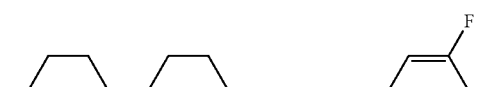
(3-9)
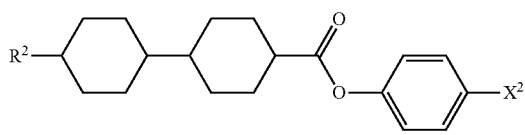
(3-10)
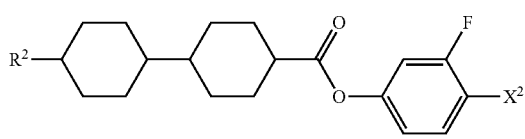
(3-11)
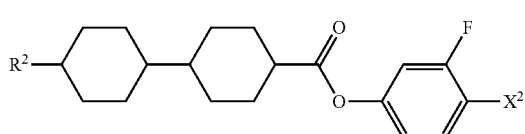
(3-12)
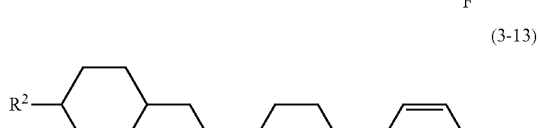
(3-13)
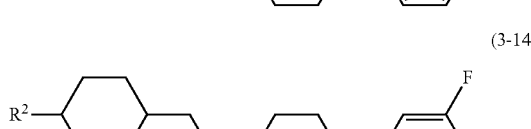
(3-14)
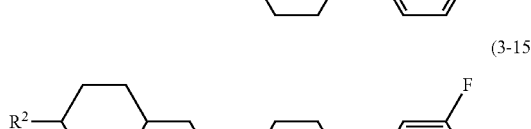
(3-15)
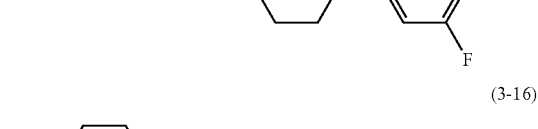
(3-16)
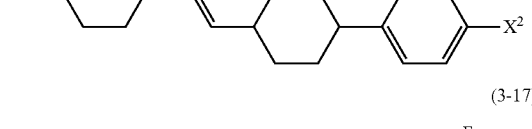
(3-17)
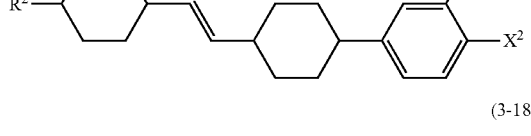
(3-18)

(3-19)
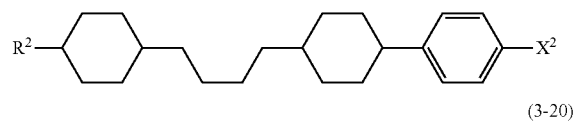
(3-20)
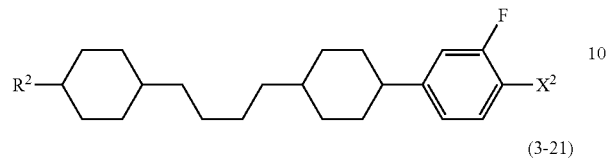
(3-21)
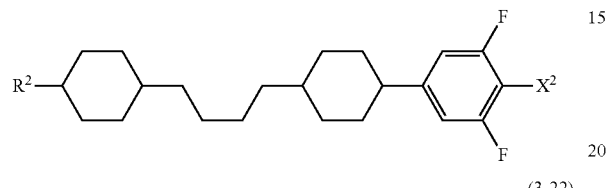
(3-22)
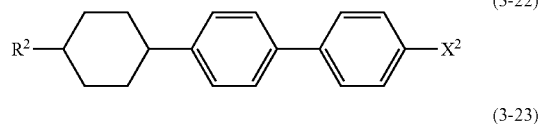
(3-23)
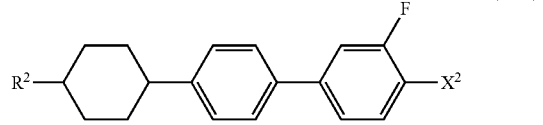
(3-24)
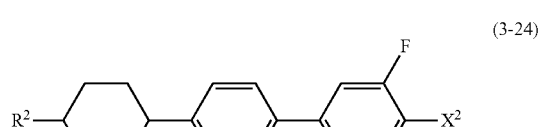
(3-25)
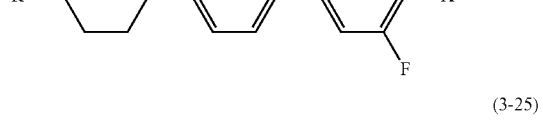
(3-26)
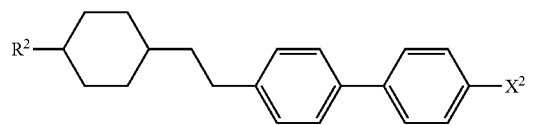
(3-27)
(3-28)
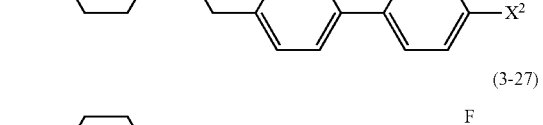
(3-29)
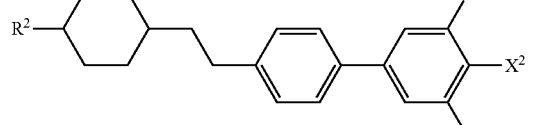
(3-30)
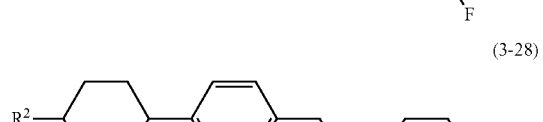
(3-31)
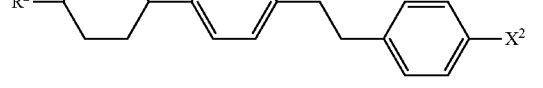
(3-32)
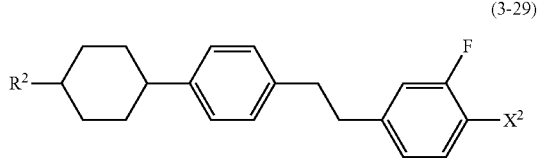
(3-33)
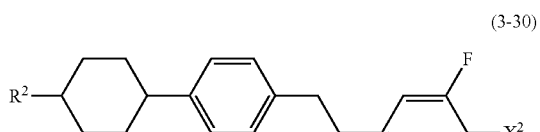
(3-34)
(3-35)
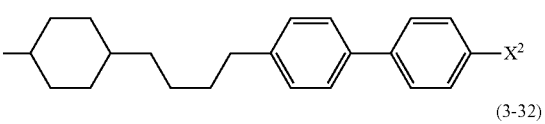
(3-36)
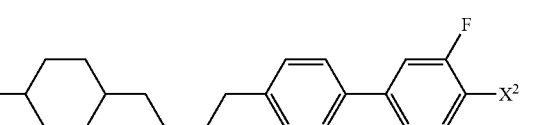
(3-37)
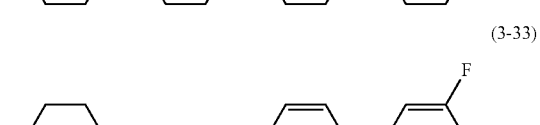
(3-38)
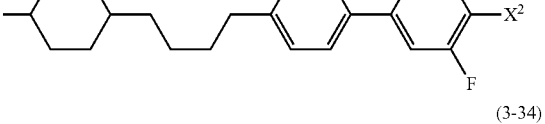

(3-39) 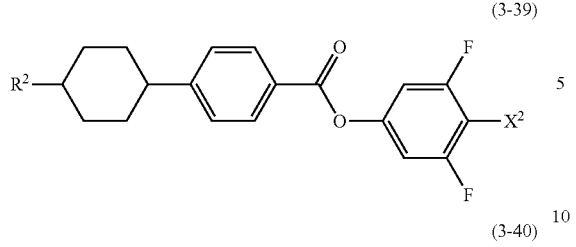
(3-40) 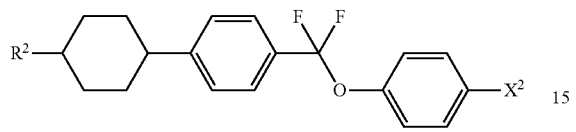
(3-41) 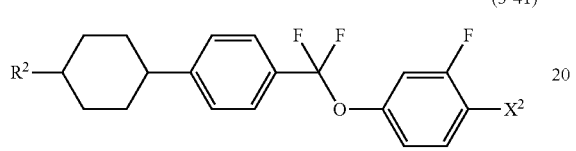
(3-42) 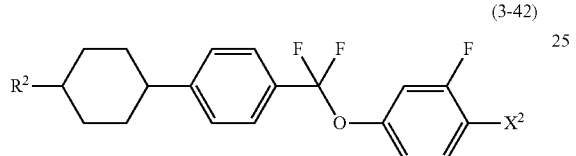
(3-43) 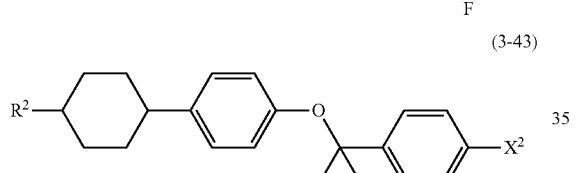
(3-44) 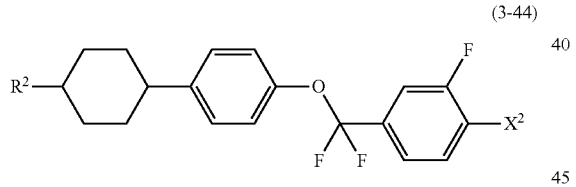
(3-45) 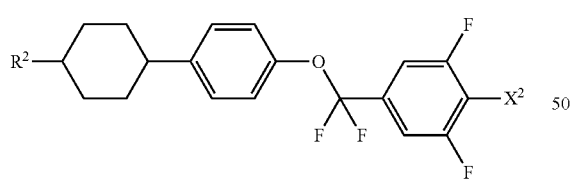
(3-46) 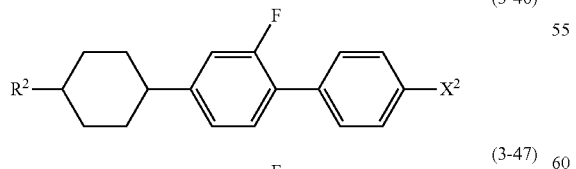
(3-47) 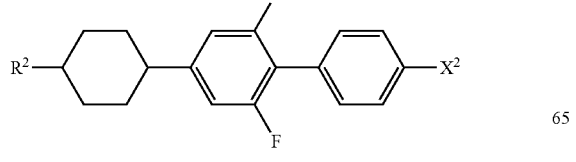
(3-48) 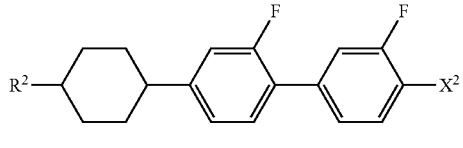
(3-49) 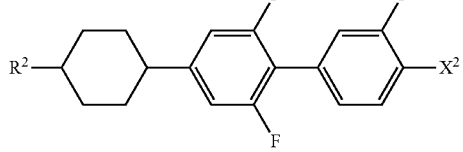
(3-50) 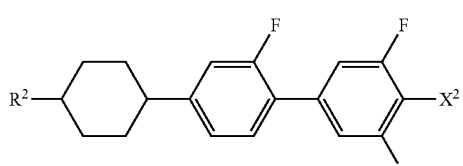
(3-51) 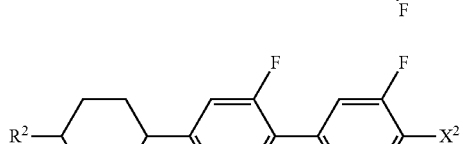
(3-52) 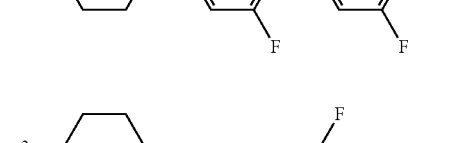
(3-53) 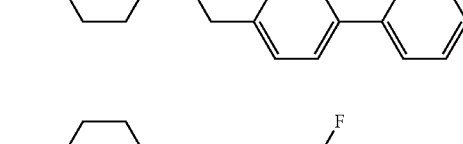
(3-54) 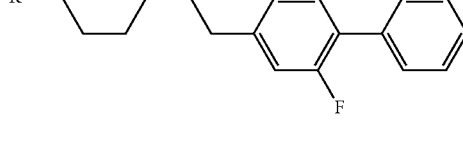
(3-55) 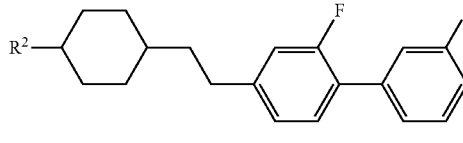
(3-56) 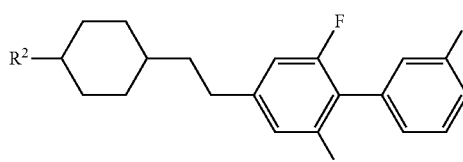

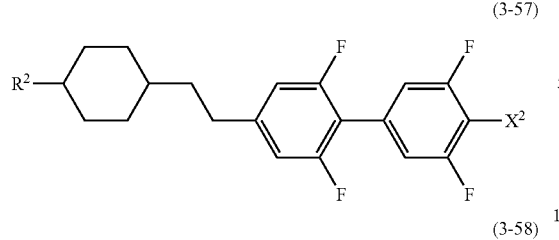
(3-57)
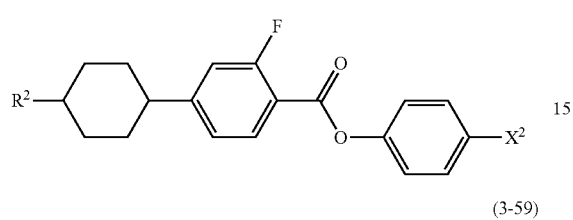
(3-58)
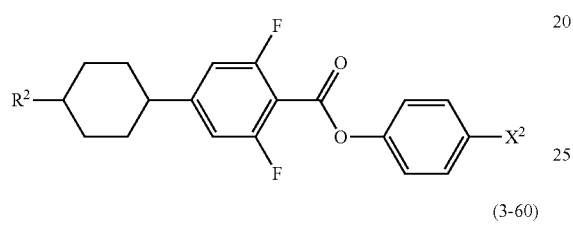
(3-59)
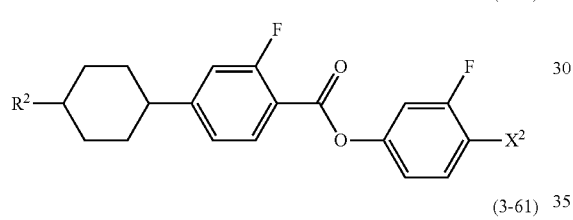
(3-60)
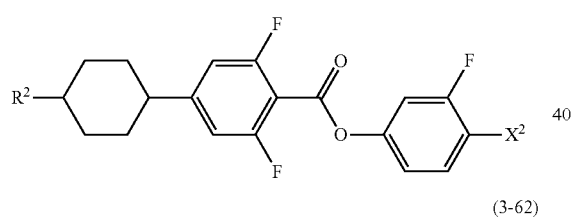
(3-61)
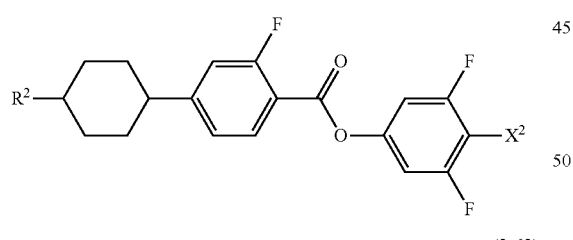
(3-62)
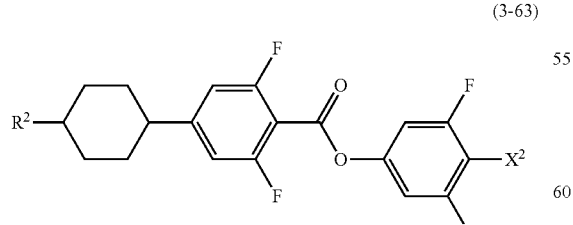
(3-63)
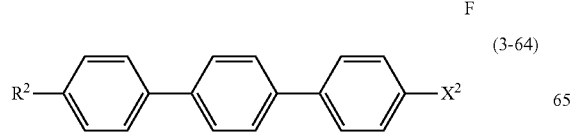
(3-64)
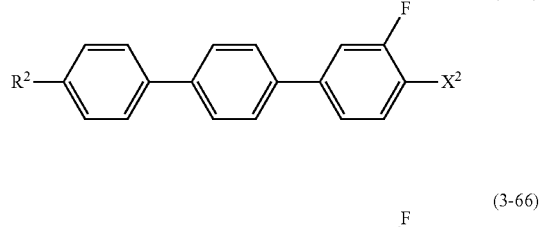
(3-65)
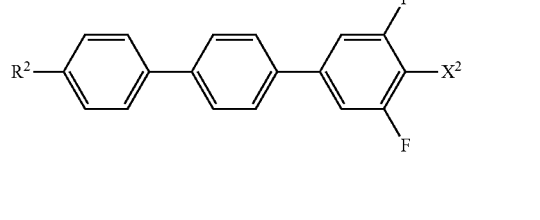
(3-66)
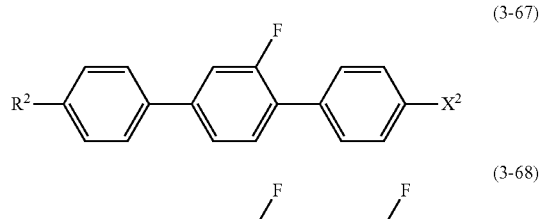
(3-67)
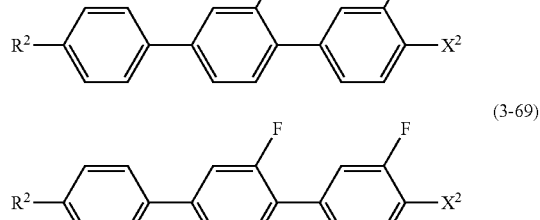
(3-68)
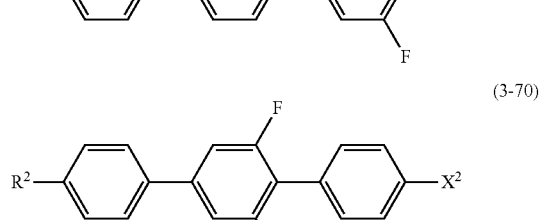
(3-69)
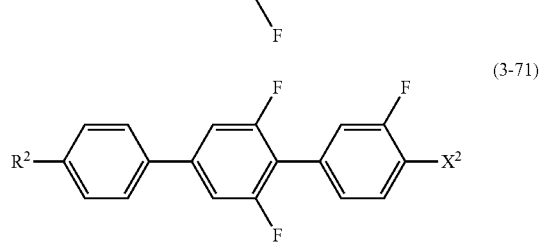
(3-70)
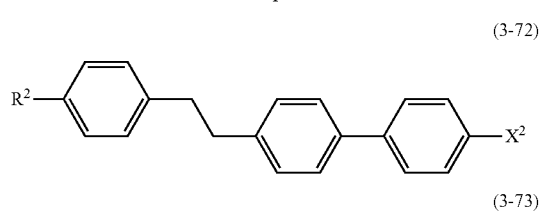
(3-71)
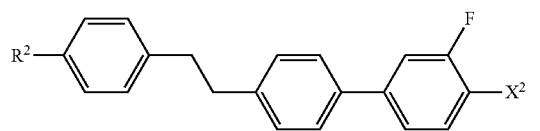
(3-72)
(3-73)

(3-74)
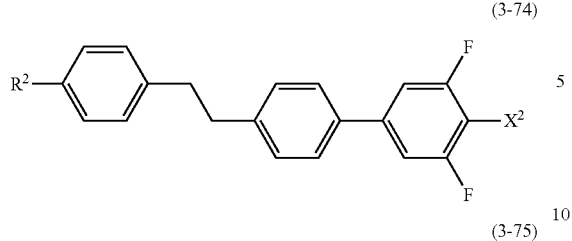
(3-75)
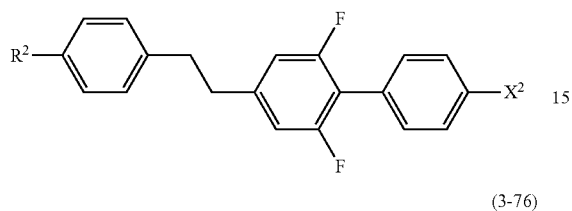
(3-76)
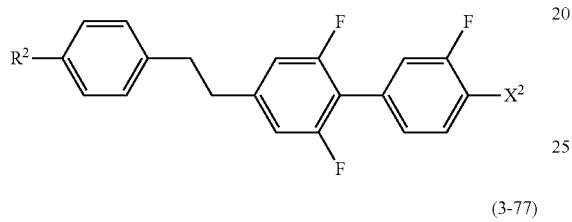
(3-77)
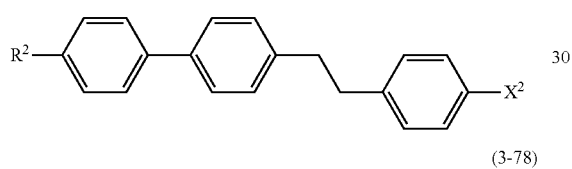
(3-78)
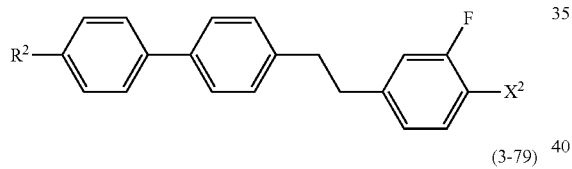
(3-79)
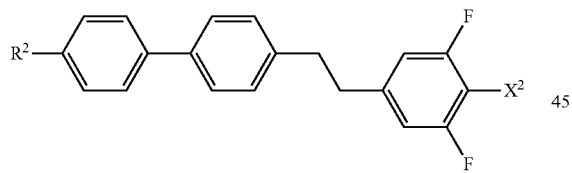
(3-80)
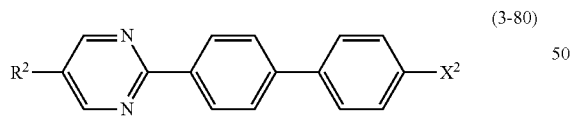
(3-81)
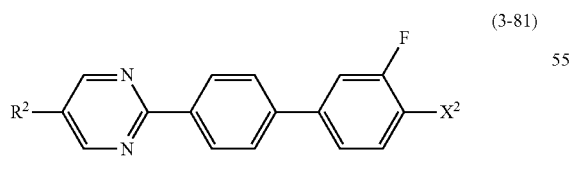
(3-82)
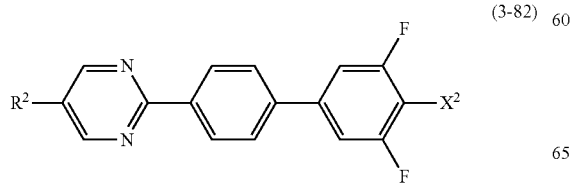
(3-83)
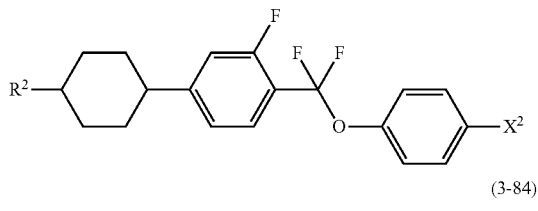
(3-84)
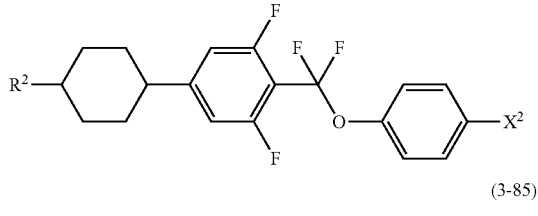
(3-85)
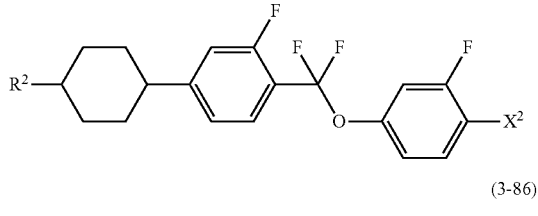
(3-86)
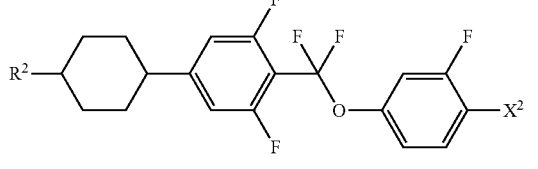
(3-87)
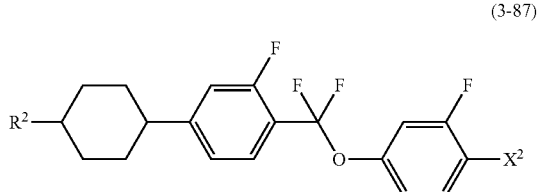
(3-88)
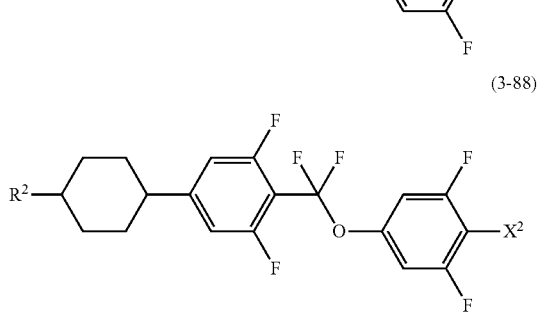
(3-89)
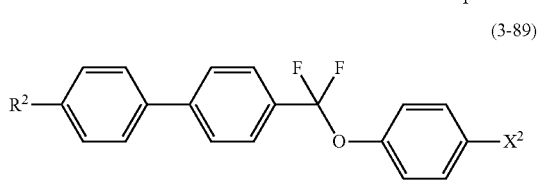
(3-90)

(3-91) 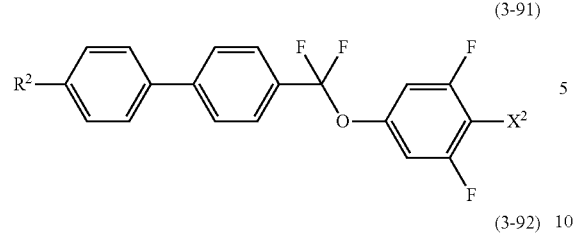
(3-92) 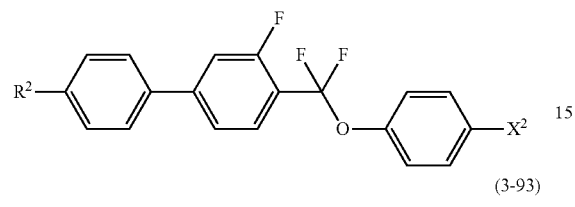
(3-93) 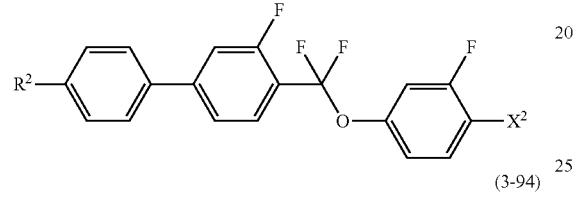
(3-94) 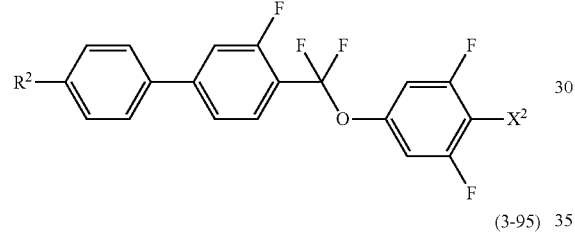
(3-95) 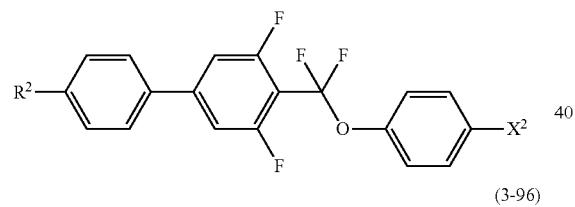
(3-96) 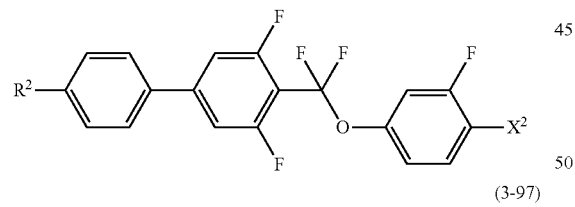
(3-97) 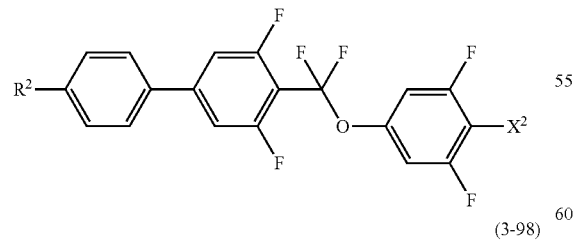
(3-98) 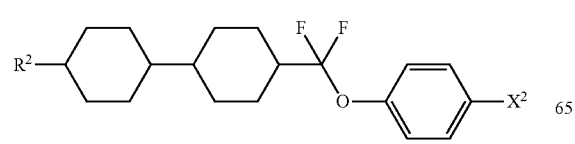
(3-99) 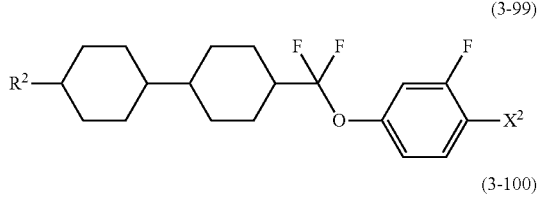
(3-100) 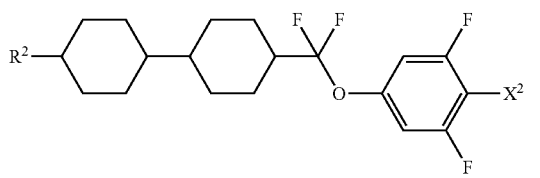
(3-101) 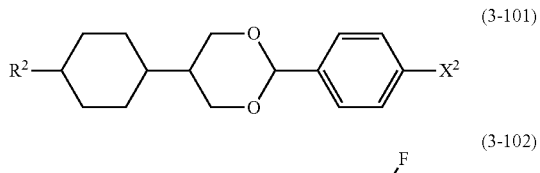
(3-102) 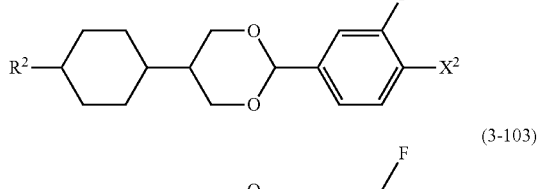
(3-103) 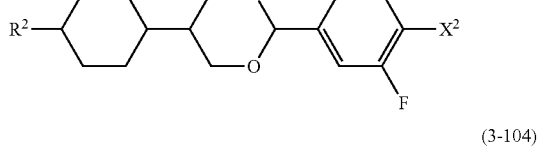
(3-104) 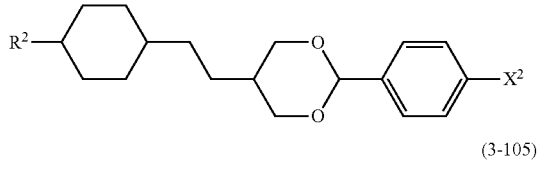
(3-105) 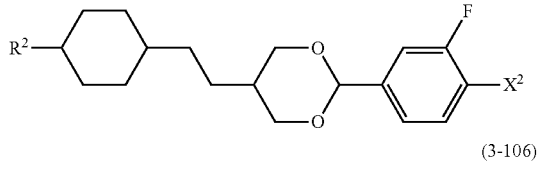
(3-106) 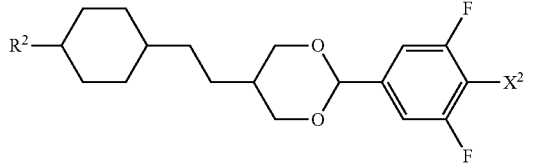
(3-107) 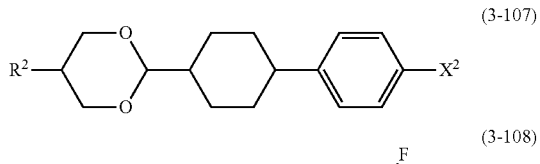
(3-108) 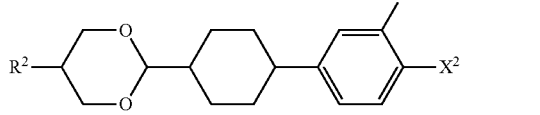

-continued
(3-109)
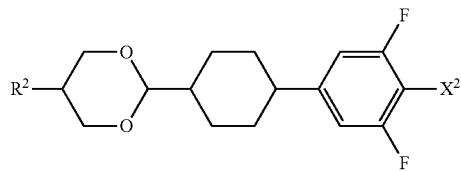
(3-110)
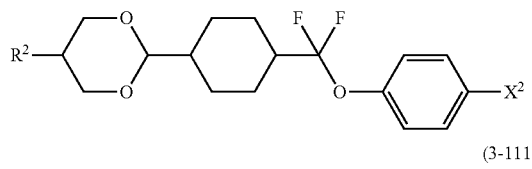
(3-111)
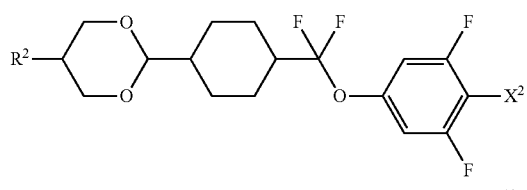
(3-112)
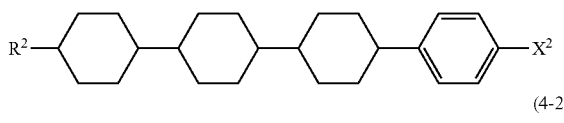
(4-1)
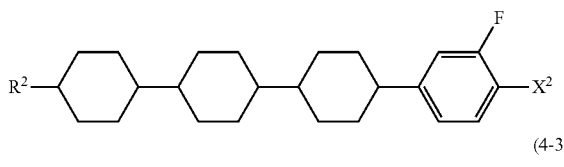
(4-2)
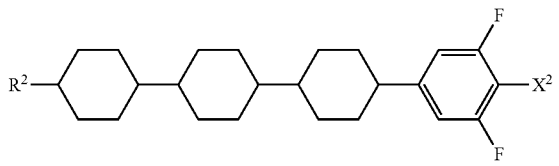
(4-3)
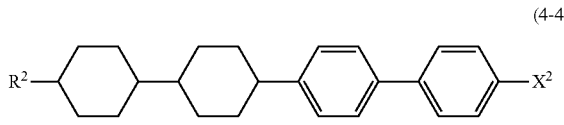
(4-4)
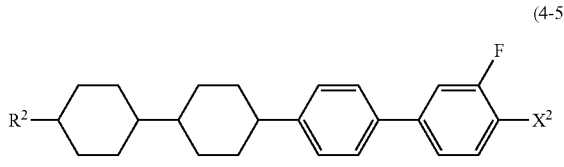
(4-5)
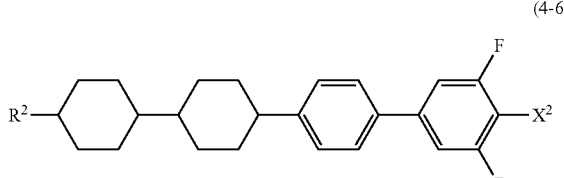
(4-6)
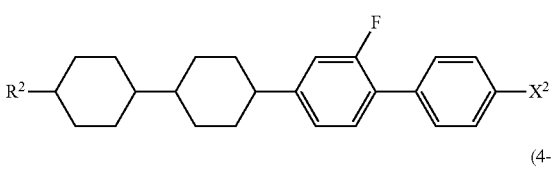
-continued
(4-7)
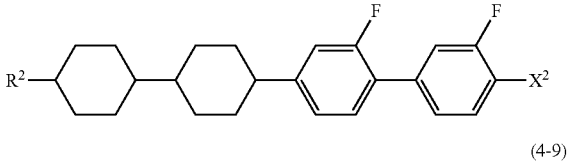
(4-8)
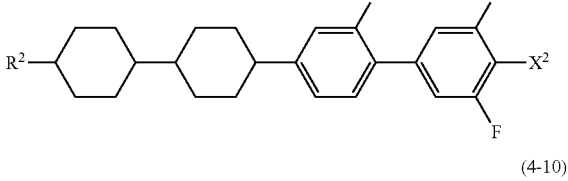
(4-9)
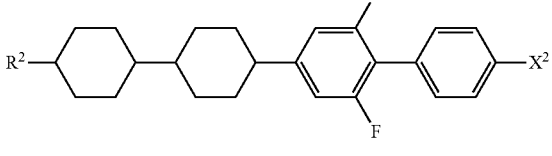
(4-10)
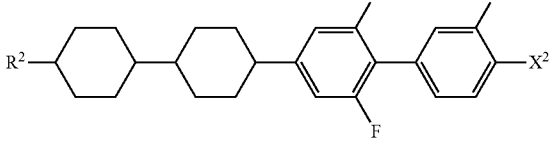
(4-11)
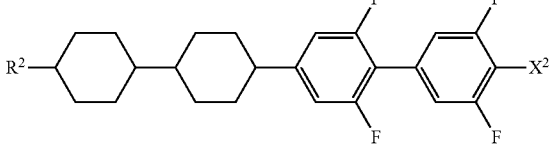
(4-12)
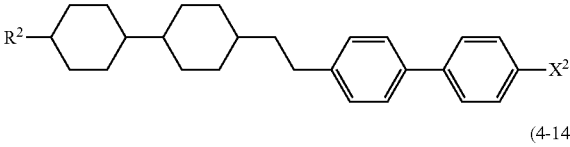
(4-13)
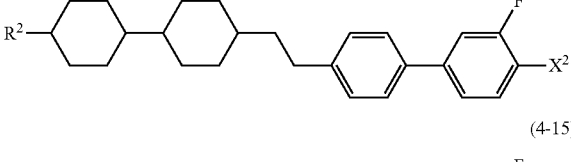
(4-14)
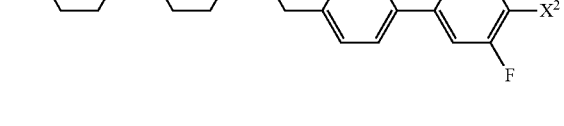
(4-15)

(4-16) 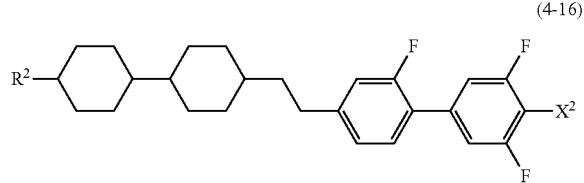
(4-17) 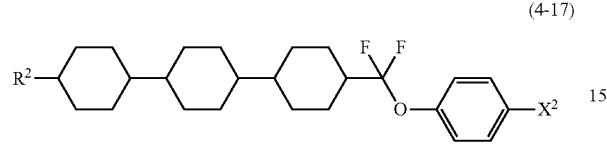
(4-18) 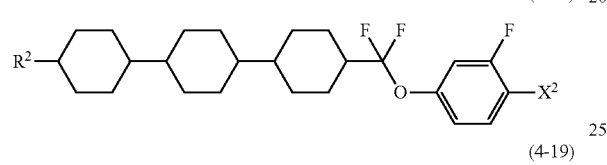
(4-19) 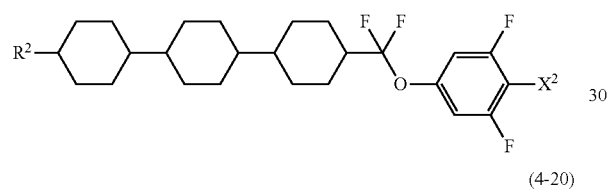
(4-20) 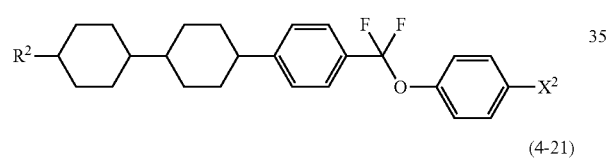
(4-21) 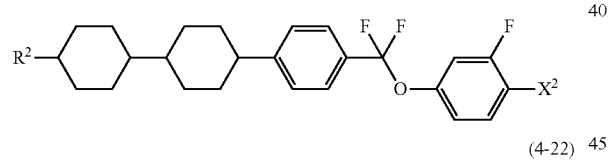
(4-22) 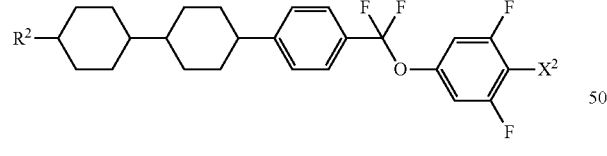
(4-23) 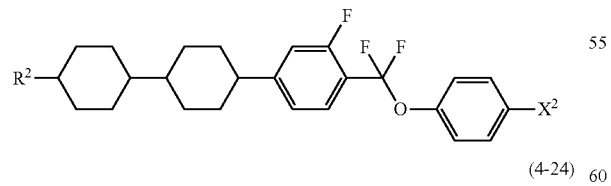
(4-24) 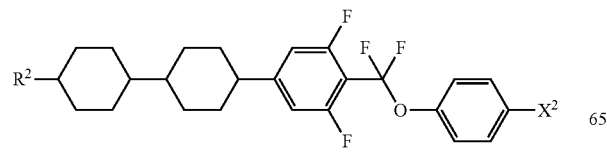
(4-25) 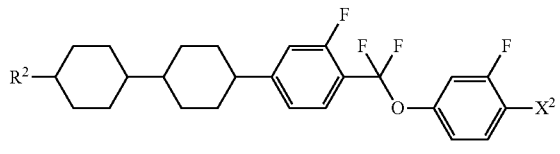
(4-26) 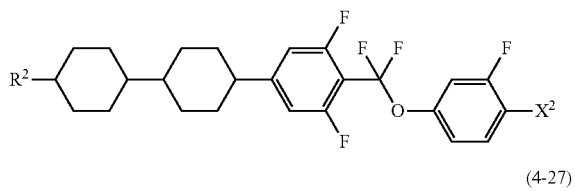
(4-27) 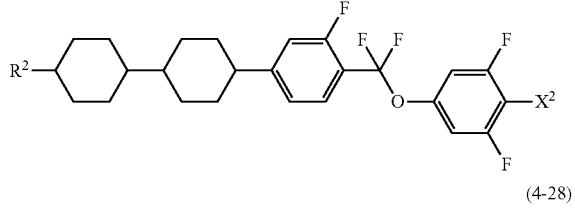
(4-28) 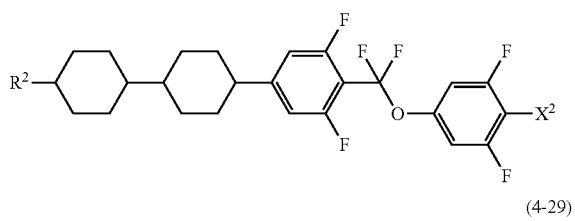
(4-29) 
(4-30) 
(4-31) 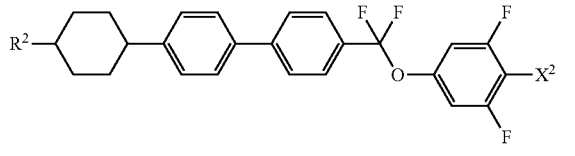
(4-32) 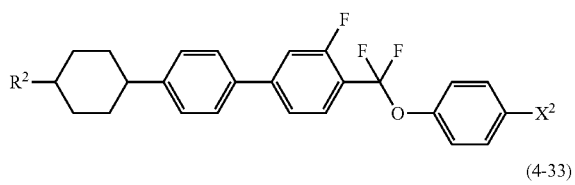
(4-33) 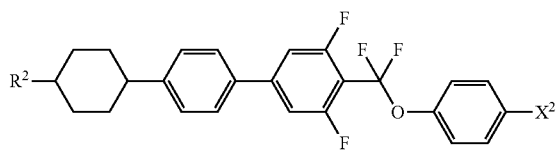

(4-34)
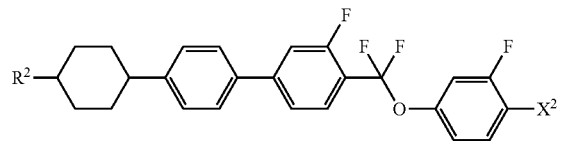
(4-35)
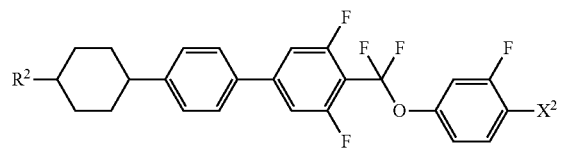
(4-36)
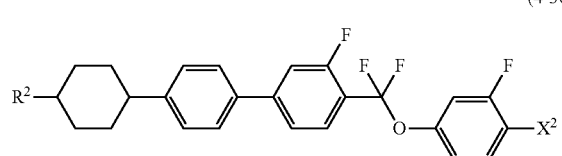
(4-37)
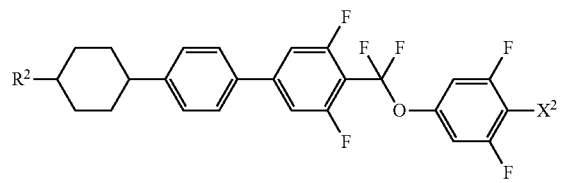
(4-38)
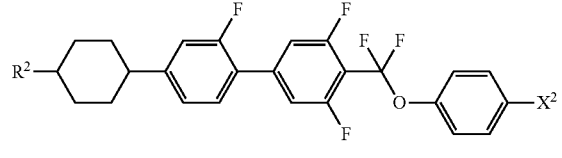
(4-39)
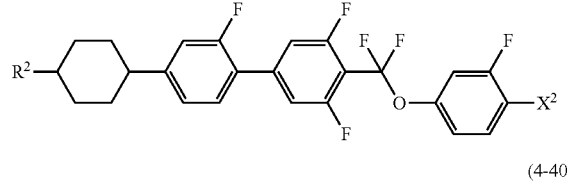
(4-40)
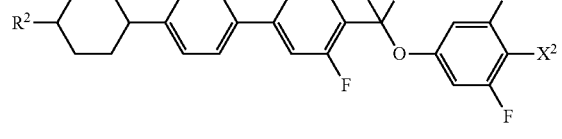
(4-41)
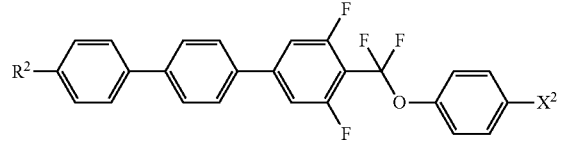
(4-42)
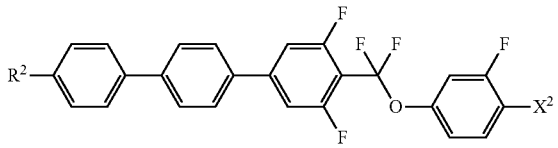
(4-43)
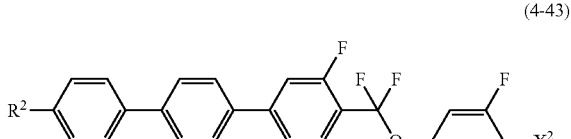
(4-44)
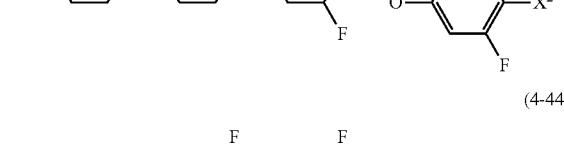
(4-45)
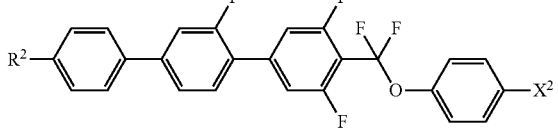
(4-46)
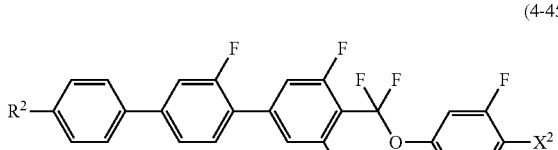
(4-47)
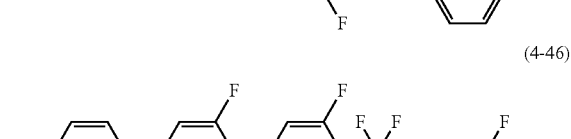
(4-48)
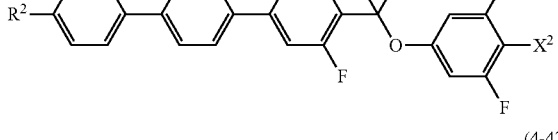
(4-49)
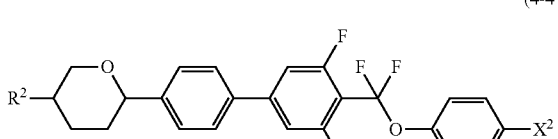

(4-50)

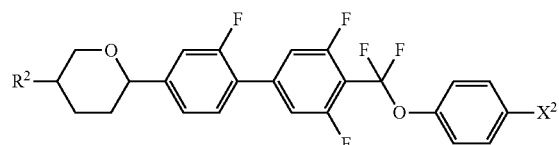

(4-51)

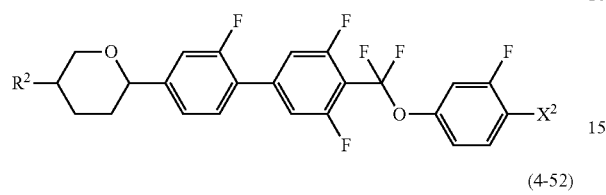

(4-52)

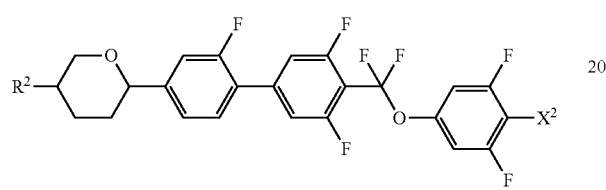

(in the formulas, $R^2$ and $X^2$ have the same meaning as described above)

The compounds of Formulas (2)-(4) (i.e., Component B) have a positive dielectric anisotropy value and excellent thermal or chemical stability, and thus are useful for preparing a liquid crystal composition for TFTs. Based on the total weight of the liquid crystal composition of the present invention, the content of Component B in the liquid crystal composition is suitably in a range of 1 wt %-99 wt %, preferably 10 wt %-97 wt %, and more preferably 40 wt %-95 wt %. Furthermore, by further containing the compound of Formulas (11)-(13) (i.e., Component E), the viscosity may be adjusted.

Preferred examples of the compound of Formula (5) (i.e., Component C) are Formulas (5-1)-(5-62).

(5-1)

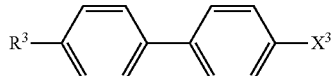

(5-2)

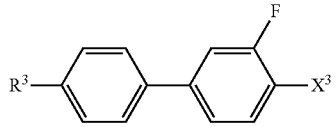

(5-3)

(5-4)

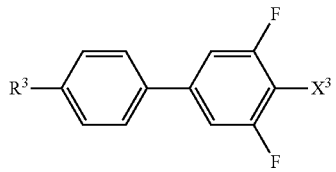

(5-5)

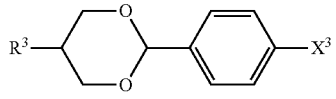

(5-6)

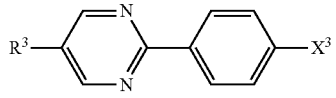

(5-7)

(5-8)

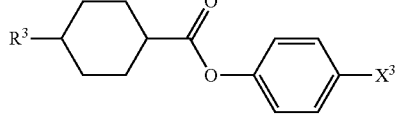

(5-9)

(5-10)

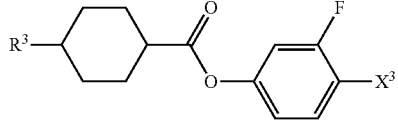

(5-11)

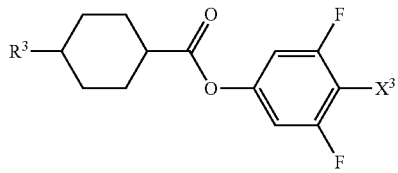

(5-12)

(5-13)

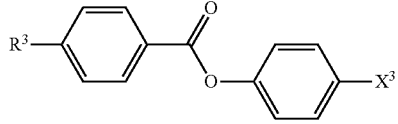

(5-14)

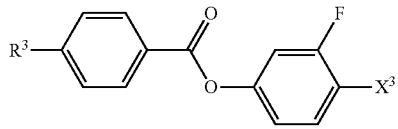

(5-15)

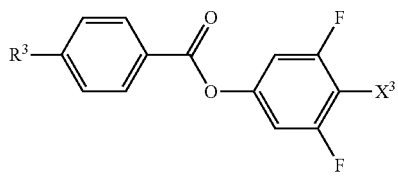

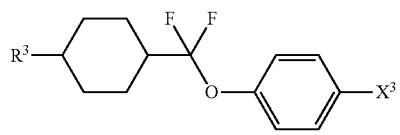 (5-16)
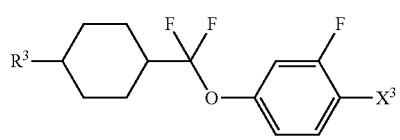 (5-17)
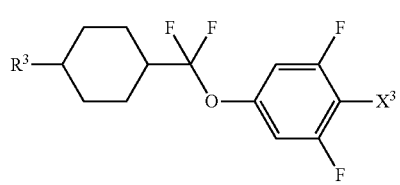 (5-18)
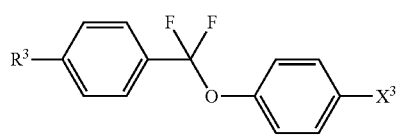 (5-19)
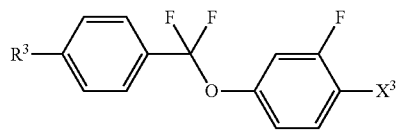 (5-20)
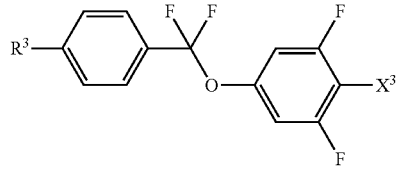 (5-21)
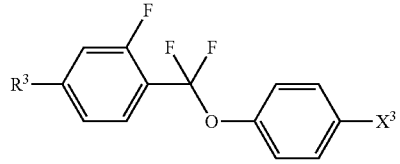 (5-22)
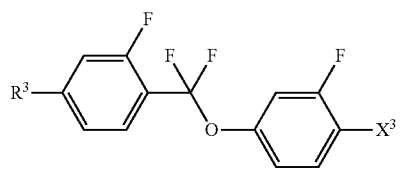 (5-23)
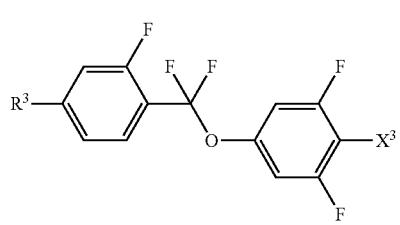 (5-24)
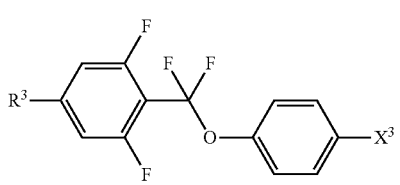 (5-25)
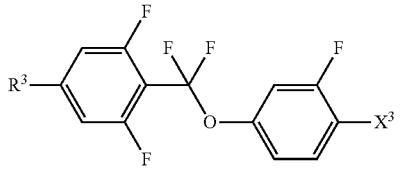 (5-26)
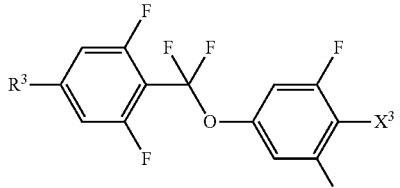 (5-27)
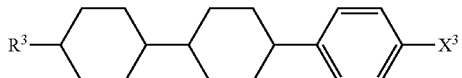 (5-28)
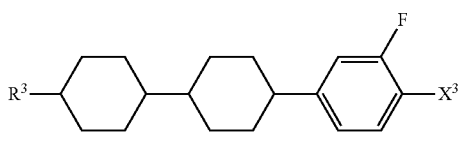 (5-29)
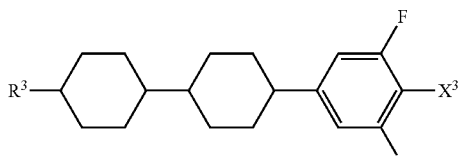 (5-30)
 (5-31)
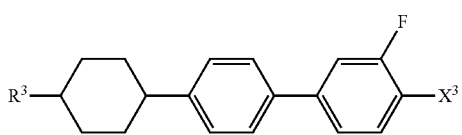 (5-32)
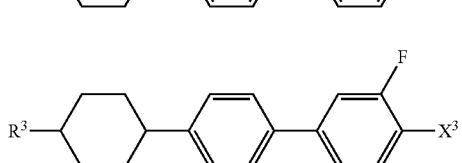 (5-33)
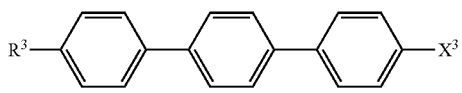 (5-34)

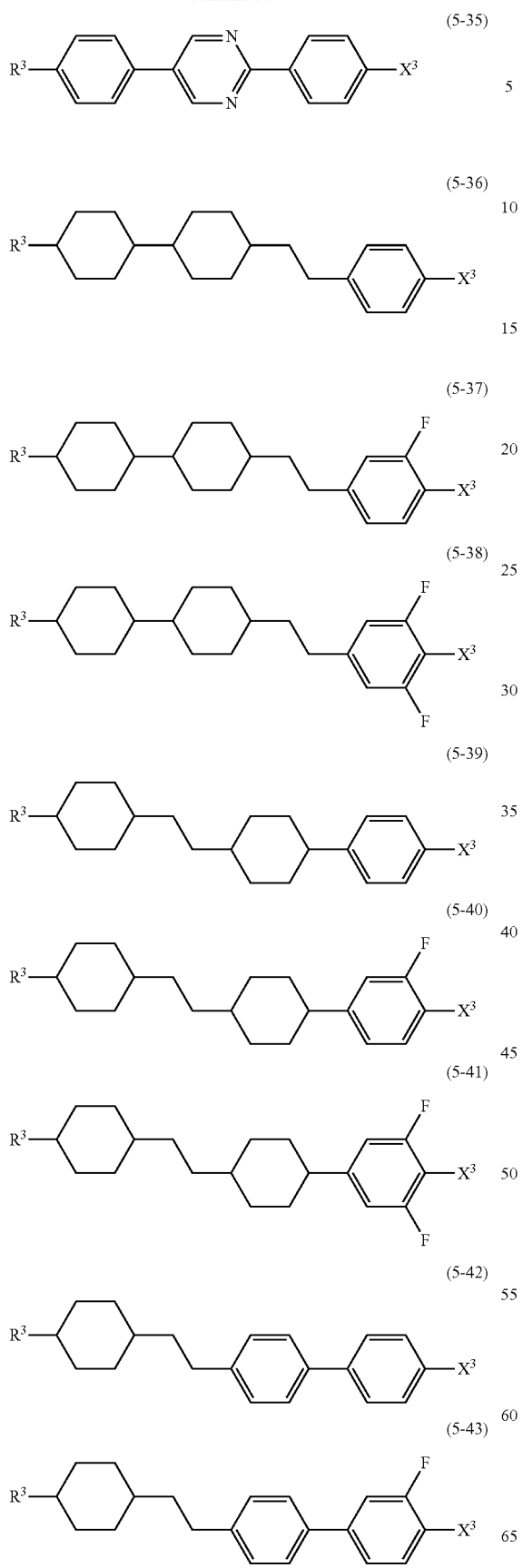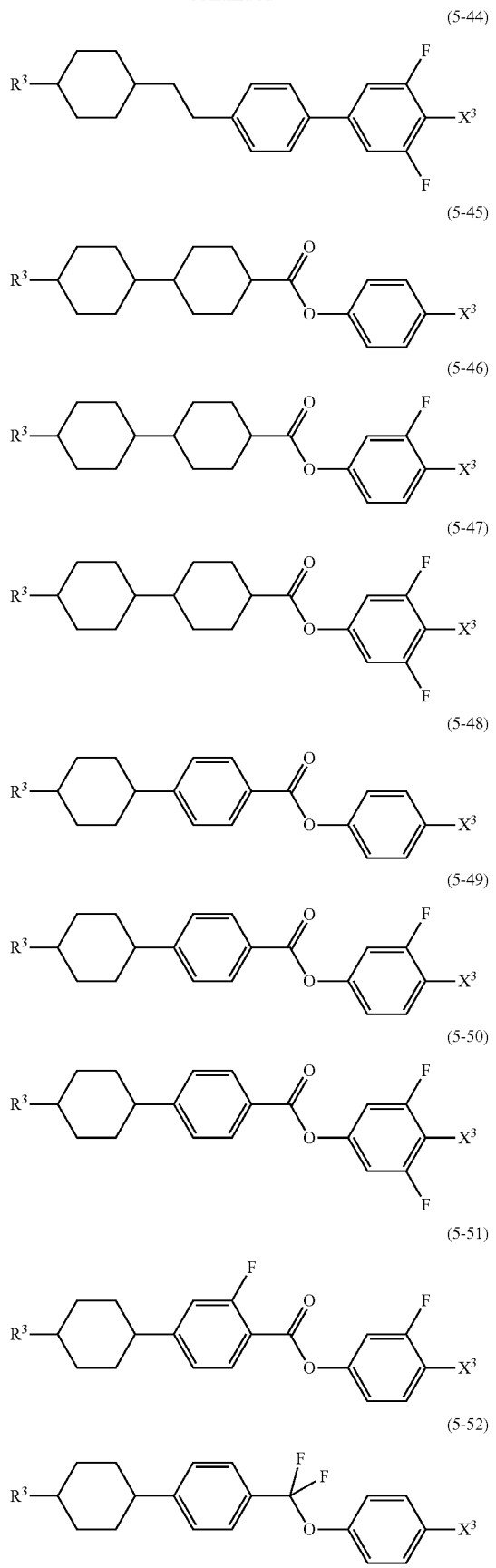

(5-53)
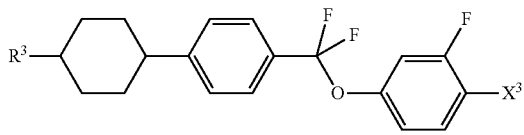

(5-54)

(5-55)
(5-56)
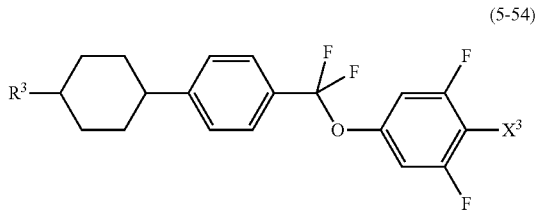

(5-57)
(5-58)
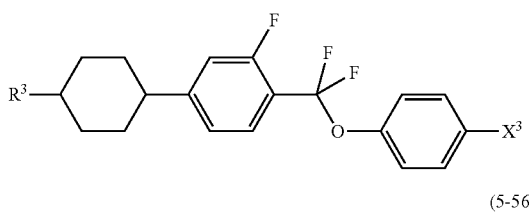

(5-59)
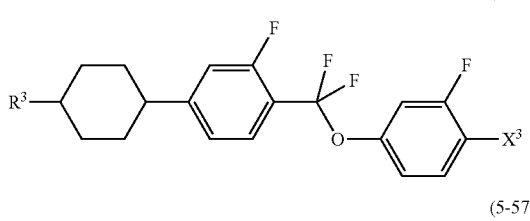

(5-60)
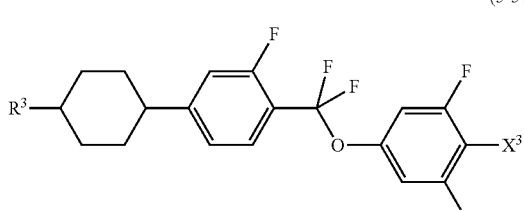

(5-61)
(5-62)
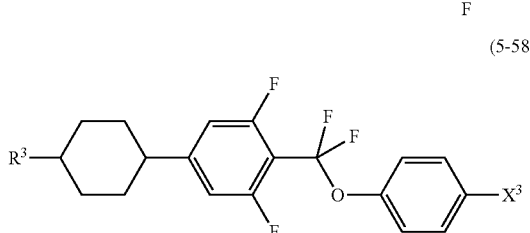

(in the formulas, $R^3$ and $X^3$ have the same meaning as described above)

The compounds of Formula (5) (i.e., Component C) have a positive and very large dielectric anisotropy value. By containing Component C, the driving voltage of the composition is lowered. In addition, the viscosity and optical anisotropy value can be adjusted, and the temperature range of a liquid crystal phase can be expanded.

Based on the total weight of the composition, the content of Component C is preferably 0.1-99.9 wt %, more preferably 10-97 wt %, and still more preferably 40-95 wt %. Furthermore, by mixing the components below, the threshold voltage, the liquid crystal phase temperature range, the optical anisotropy value, dielectric anisotropy value, and the viscosity may be adjusted.

Component D containing at least one compound selected from the group consisting of Formulas (6)-(10) is a preferred component for preparing the liquid crystal composition of the present invention having a negative dielectric anisotropy value.

Preferred examples of the compounds of Formulas (6)-(10) (Component D) are Formulas (6-1)-(6-5), Formulas (7-1)-(7-9), Formulas (8-1)-(8-3), and Formulas (10-1)-(10-11).

(6-1)
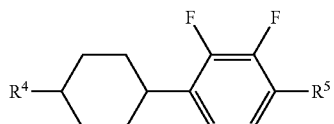

(6-2)
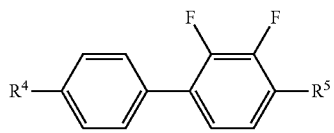

(6-3)
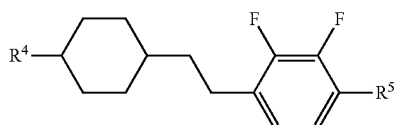

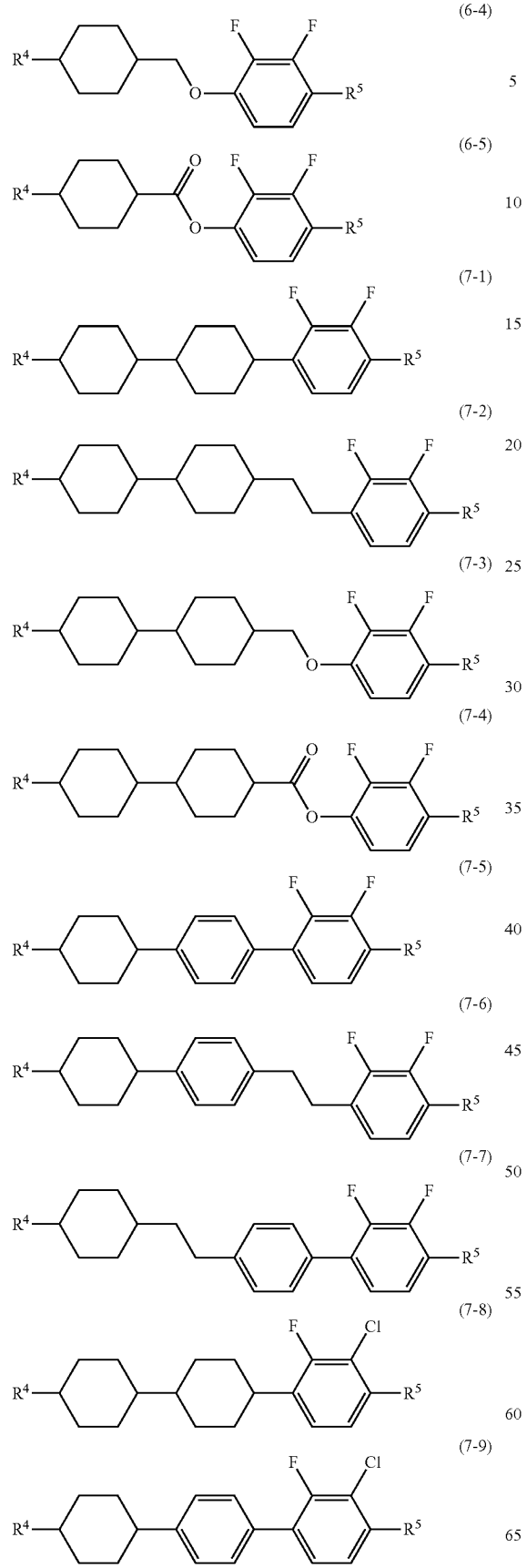
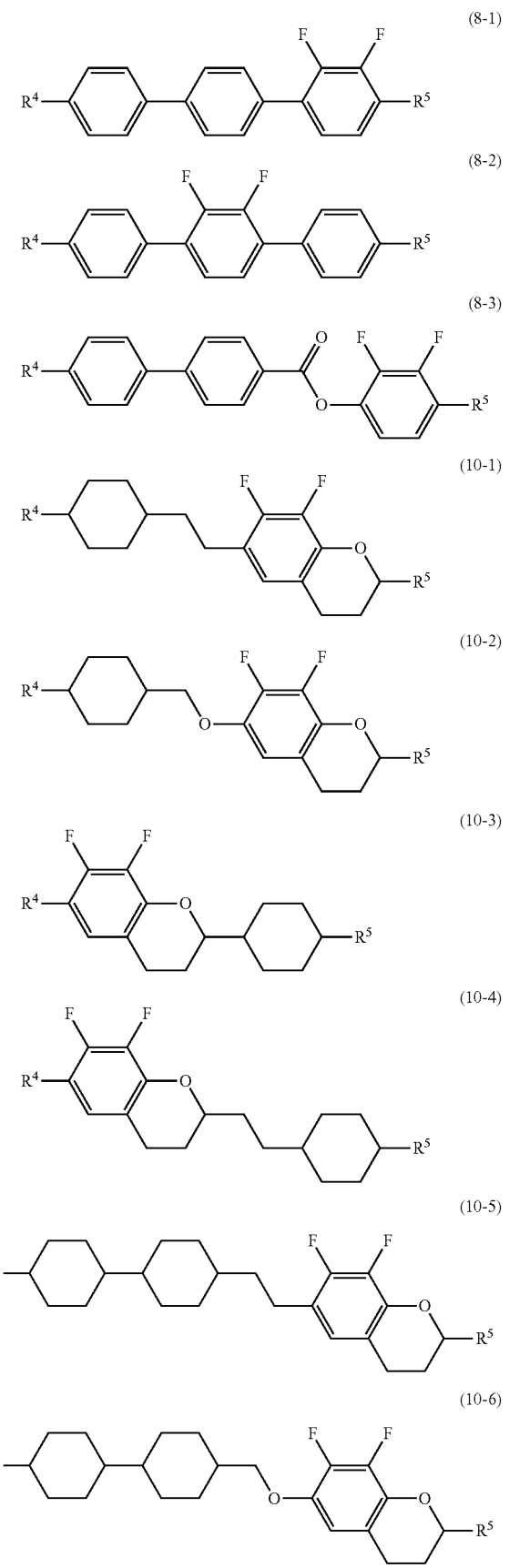

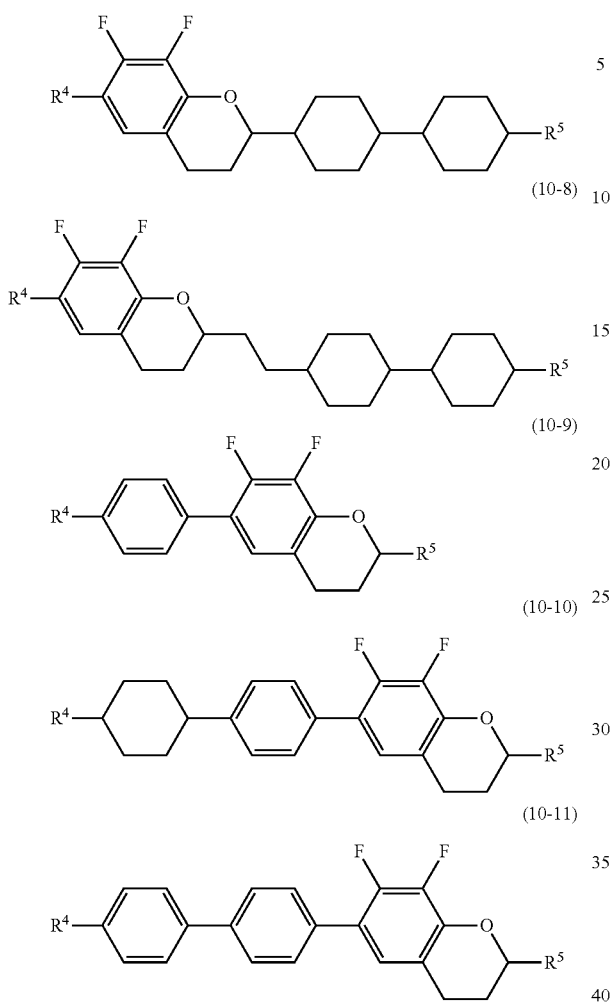

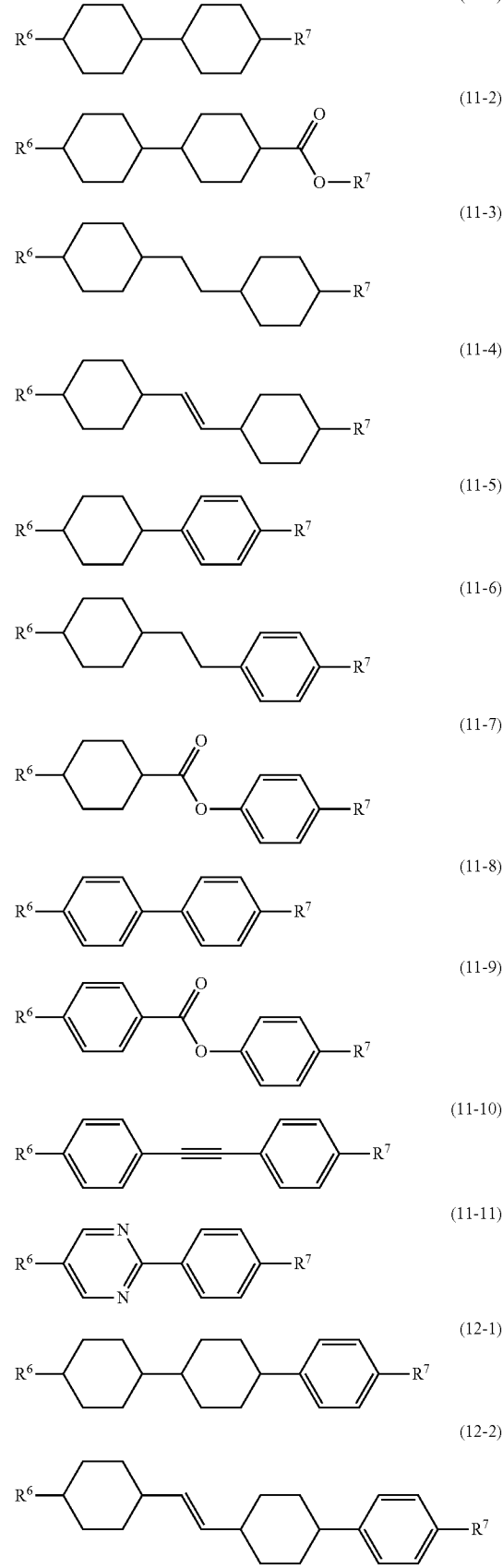

(in the formulas, $R^4$ and $R^5$ have the same meaning as described above)

The compounds of the Component D are mainly used in the liquid crystal compositions having a negative dielectric anisotropy value. In Component D, the compound of Formula (6) is a 2-rings compound, thereby mainly having the effect of adjusting the threshold voltage, the viscosity, or the optical anisotropy value. Furthermore, the compounds of Formulas (7) and (8) are 3-rings compounds, thereby having the effect of increasing the clearing point, expanding the temperature range of an optically isotropic liquid crystal phase, and increasing the optical anisotropy value. The compounds of Formulas (9) and (10) have a negative and large dielectric anisotropy value, thereby mainly having the effect of adjusting the driving voltage.

In preparing a composition having a negative dielectric anisotropy value, the content of Component D is preferably higher than or equal to 40 wt %, and more preferably 50 wt %-95 wt %, based on the total weight of the composition. Furthermore, by mixing Component D, the elastic constant and the voltage-transmittance curve of the composition may be controlled. When mixing Component D into a composition having a positive dielectric anisotropy value, the content of Component D is preferably lower than or equal to 30 wt %, based on the total weight of the composition.

Preferred examples of the compounds of Formulas (11), (12), and (13) (Component E) are Formulas (11-1)-(11-11), Formula (12-1)-(12-18), and Formulas (13-1)-(13-6).

(12-3)
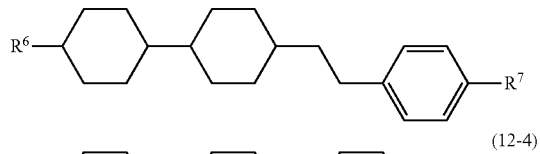
(12-4)
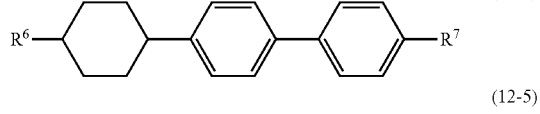
(12-5)
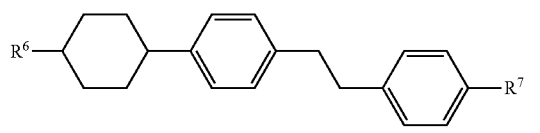
(12-6)
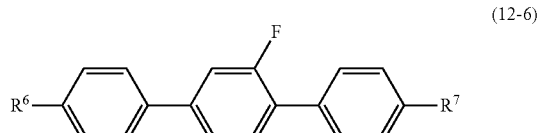
(12-7)
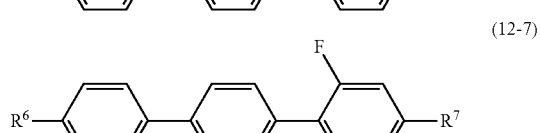
(12-8)
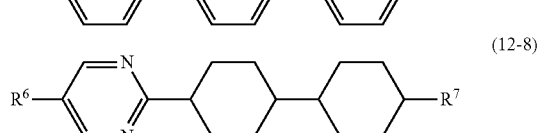
(12-9)
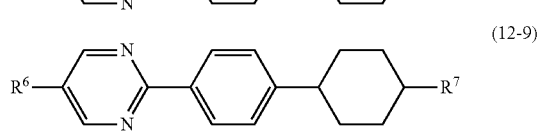
(12-10)
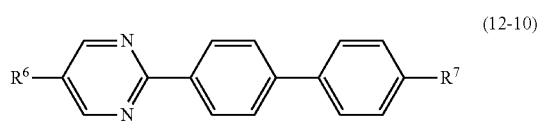
(12-11)
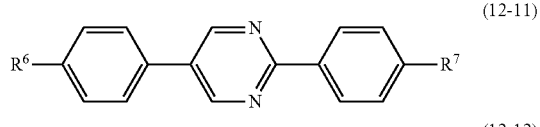
(12-12)
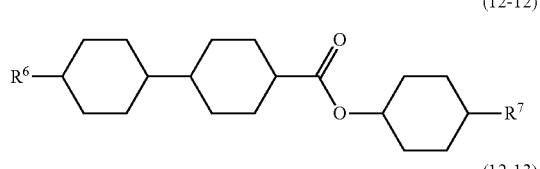
(12-13)
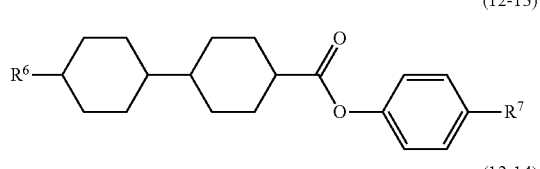
(12-14)
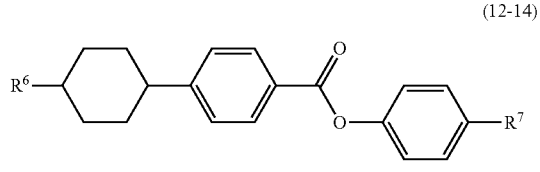
(12-15)
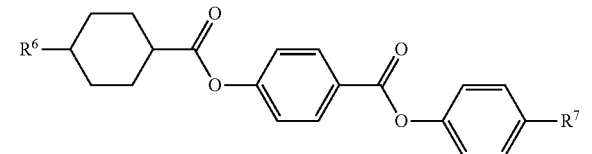
(12-16)
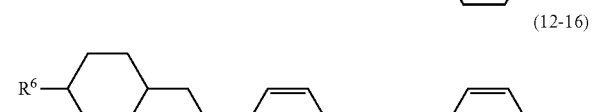
(12-17)
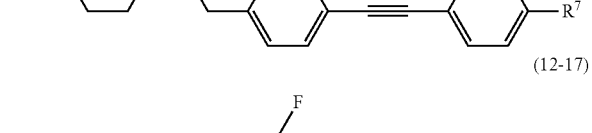
(12-18)
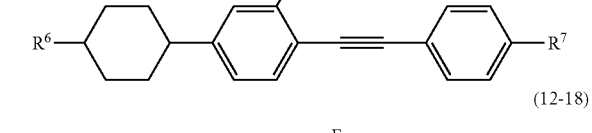
(13-1)
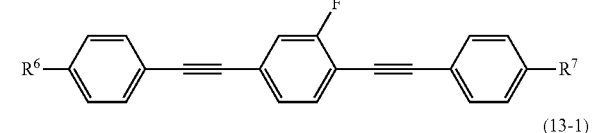
(13-2)
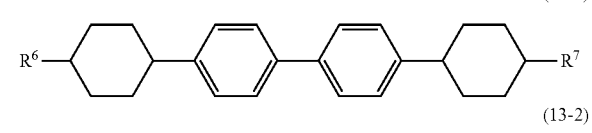
(13-3)
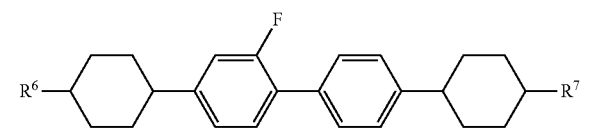
(13-4)
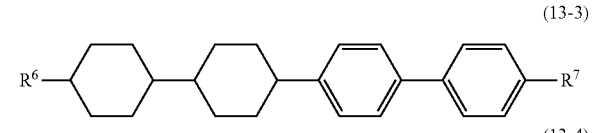
(13-5)
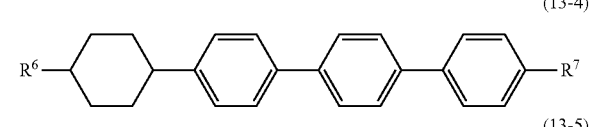
(13-6)
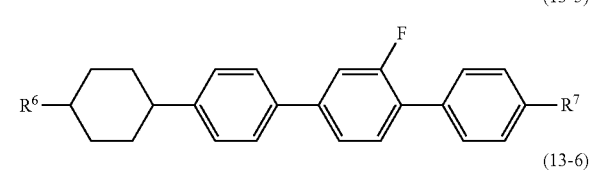
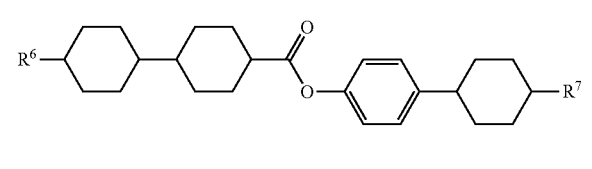
(in the formulas, $R^6$ and $R^7$ have the same meaning as described above)
The compounds of Formulas (11)-(13) (Component E) are compounds having a low absolute value of dielectric anisotropy, and are nearly neutral. The compounds of Formula (11) mainly have the effect of adjusting the viscosity or the optical anisotropy value. Furthermore, the compounds of Formulas

(12) and (13) have the effect of increasing the clearing point and expanding the temperature range of an optically isotropic liquid crystal phase, or the effect of adjusting the optical anisotropy value.

If the content of the compounds of Component E is increased, the driving voltage of the liquid crystal composition is raised, and the viscosity is lowered. Therefore, the content of the compounds of Component E is expected to be as high as possible, provided that the desired driving voltage of the liquid crystal composition may be met. In preparing a liquid crystal composition for a TFT, the content of Component E is preferably 60 wt % or less, and more preferably 40 wt % or less, based on the total weight of the composition.

The liquid crystal composition of the present invention contains 0.1 wt %-99 wt % of at least one compound of Formula (1), which is benefit to the exhibition of excellent properties.

The liquid crystal composition of the present invention is prepared by a well-known method, for example, a process in which essential components are dissolved at a high temperature.

3 Compounds (15)-(19)

A third aspect of the present invention is a liquid crystal composition obtained by adding a component selected from Components F and G below into Component A.

The component to be added into Component A is preferably obtained by mixing Component F or G, where Component F contains at least one compound selected from the group consisting of Formulas (15), (16), (17), and (18), and Component G contains at least one compound selected from the group consisting of Formula (19).

Moreover, for each component of the liquid crystal composition of the present invention, an analogue containing isotopes of each element also can be used due to the small difference in physical properties.

In Component F, preferred example of the compounds of Formula (15) are Formulas (15-1)-(15-8), preferred examples of the compounds of Formula (16) are Formulas (16-1)-(16-26), and preferred examples of the compounds of Formula (17) are Formula (17-1)-(17-22).

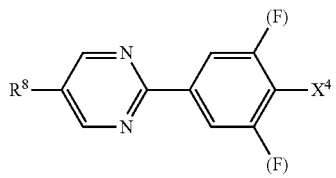

(15-1)

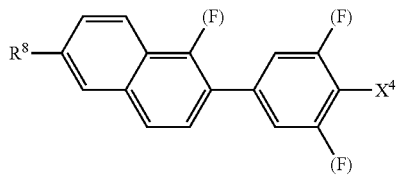

(15-2)

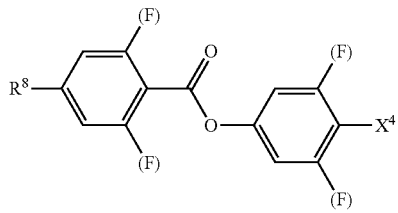

(15-3)

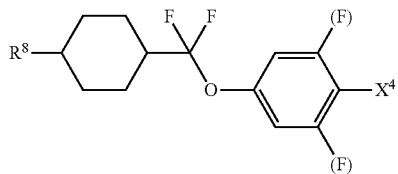

(15-4)

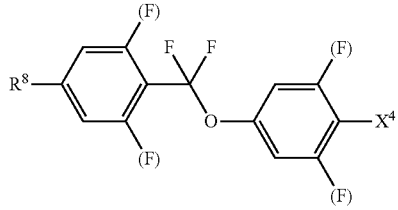

(15-5)

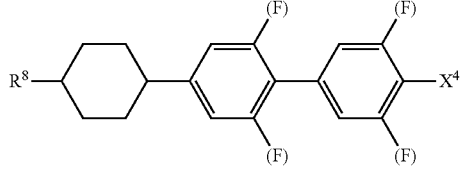

(15-6)

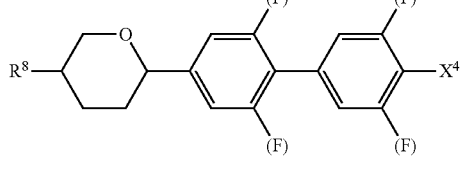

(15-7)

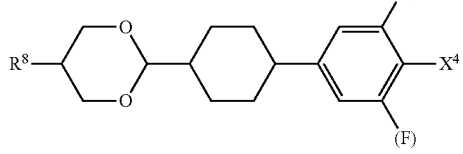

(15-8)

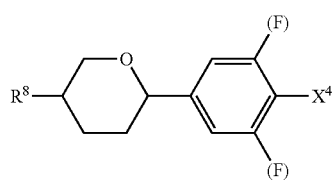

(16-1)

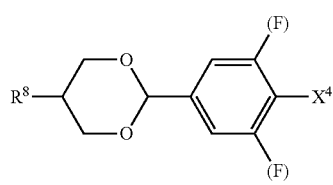

(16-2)

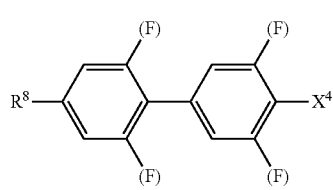

(16-3)

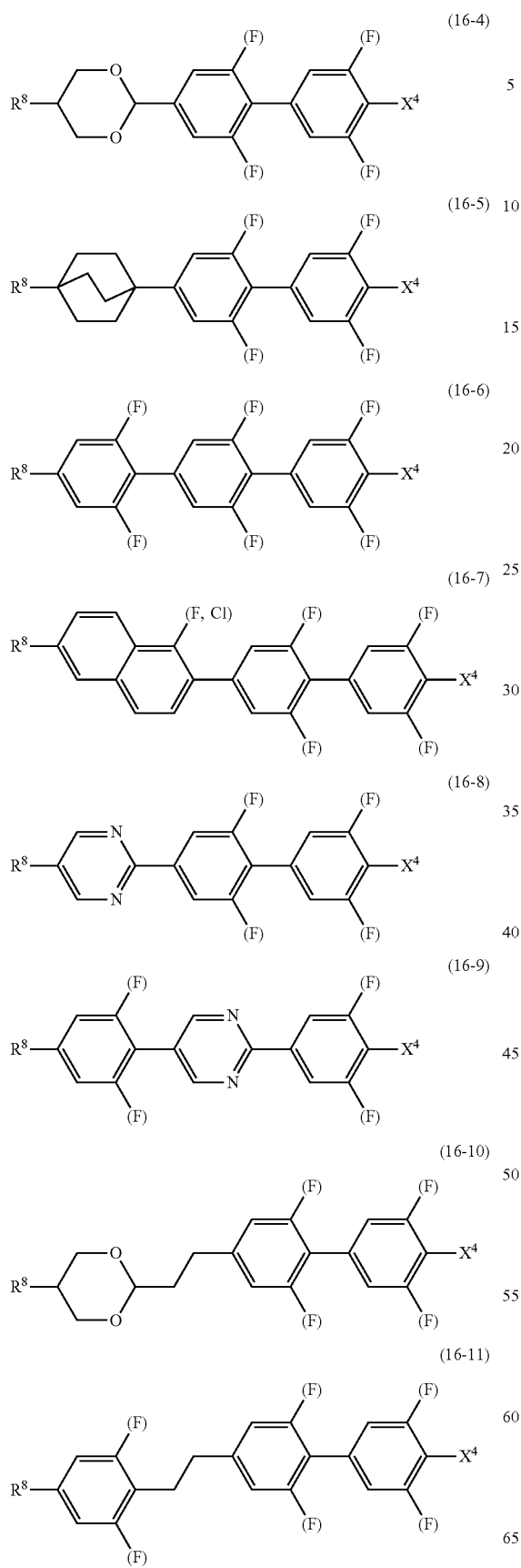
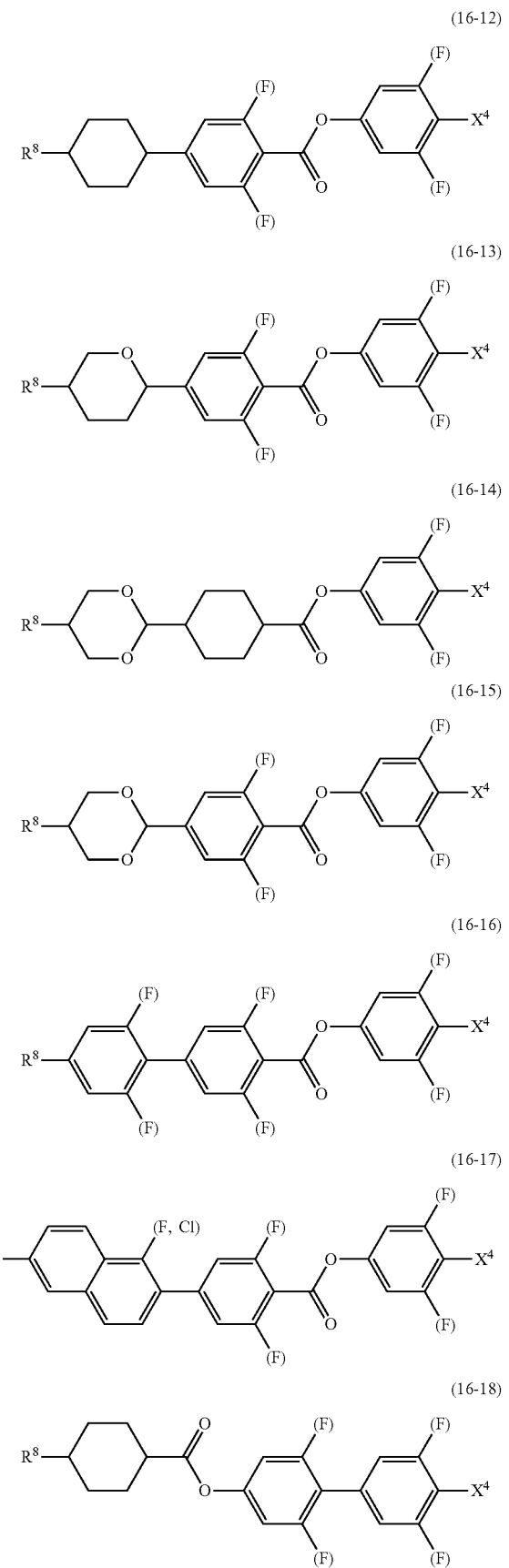

(16-19)
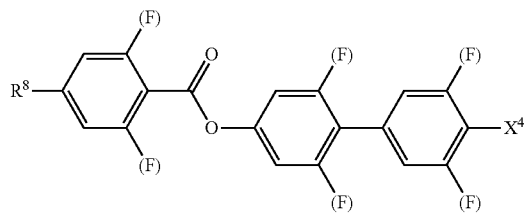
(16-20)
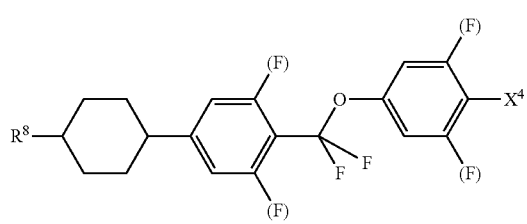
(16-21)
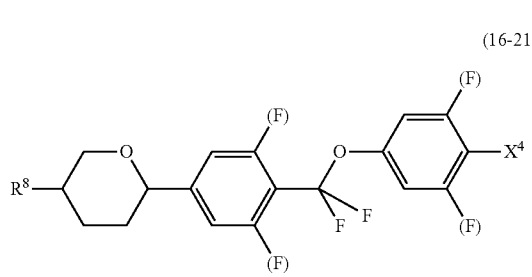
(16-22)
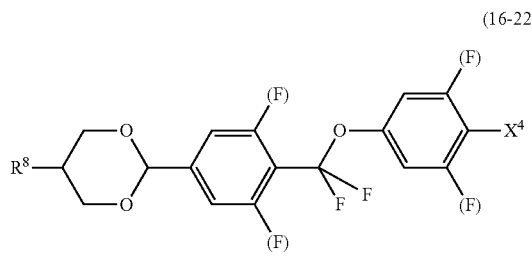
(16-23)
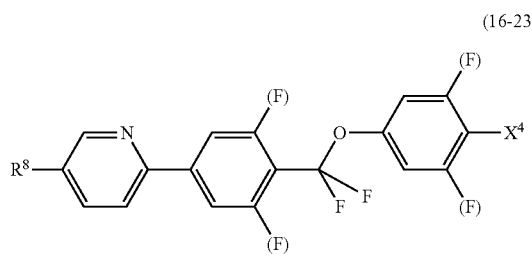
(16-24)
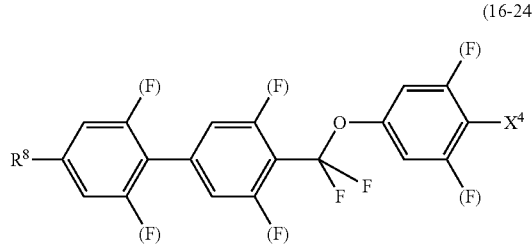
(16-25)
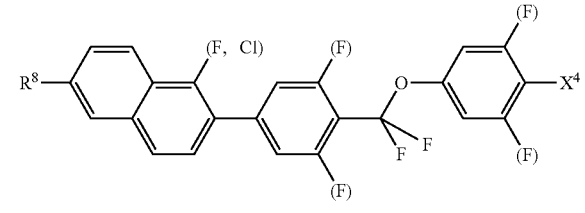
(16-26)
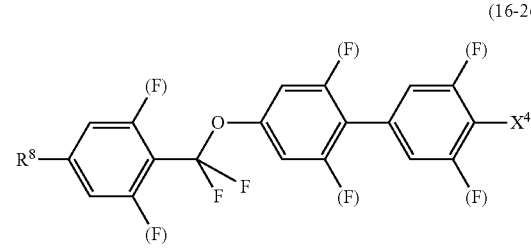
(17-1)
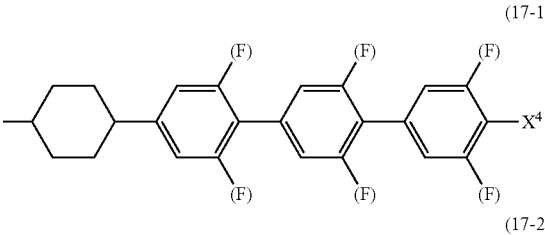
(17-2)
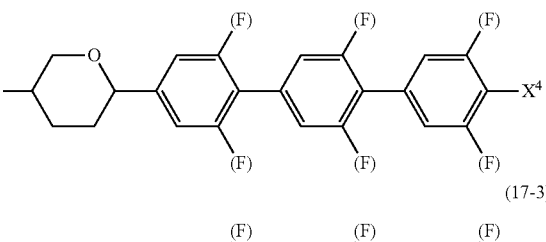
(17-3)
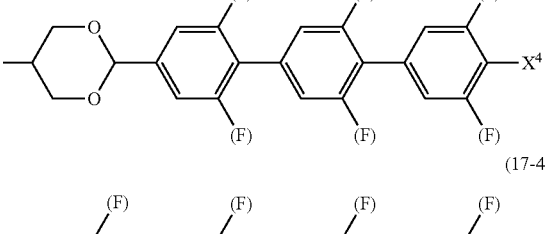
(17-4)
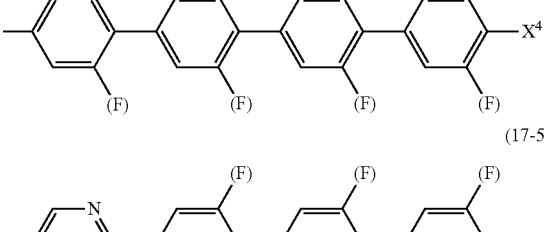
(17-5)
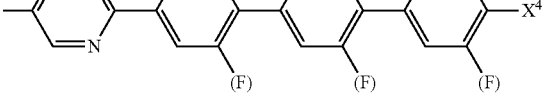

-continued
(17-6)
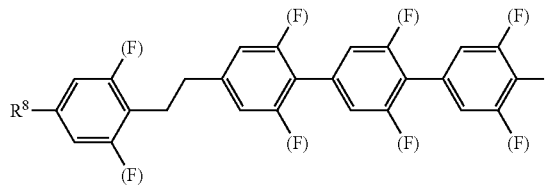
(17-7)
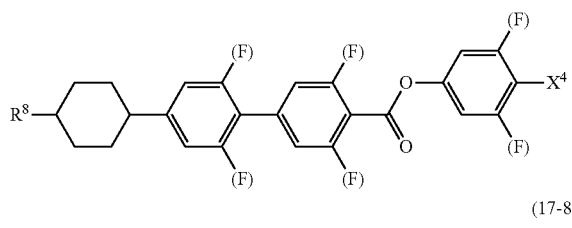
(17-8)
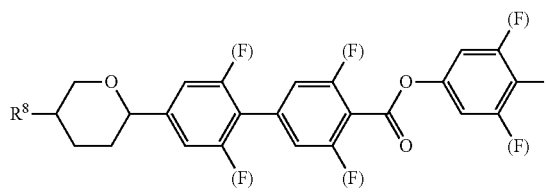
(17-9)
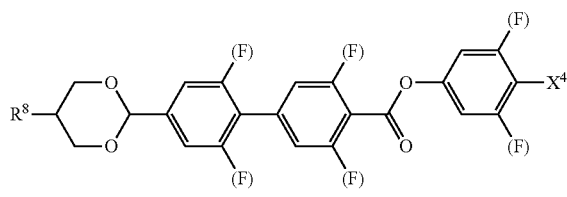
(17-10)
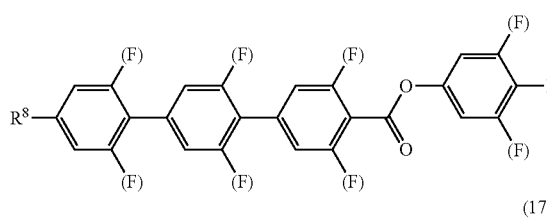
(17-11)
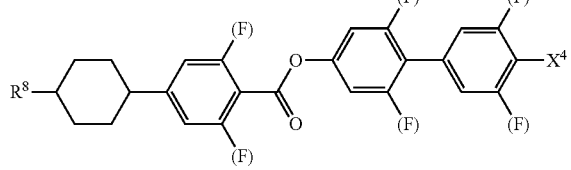
(17-12)
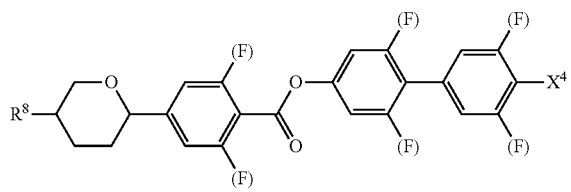
-continued
(17-13)
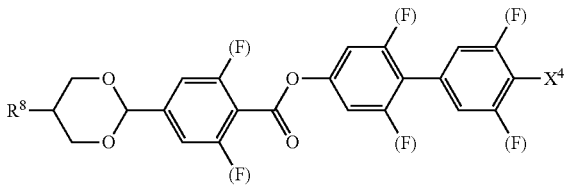
(17-14)
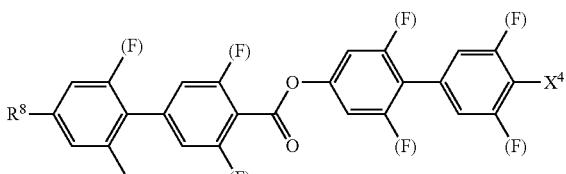
(17-15)
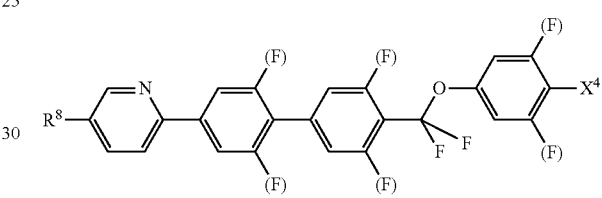
(17-16)
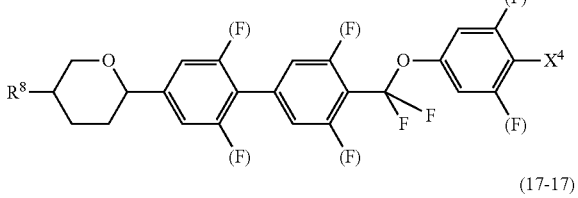
(17-17)
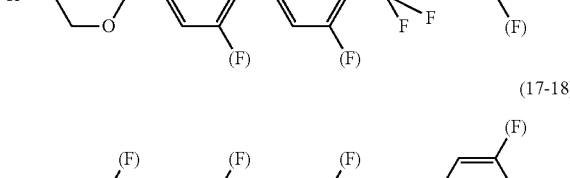
(17-18)
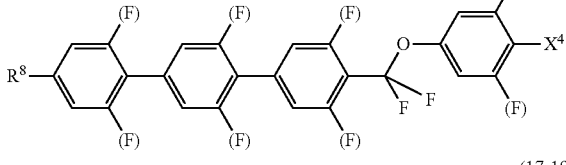
(17-19)
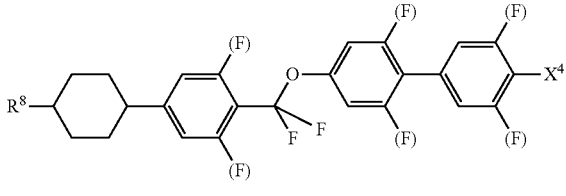

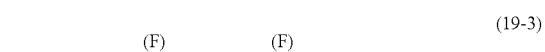
(17-20)

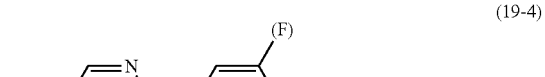
(17-21)

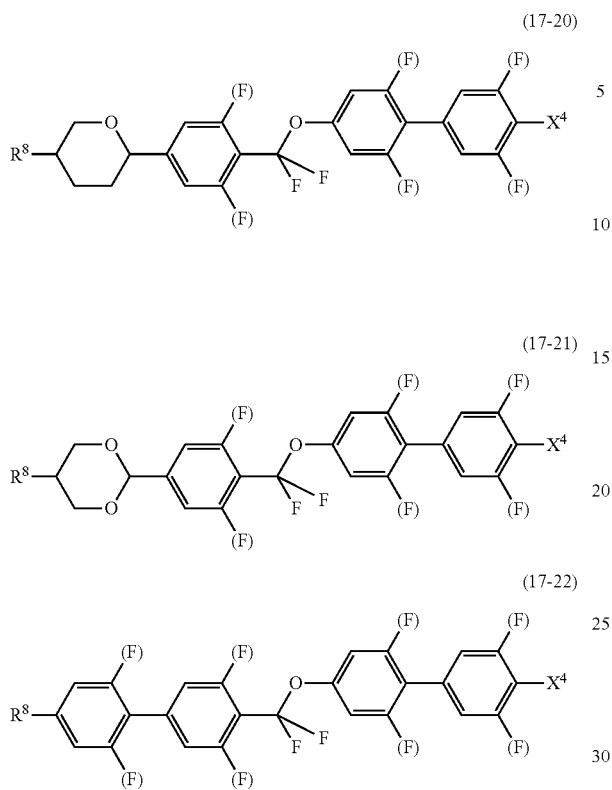
(17-22)

(in the formulas, $R^8$ and $X^4$ have the same meaning as described above, (F) denotes hydrogen or fluorine, and (F, Cl) denotes hydrogen, fluorine or chlorine).

The compounds of Formulas (15)-(18) (i.e., Component F) have a positive and very large dielectric anisotropy value and excellent thermal or chemical stability, thereby being suitable for preparing a liquid crystal composition used in active driving, such as TFT driving. In the liquid crystal composition of the present invention, the content of Component F is suitably in the range of 1 wt %-99 wt %, preferably 10 wt %-97 wt %, and more preferably 40 wt %-95 wt %, based on the total weight of the liquid crystal composition. Furthermore, by further containing the compounds of Formulas (11)-(13) (Component E), the viscosity may be adjusted.

Preferred examples of the compounds of Formula (19) (i.e., Component G) are Formulas (19-1)-(19-37).

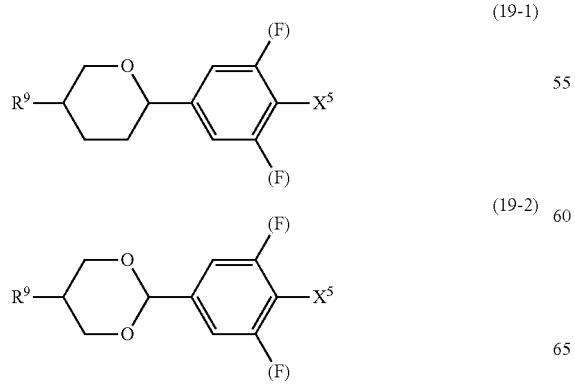
(19-1)

(19-2)

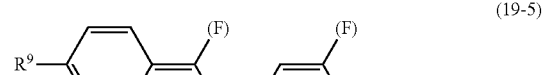
(19-3)

(19-4)

(19-5)

(19-6)

(19-7)

(19-8)

(19-9)

(19-10)

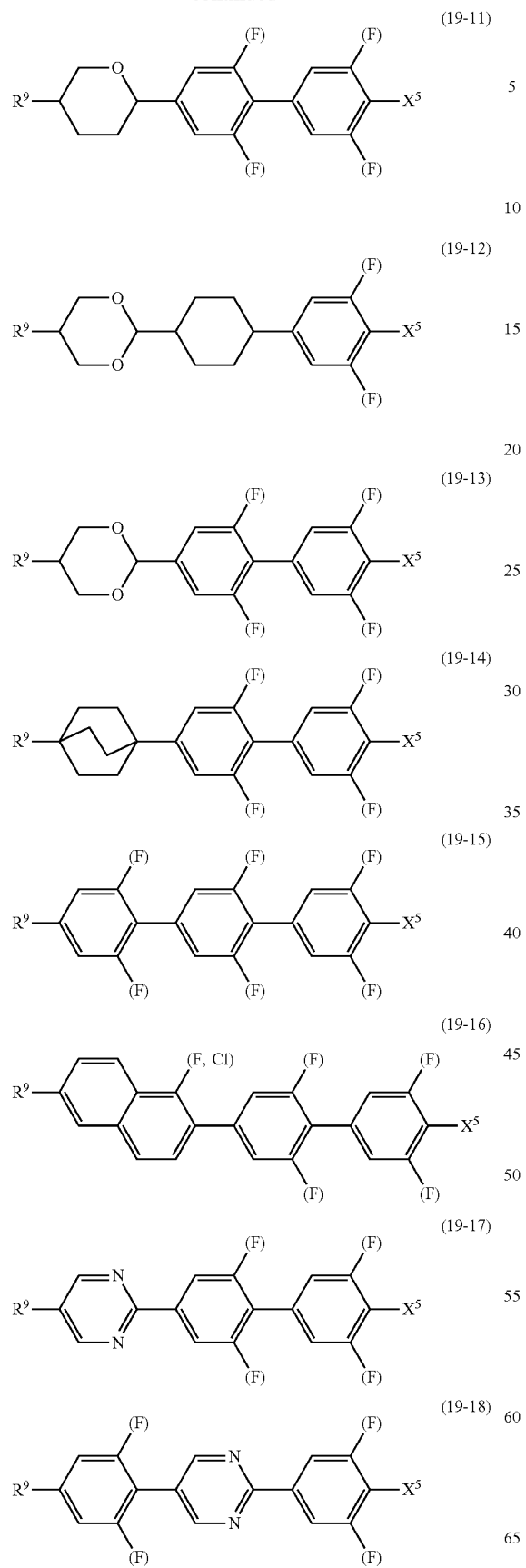
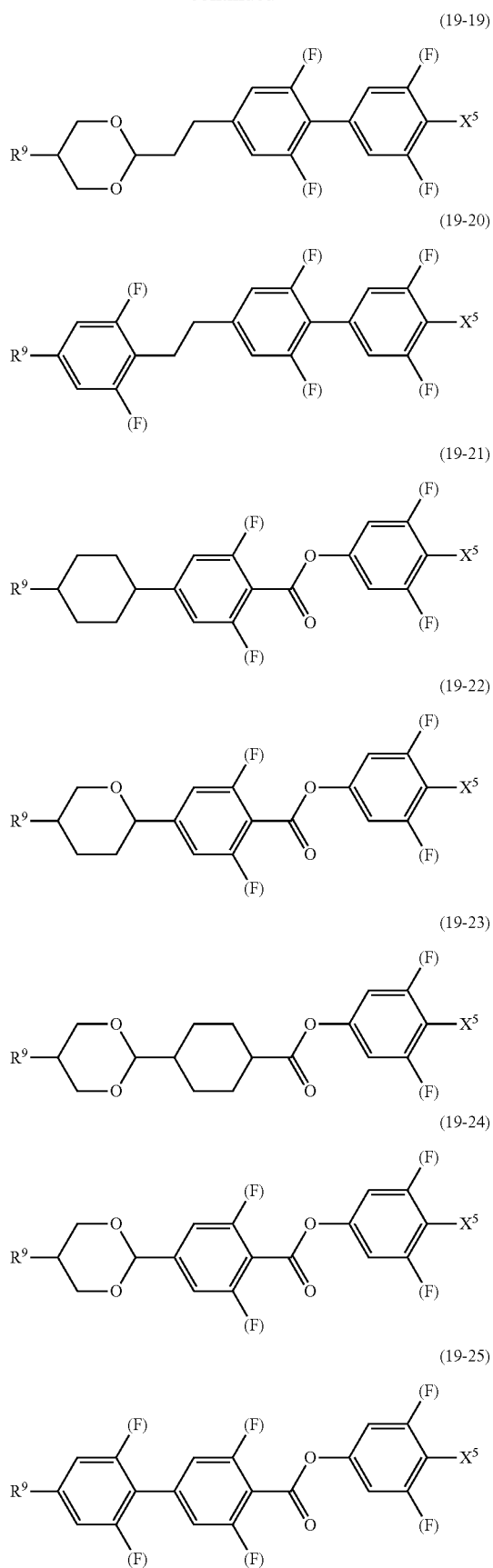

(19-26)
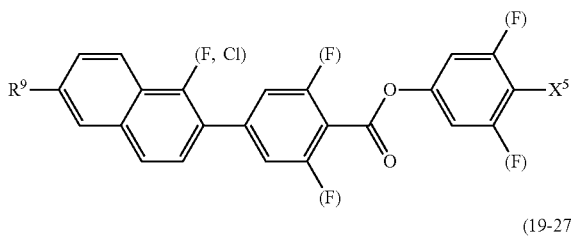

(19-27)
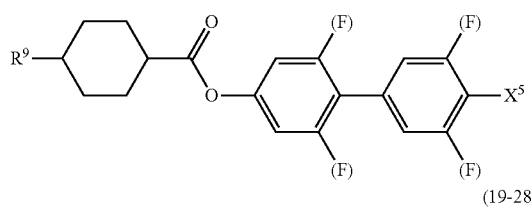

(19-28)
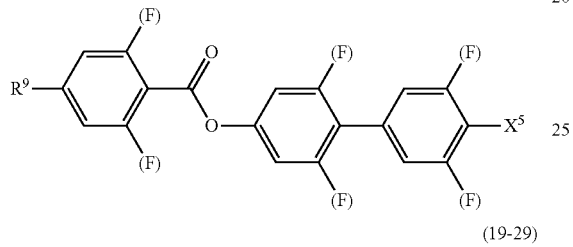

(19-29)
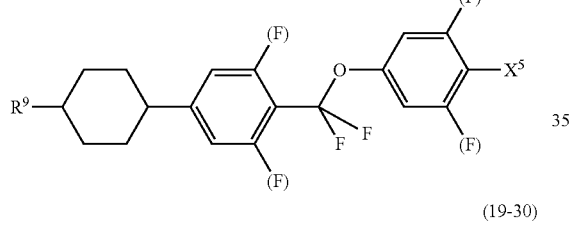

(19-30)
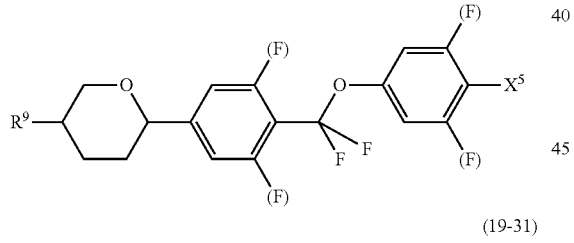

(19-31)
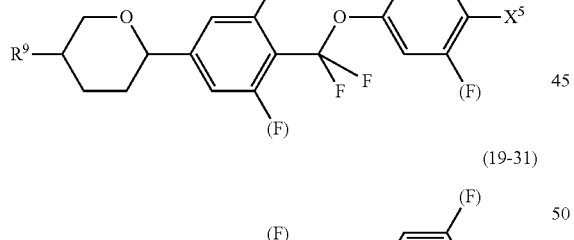

(19-32)
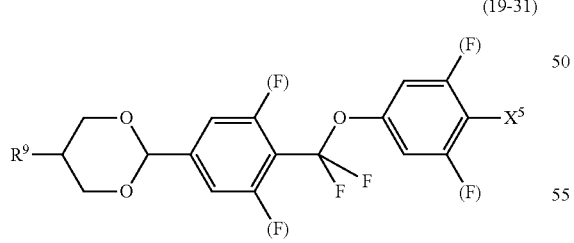

(19-33)
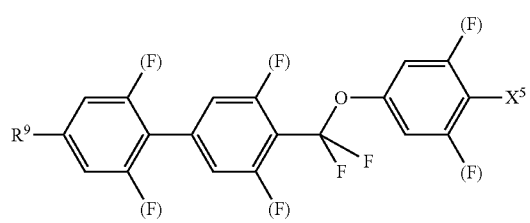

(19-34)
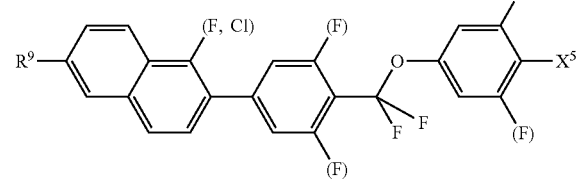

(19-35)
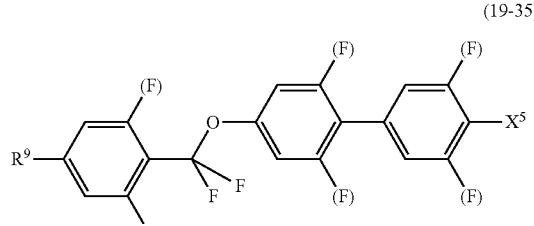

(19-36)
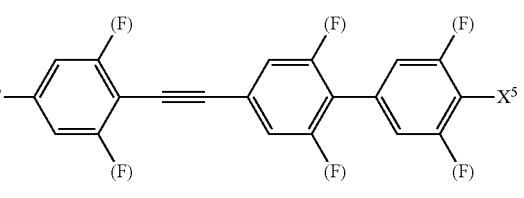

(19-37)
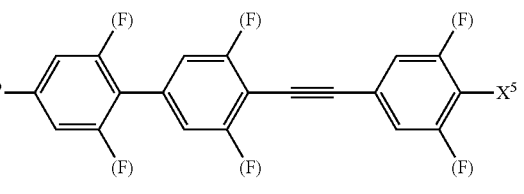

(in the formulas, $R^9$, $X^5$, (F), and (F, Cl) have the same meaning as described above)

The compounds of Formula (19) (i.e., Component G) have a positive and very large dielectric anisotropy value, thereby mainly being used to lower the driving voltage of the devices below: devices driven in an optically isotropic liquid crystal phase, polymer dispersed LCD (PDLCD), polymer network LCD (PNLCD), polymer-stabilized cholesteric LCD (PSCLCD). By containing Component G, the driving voltage of the composition is lowered, as well as the viscosity and the optical anisotropy value may be adjusted, and the temperature range of a liquid crystal phase is expanded. Moreover, the steepness is also improved.

The content of Component G is preferably in the range of 0.1 wt %-99.9 wt %, more preferably 10 wt %-97 wt %, and more preferably 40 wt %-95 wt %, based on the total weight of the composition.

4 Composition Having an Optically Isotropic Liquid Crystal Phase

4-1 Composition of a Composition Having an Optically Isotropic Liquid Crystal Phase A fourth aspect of the present invention is a composition containing the compound of Formula (1) and a chiral dopant, which is a liquid crystal composition useful in an optical device driven in an optically isotropic liquid crystal phase and exhibiting an optically isotropic liquid crystal phase.

Based on the total weight of the liquid crystal composition, the content of the chiral dopant is preferably 1 wt %-40 wt %, more preferably 3 wt %-25 wt %, and most preferably 5 wt %-15 wt %. A liquid crystal composition containing the chiral dopant in these ranges tends to have an optically isotropic liquid crystal phase, and thus is preferred.

The chiral dopant contained in the liquid crystal composition may be a single reagent, or a mixture of two or more reagents.

4-2 Chiral Dopant

The chiral dopant contained in the optically isotropic liquid crystal composition is preferably a compound with a large helical twisting power. As a compound with a large helical twisting power reduces the adding amount required for obtaining a desired pitch, a rise in the driving voltage can be suppressed, which is advantageous in practice. Specifically, the compounds of Formulas (K1)-(K5) above are preferred.

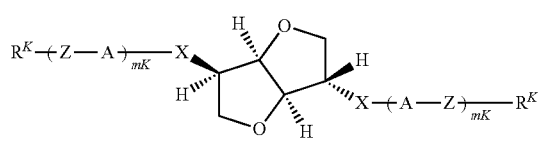
(K1)

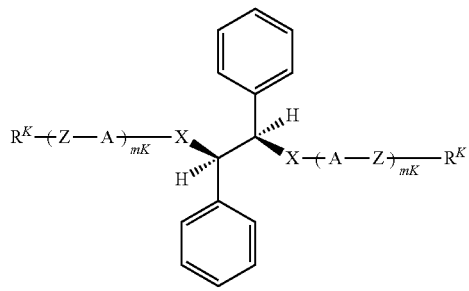
(K2)

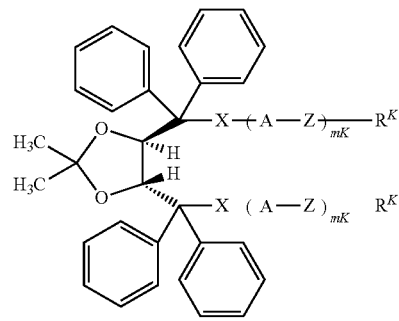
(K3)

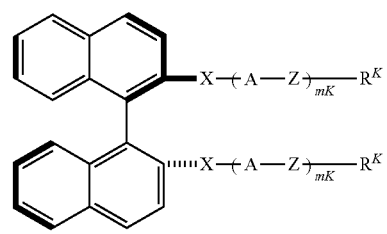
(K4)

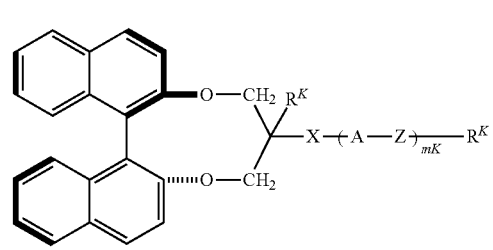
(K5)

In Formulas (K1)-(K5), $R^K$ is independently hydrogen, halogen, —C≡N, —N=C=O, —N=C=S, or $C_{1-20}$ alkyl, in which arbitrary —$CH_2$— in the alkyl may be replaced by —O—, —S—, —COO—, —OCO—, —CH=CH—, —CF=CF—, or —C≡C—, and arbitrary hydrogen in the alkyl and the alkyl with arbitrary —$CH_2$— replaced by —O—, —S—, —COO—, —OCO—, —CH=CH—, —CF=CF—, or —C≡C— may be replaced by halogen; A is independently an aromatic or non-aromatic 3- to 8-membered ring, or a fused ring having 9 or more carbon atoms, in which arbitrary hydrogen in the rings may be replaced by halogen, a $C_{1-3}$ alkyl, or a haloalkyl, arbitrary —$CH_2$— in the rings may be replaced by —O—, —S—, or —NH—, and arbitrary —CH= in the rings may be replaced by —N=; Z is independently a single bond, $C_{1-8}$ alkylene, in which arbitrary —$CH_2$— in the alkylene may be replaced by —O—, —S—, —COO—, —OCO—, —CSO—, —N=N—, —CH=N—, —N=CH—, —CH=CH—, —CF=CF—, or —C≡C—, arbitrary hydrogen in the alkylene and the alkylene with arbitrary —$CH_2$— replaced by —O—, —S—, —COO—, —OCO—, —CSO—, —OCS—, —N=N—, —CH=N—, —N=CH—, —CH=CH—, —CF=CF—, or —C≡C— may be replaced by halogen; X is a single bond, —COO—, —OCO—, —$CH_2O$—, —$OCH_2$—, —$CF_2O$—, —$CH_2CH_2$—; and mK is 1-4.

Among these, the chiral dopant added into the liquid crystal composition is preferably Formulas (K2-1)-(K2-8) included in Formula (K2) and Formulas (K5-1)-(K5-3) included in Formula (K5).

(K2-1)
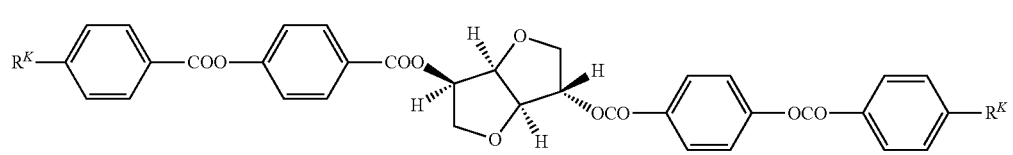
(K2-2)
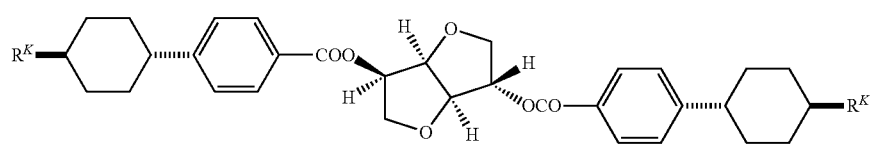
(K2-3)
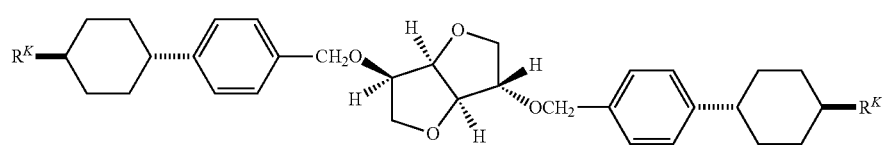
(K2-4)
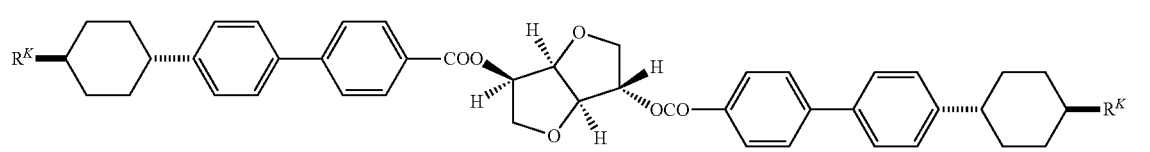
(K2-5)
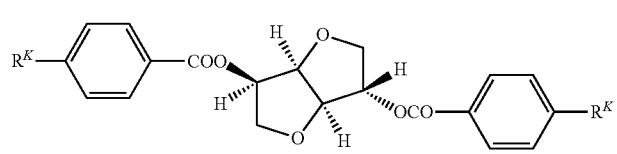
(K2-6)
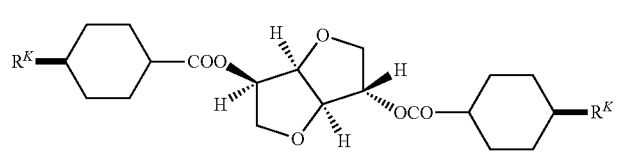
(K2-7)
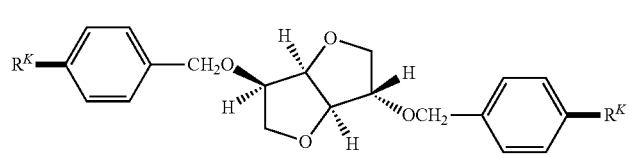
(K2-8)
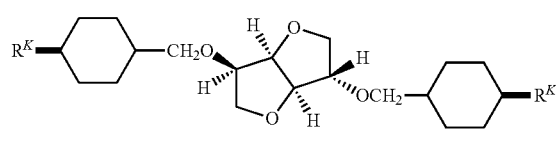
(K5-1)
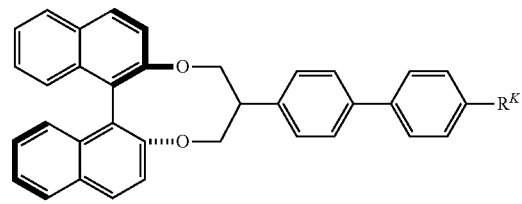
(K5-2)
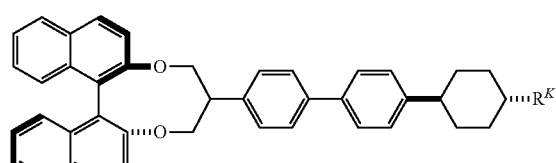
(K5-3)
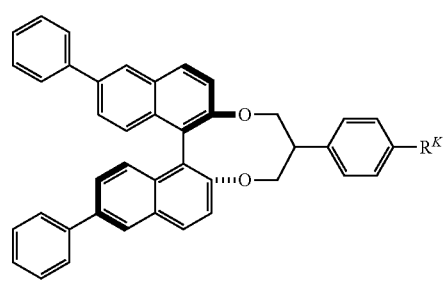

(in the formulas, $R^K$ is independently a $C_{3-10}$ alkyl, in which —$CH_2$— adjacent to the ring in the alkyl may be replaced by —O—, and arbitrary —$CH_2$— not adjacent to the ring in the alkyl may be replaced by —CH=CH—).

4-3 Optically Isotropic Liquid Crystal Phase

The so-called liquid crystal composition having optically isotropy means that the composition exhibits an optical isotropy because the liquid crystal molecules macroscopically have an isotropic arrangement, but microscopically there exists a liquid crystal order. "Pitch corresponding to the microscopic liquid crystal order of the liquid crystal composition (sometimes referred to as pitch, hereafter)" is preferably 700 nm or less, more preferably 500 nm or less, and most preferably 350 nm or less.

Herein, the so-called "non-liquid crystal isotropic phase" refers to a commonly defined isotropic phase (i.e. disordered phase), and refers to an isotropic phase where a region with a non-zero local order parameter is generated due to fluctuation. For example, an isotropic phase exhibited at a high temperature side of a nematic phase is equivalent to the non-liquid crystal isotropic phase in this specification. The chiral liquid crystal in this specification also has a similar definition. Moreover, the so-called "optically isotropic liquid crystal phase" in this specification means a phase that exhibits an optical isotropy without fluctuation, an example of which is a phase exhibiting a platelet texture (i.e. blue phase in narrow sense).

The optically isotropic liquid crystal composition of the present invention has an optically isotropic liquid crystal phase. However, the typical platelet texture is not observed in the blue phase under a polarizing microscope sometimes. Therefore, in this specification, a phase exhibiting the platelet texture is designated as blue phase, and an optically isotropic liquid crystal phase including the blue phase is designated as optically isotropic liquid crystal phase. That is, the blue phase is included in the optically isotropic liquid crystal phase.

Generally, the blue phase is divided into three types, that is, blue phase I, blue phase II, and blue phase III, and all the three blue phases are optical active and isotropic. In the blue phase I or blue phase II, two or more diffracted lights produced by the Bragg reflection from different lattice planes are observed. The blue phase is generally observed between the non-liquid crystal isotropic phase and the chiral nematic phase.

The so-called state that the optically isotropic liquid crystal phase does not exhibit two or more colors of diffracted light means that a platelet texture observed in the blue phase I and blue phase II is not observed and the phase exhibits substantially a single color in the entire plane. For an optically isotropic liquid crystal phase not exhibiting two or more colors of diffracted light, brightness/darkness of the colors is not necessarily to be even in plane.

The optically isotropic liquid crystal phase not exhibiting two or more colors of diffracted light has the advantage of inhibiting the intensity of reflected light caused by Bragg reflection, or shifting toward low wavelength side.

Furthermore, when a liquid crystal material reflecting visible light is used in a display device, sometimes a color variation problem may occur. However, for a liquid crystal not exhibiting two or more colors of diffracted light, because reflection wavelength shift toward the low wavelength side, the reflection of visible light may be eliminated by the pitch longer than that in the blue phase in narrow sense (a phase exhibiting the platelet texture).

The optically isotropic liquid crystal composition of the present invention may be obtained by adding a chiral dopant into a composition having a nematic phase. In this case, the chiral dopant is preferably added in a concentration such that the pitch is 700 nm or less. Furthermore, the composition having a nematic phase contains the compound of Formula (1) and other optional components. Moreover, the optically isotropic liquid crystal composition of the present invention can also be obtained by adding a chiral dopant to a composition having a chiral nematic phase but no optically isotropic liquid crystal phase. Furthermore, the composition having a chiral nematic phase but no optically isotropic liquid phase contains the compound of Formula (1), an optically active compound, and other optional components. In this case, the optically active compound is preferably added in a concentration such that the pitch is 700 nm or more, so as not to exhibit an optically isotropic liquid crystal phase. Here, the optically active compounds to be added can be the compounds with a large helical twisting power above, that is, the compounds of Formulas (K-1)-(K-4), Formulas (K2-1)-(K2-8), or Formulas (K5-1)-(K5-4). Moreover, the optically active compound added may not have so large helical twisting power. Such an optically active compound is, for example, one added in a liquid crystal composition for a device driven in a nematic phase (TN, STN mode, and the like).

Examples of the optical active compound without so large helical twisting power are the following optical active compounds (Op-1)-(Op-13).

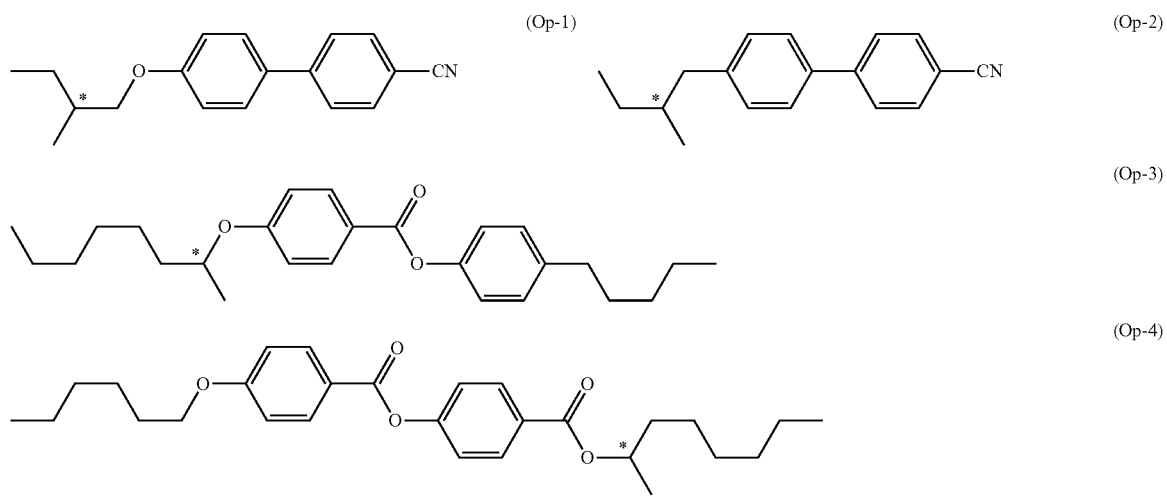

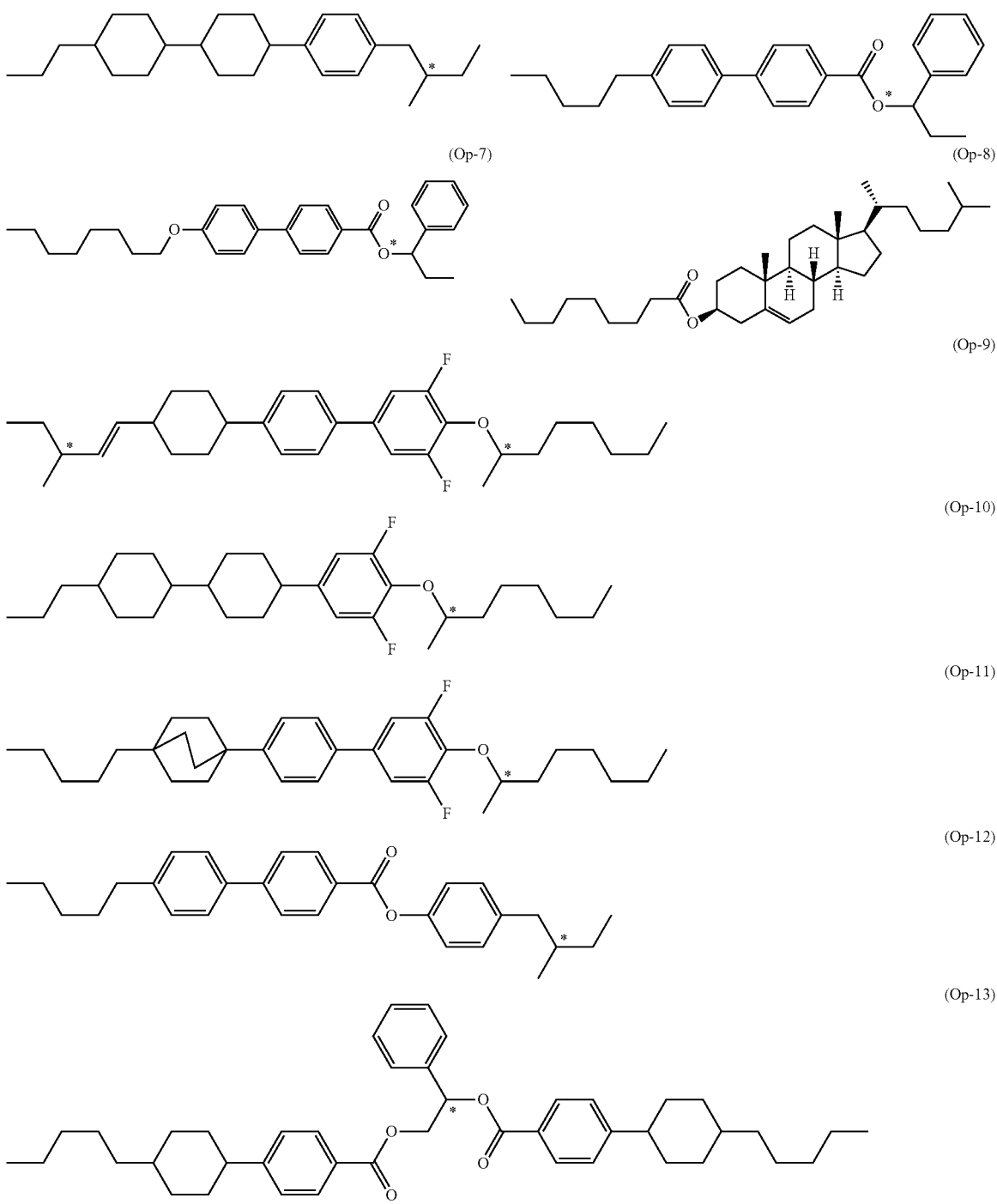

Moreover, the temperature range of the optically isotropic liquid crystal composition of the present invention may be expanded by adding a chiral dopant into a liquid crystal composition having a wide temperature range of the co-existence of a nematic phase or a chiral nematic phase and an isotropic phase for exhibiting an optically isotropic liquid crystal phase. For example, a composition exhibiting an optically isotropic liquid crystal phase in a wide temperature range can be prepared as follows: a liquid crystal compound having a high clearing point is mixed with a liquid crystal compound having a low clearing point, and a liquid crystal composition with a wide co-existence temperature range of a nematic phase and an isotropic phase is prepared in a wide temperature range; and then, a chiral dopant is added to the liquid crystal composition.

For a liquid crystal composition with a wide co-existence temperature range of a nematic phase or chiral nematic phase and an isotropic phase, the difference between the upper-limit temperature and lower-limit temperature of the co-existence of a chiral nematic phase and a non-liquid crystal isotropic phase is preferably 3-150° C., and more preferably 5-150° C. Moreover, the liquid crystal composition preferably has a difference between the upper-limit temperature and lower-limit temperature of the co-existence of a nematic phase and a non-liquid crystal isotropic phase of 3-150° C.

When an electric field is applied to the liquid crystal medium of the present invention in an optically isotropic liquid crystal phase, an electrically controlled birefringence occurs, but the Kerr effect does not necessarily occur.

Because the electrically controlled birefringence effect of an optically isotropic liquid crystal phase increases with the pitch, the electrically controlled birefringence effect may be improved by adjusting the type and content of the chiral dopant to increase the pitch, as long as other optical properties, such as, transmittance and diffraction wavelength, could be satisfied.

4-4 Other Components

Other compounds, such as polymer material, may be further added into the optically isotropic liquid crystal composition of the present invention, so long as they do not affect the properties of the composition. In addition to the polymer material, the liquid crystal composition of the present invention can also contain, for example, a dichroic dye or a photochromic compound. Examples of the dichroic dye include merocyanine-based dyes, styryl-based dyes, azo-based dyes, azomethine-based dyes, azoxy-based dyes, quinophthalone-based dyes, anthraquinone-based dyes, tetrazine-based dyes, and the like.

5 Optically Isotropic Polymer/Liquid Crystal Composite Material

A fifth aspect of the present invention is a composite material of a polymer compound and a liquid crystal composition containing the compound of Formula (1) and a chiral dopant, which exhibits an optical isotropy. The composite material is an optically isotropic polymer/liquid crystal composite material which can be used in an optical device driven in an optically isotropic liquid crystal phase. Such a polymer/liquid crystal composite material is composed of, for example, the liquid crystal composition according to Items [1]-[30] (cholesteric liquid crystal composition CLC) and a polymer.

The "polymer/liquid crystal composite material" of the present invention has no particular limitation, as long as it is a composite containing both a liquid crystal material and a polymer compound. It also includes a state where the polymer compound and the liquid crystal material are in phase separation because the polymer compound is partially or entirely not dissolved in the liquid crystal material. Furthermore, in this specification, a nematic phase refers to one in narrow sense excluding a chiral nematic phase, unless specifically indicated.

The optically isotropic polymer/liquid crystal composite material according to a preferred aspect of the present invention can exhibit an optically isotropic liquid crystal phase in a wide temperature range. Moreover, the polymer/liquid crystal composite material according to a preferred aspect of the present invention has very high response speed. Furthermore, based on such effects, the polymer/liquid crystal composite material according to a preferred aspect of the present invention is useful in an optical device such as a display device.

5-1 Polymer

Though the composite material of the present invention can be produced by mixing an optically isotropic liquid crystal composition with a pre-polymerized polymer, it is preferably produced by mixing a low molecular weight monomer, macromonomer, or oligomer, etc (generally referred to as "monomers", hereafter) to be foil led into a polymer material, with the liquid crystal composition (cholesteric liquid crystal composition CLC), and then polymerizing the mixture. In this specification, the mixture containing the monomers and the liquid crystal composition is referred to as "polymerizable monomer/liquid crystal mixture". The "polymerizable monomer/liquid crystal mixture" may optionally contain a polymerization initiator, a curing agent, a catalyst, a stabilizer, a dichroic dye, or a photochromic compound, and the like, without compromising the effect of the present invention. For example, the polymerizable monomer/liquid crystal mixture of the present invention may also optionally contain 0.1-20 weight parts of a polymerization initiator, based on 100 weight parts of the polymerizable monomer.

The polymerization temperature is preferably such a temperature that the polymer/liquid crystal composite material exhibits high transparency and isotropy, and more preferably such a temperature that the mixture of the monomer and the liquid crystal material exhibits an isotropic phase or a blue phase, while the polymerization is carried out in the isotropic phase or optically isotropic liquid crystal phase. That is, the temperature is preferably set, such that after the polymerization, the polymer/liquid crystal composite material substantially does not scatter light of wavelength greater than that of visible light and exhibits an optical isotropy.

For example, a low molecular weight monomer, macromonomer, and oligomer may be used as a raw material of the polymer compound for forming the composite material of the present invention. In this specification, the raw material monomers of the polymer compound include low molecular weight monomers, macromonomers, oligomers, and the like. Furthermore, the obtained polymer compound preferably has a three-dimensional cross-linked structure, and thus the raw material monomer of the polymer compound is preferably a multi-functional monomer having two or more polymerizable functional groups. The polymerizable functional groups have no particular limitation, and include, for example, acryloyl, methacryloyl, glycidyl, epoxy, oxetanyl, vinyl, and the like. In view of the polymerization rate, acryloyl and methacryloyl are preferred. The raw material monomers of the polymer compound containing 10 wt % or more of the monomers having two or more polymerizable functional groups are preferred, since the obtained composite material of the present invention easily exhibits high transparency and isotropy.

Moreover, in order to obtain a better composite material, the polymer preferably has a mesogen moiety, and a part or all of the raw material monomers used have a mesogen moiety.

5-1-1 Mono-Functional and Difunctional Monomer Having Mesogen Moiety

The mono- or difunctional monomer having a mesogen moiety has no particular limitation in structure, and may be, for example, the compounds of Formula (M1) or (M2) below.

 (M1)

 (M2)

 (M3-1)

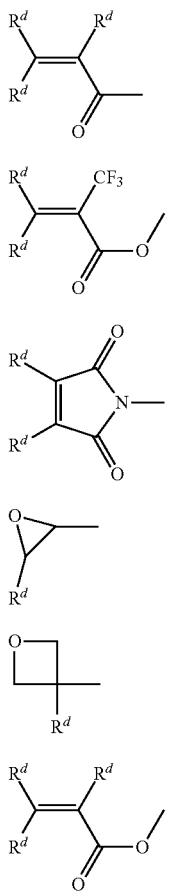

(M3-2)
(M3-3)
(M3-4)
(M3-5)
(M3-6)
(M3-7)

In Formula (M1), $R^a$ is independently hydrogen, halogen, —C≡N, —N=C=O, —N=C=S, or $C_{1-20}$ alkyl, in which arbitrary —CH$_2$— in the alkyl may be replaced by —O—, —S—, —CO—, —COO—, —OCO—, —CH=CH—, —CF=CF—, or —C≡C—, and arbitrary hydrogen in the alkyl and the alkyl with arbitrary —CH$_2$— replaced by —O—, —S—, —CO—, —COO—, —OCO—, —CH=CH—, —CF=CF—, or —C≡C— may be replaced by halogen, or —C≡N. $R^b$ is independently a polymerable group of Formulas (M3-1)-(M3-7).

$R^a$ is preferably hydrogen, halogen, —C≡N, —CF$_3$, —CF$_2$H, —CFH$_2$, —OCF$_3$, —OCF$_2$H, a $C_{1-20}$ alkyl, a $C_{1-19}$ alkoxy, a $C_{2-21}$ alkenyl, or a $C_{2-21}$ alkynyl. Most preferably, $R^a$ is —C≡N, a $C_{1-20}$ alkyl, or a $C_{1-19}$ alkoxy.

In Formula (M2), $R^b$ is independently a polymerable group of Formulas (M3-1)-(M3-7).

In Formulas (M3-1)-(M3-7), $R^d$ is independently hydrogen, halogen, or a $C_{1-5}$ alkyl, in which arbitrary hydrogen in the alkyl may be replaced by halogen. $R^d$ is preferably hydrogen, halogen, or methyl. Most preferably, $R^d$ is hydrogen, fluorine, or methyl.

Furthermore, Formulas (M3-2), (M3-3), (M3-4), and (M3-7) are preferably polymerized through free radical polymerization. Formulas (M3-1), (M3-5), and (M3-6) are preferably polymerized through cationic polymerization. The polymerizations are both living polymerization, and thus can be initiated only when a small amount of free radical or cationic active species is generated in the reaction system. In order to accelerate the generation of the active species, a polymerization initiator may be used. Light or heat may be used to generate the active species.

In Formulas (M1) and (M2), $A^M$ is independently an aromatic or non-aromatic 5- or 6-membered ring, or a fused ring having 9 or more carbon atoms, in which —CH$_2$— in the rings may be replaced by —O—, —S—, —NH—, or —NCH$_3$—, —CH= in the rings may be replaced by —N=, and hydrogen atom in the rings may be replaced by halogen, a $C_{1-5}$ alkyl or haloalkyl. Specific examples of preferred $A^M$ are 1,4-cyclohexylene, 1,4-cyclohexenylene, 1,4-phenylene, naphthalene-2,6-diyl, tetrahydronaphthalene-2,6-diyl, fluorene-2,7-diyl, or bicyclo[2.2.2]octane-1,4-diyl, in which arbitrary —CH$_2$— in the rings may be replaced by —O—, arbitrary —CH= in the ring may be replaced by —N=, and arbitrary hydrogen in the rings may be replaced by halogen, a $C_{1-5}$ alkyl, or a $C_{1-5}$ haloalkyl.

In consideration of the stability of the compound, —CH$_2$—O—CH$_2$—O— with oxygen being not adjacent to one another is preferred to —CH$_2$—O—O—CH$_2$— with oxygen being adjacent to one another. The same case is applicable to sulphur.

Among these, especially preferred $A^M$ is 1,4-cyclohexylene, 1,4-cyclohexenylene, 1,4-phenylene, 2-fluoro-1,4-phenylene, 2,3-difluoro-1,4-phenylene, 2,5-difluoro-1,4-phenylene, 2,6-difluoro-1,4-phenylene, 2-methyl-1,4-phenylene, 2-trifluoromethyl-1,4-phenylene, 2,3-bis(trifluoromethyl)-1,4-phenylene, naphthalene-2,6-diyl, tetrahydronaphthalene-2,6-diyl, fluorene-2,7-diyl, 9-methylfluorene-2,7-diyl, 1,3-dioxane-2,5-diyl, pyridine-2,5-diyl, and pyrimidine-2,5-diyl. Moreover, as for the stereo configuration of 1,4-cyclohexylene and 1,3-dioxane-2,5-diyl, trans configuration is superior to cis configuration.

Because 2-fluoro-1,4-phenylene and 3-fluoro-1,4-phenylene are identical in structure, the latter is not exemplified. This rule is also applicable to the relationship between 2,5-difluoro-1,4-phenylene and 3,6-difluoro-1,4-phenylene.

In Formulas (M1) and (M2), Y is independently a single bond or a $C_{1-20}$ alkylene, in which arbitrary —CH$_2$— in the alkylene may be replaced by —O—, —S—, —CH=CH—, —COO—, or —COO—. Preferably, Y is a single bond, —(CH$_2$)$_{m2}$—, —O(CH$_2$)$_{m2}$—, or —(CH$_2$)$_{m2}$O— (where m2 is an integer of 1-20). Particularly preferably, Y is a single bond, —(CH$_2$)$_{m2}$—, —O(CH$_2$)$_{m2}$ or —(CH$_2$)$_{m2}$O— (where m2 is an integer of 1-10). In consideration of the stability of the compound, —Y—$R^a$ and —Y—$R^b$ preferably have no —O—O—, —O—S—, —S—O—, or —S—S—.

In Formulas (M1) and (M2), $Z^M$ is independently a single bond, —(CH$_2$)$_{m3}$—, —O(CH$_2$)$_{m3}$—, —(CH$_2$)$_{m3}$O—, —O(CH$_2$)$_{m3}$O—, —CH=CH—, —C≡C—, —COO—, —OCO—, —(CF$_2$)$_2$—, —(CH$_2$)$_2$—COO—, —OCO—(CH$_2$)$_2$—, —CH=CH—COO—, —OCO—CH=CH—, —CH=CH—(CH$_2$)$_2$—, —(CH$_2$)$_2$—CH=CH—, —CF=CF—, —C≡C—CH=CH—, —CH=CH—C≡C—, —OCF$_2$—(CH$_2$)$_2$—, —(CH$_2$)$_2$—CF$_2$O—, —OCF$_2$—, or —CF$_2$O— (where m3 is an integer of 1-20). $Z^M$ is preferably a single bond, —(CH$_2$)$_{m3}$—, —O(CH$_2$)$_{m3}$—, —(CH$_2$)$_{m3}$O—, —CH=CH—, —C≡C—, —COO—, —OCO—, —(CH$_2$)$_2$—COO—, —OCO—(CH$_2$)$_2$—, —CH=CH—COO—, —OCO—CH=CH—, —OCF$_2$—, and —CF$_2$O—.

In Formulas (M1) and (M2), m1 is an integer of 1-6, and preferably an integer of 1-3. When m1 is 1, the compound is a 2-rings compound having two, for example, 6-membered rings. When m1 is 2 or 3, the compound is a 3-rings or 4-rings compound, respectively. For example, when m1 is 1, two $A^M$ may be identical or different. Also, for example, when m1 is 2, three $A^M$ (or two $Z^M$) may be identical or different. When m1 is 3-6, it is also the same case. The same case is also applicable to Ra, Rb, Rd, $Z^M$, $A^M$, and Y.

Even the Compound (M1) of Formula (M1) and the Compound (M2) of Formula (M2) containing an isotope in an amount higher than its natural abundance, such as $^2$H (deuterium) and $^{13}$C are useful, due to the identical properties.

More preferred examples of Compounds (M1) and (M2) are Compounds (M1-1)-(M1-41) and (M2-1)-(M2-27) of Formulas (M1-1)-(M1-41) and (M2-1)-(M2-27). Among the compounds, $R^a$, $R^b$, $R^d$, $Z^M$, $A^M$, Y, and p have the same meaning as those described for Formulas (M1) and (M2) in the previous aspects of the present invention.

Each partial structure of Compounds (M1-1)-(M1-41) and Compounds (M2-1)-(M2-27) is described as follows. Partial structure (a1) represents 1,4-phenylene with arbitrary hydrogen replaced by fluorine. Partial structure (a2) represents 1,4-phenylene in which arbitrary hydrogen may be replaced by fluorine. Partial structure (a3) represents 1,4-phenylene in which arbitrary hydrogen may be replaced by either fluorine or methyl. Partial structure (a4) represents fluorene in which hydrogen at position 9 may be replaced by methyl.

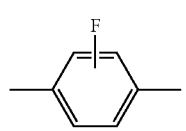
(a1)

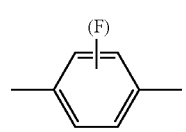
(a2)

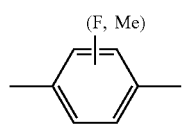
(a3)

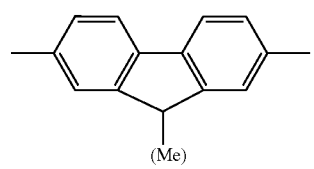
(a4)

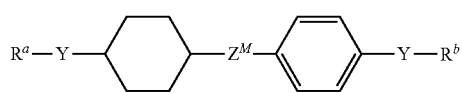
(M1-1)

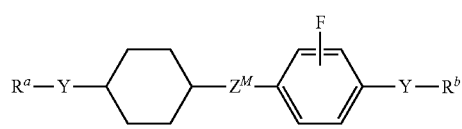
(M1-2)

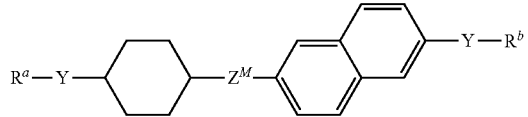
(M1-3)

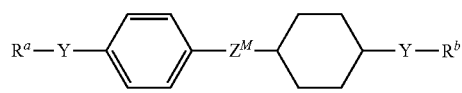
(M1-4)

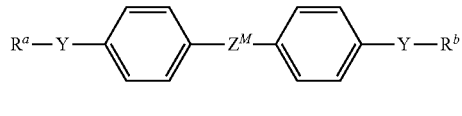
(M1-5)

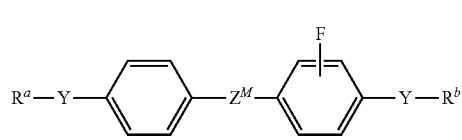
(M1-6)

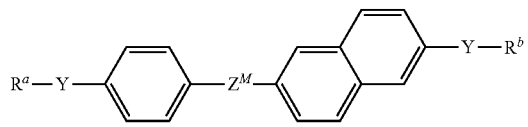
(M1-7)

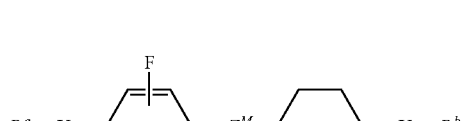
(M1-8)

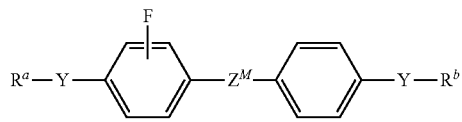
(M1-9)

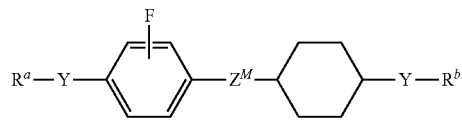
(M1-10)

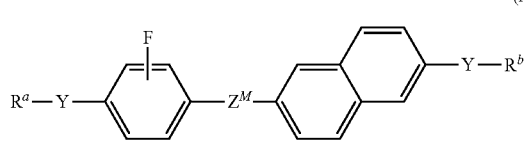
(M1-11)

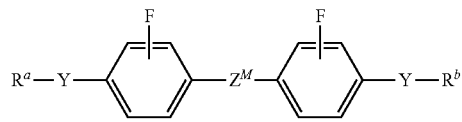
(M1-12)

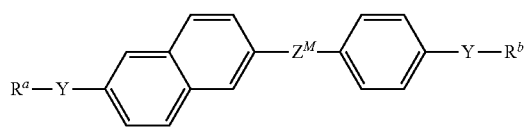
(M1-13)

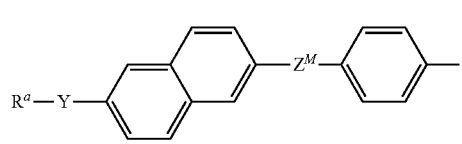
(M1-14)

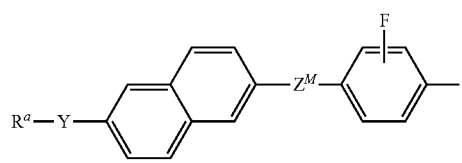

-continued
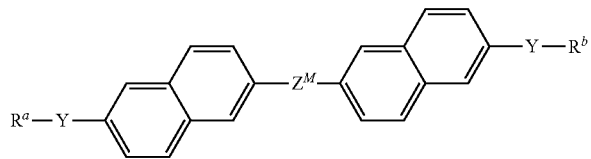
(M1-15)
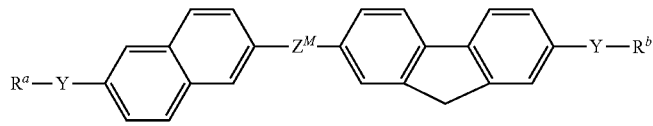
(M1-16)
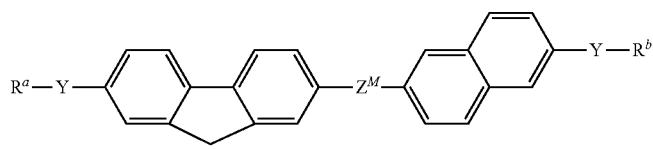
(M1-17)
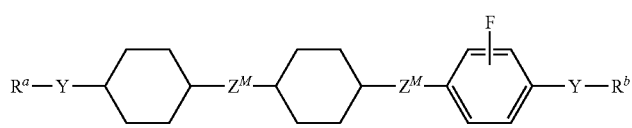
(M1-18)
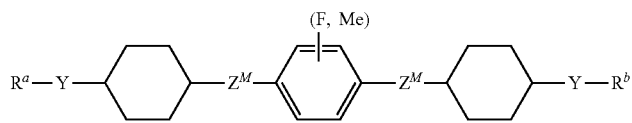
(M1-19)
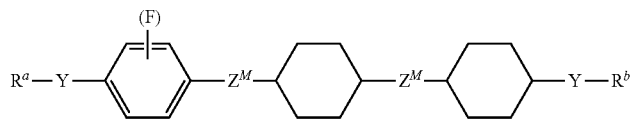
(M1-20)
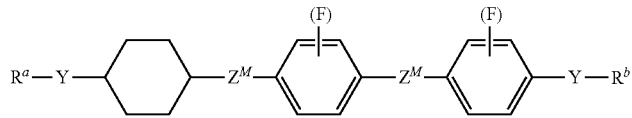
(M1-21)
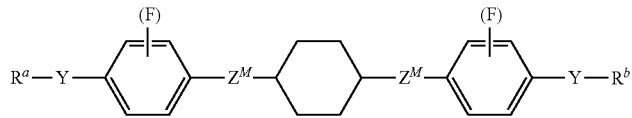
(M1-22)
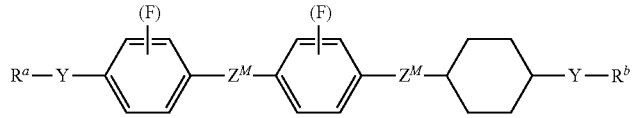
(M1-23)
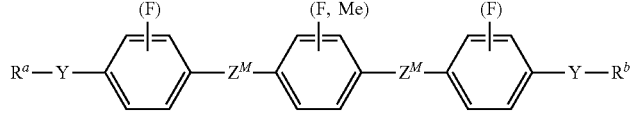
(M1-24)
(M1-25)

-continued
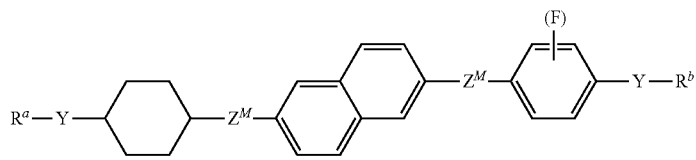
(M1-26)
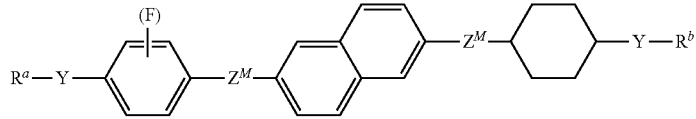
(M1-27)
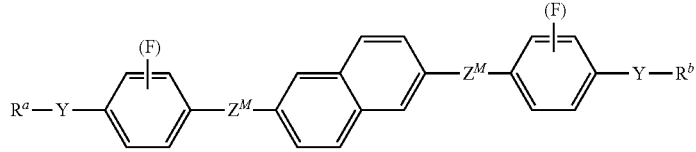
(M1-28)
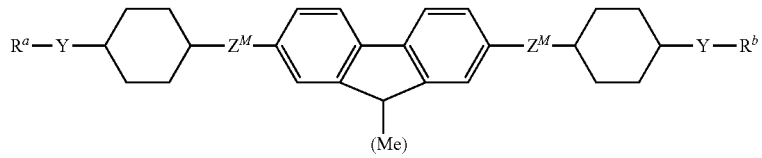
(M1-29)
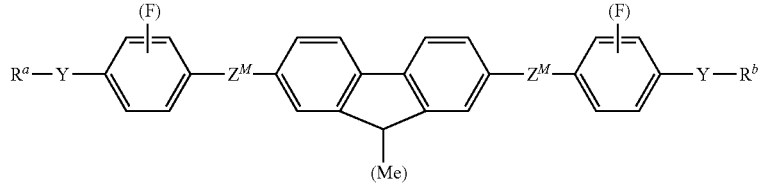
(M1-30)
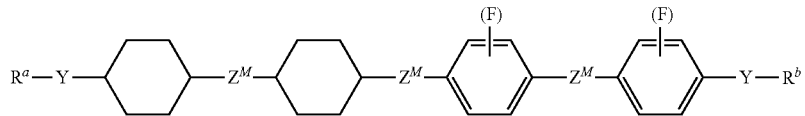
(M1-31)
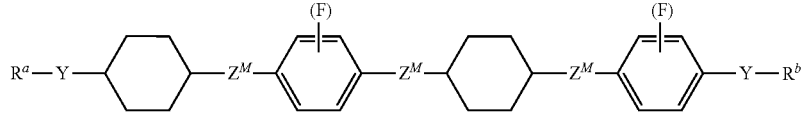
(M1-32)
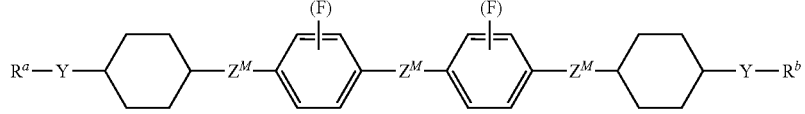
(M1-33)
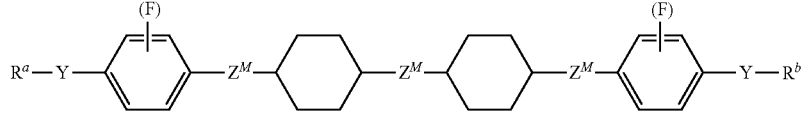
(M1-34)
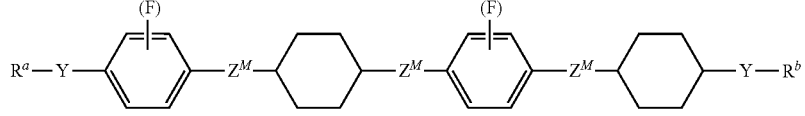
(M1-35)
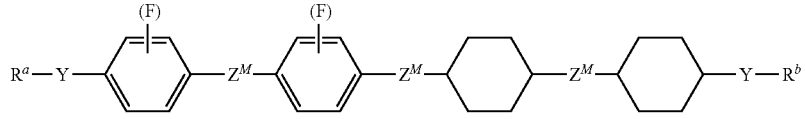
(M1-36)

(M1-37) 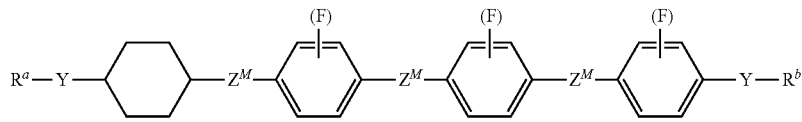
(M1-38) 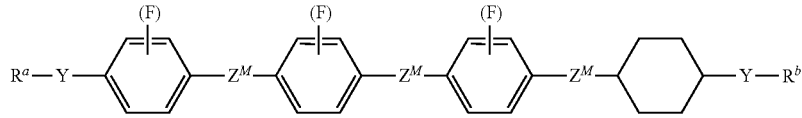
(M1-39) 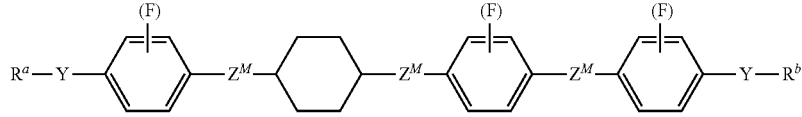
(M1-40) 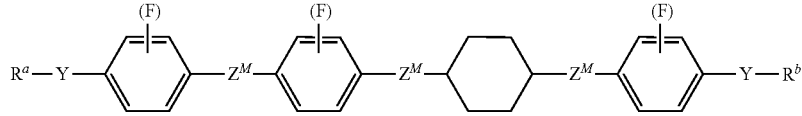
(M1-41) 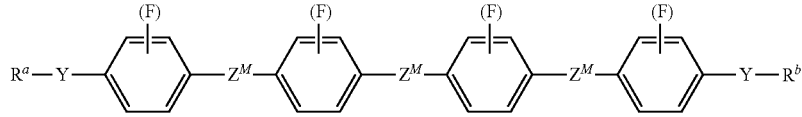
(M2-1) 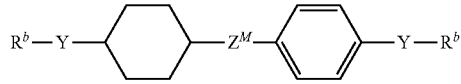
(M2-2) 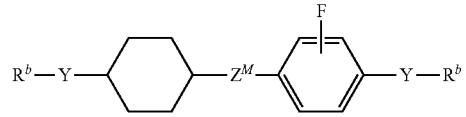
(M2-3) 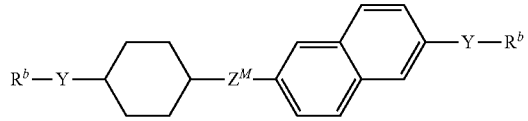
(M2-4) 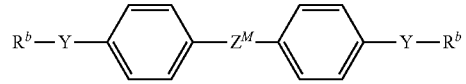
(M2-5) 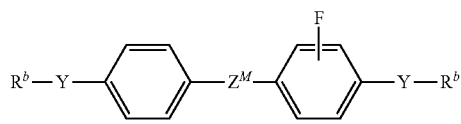
(M2-6) 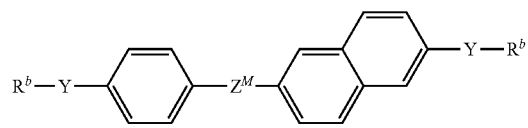
(M2-7) 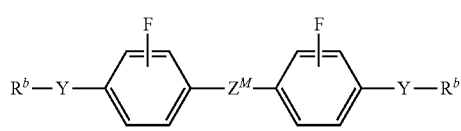
(M2-8) 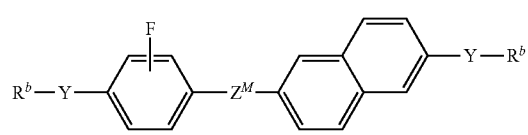
(M2-9) 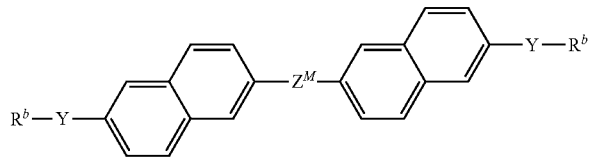
(M2-10) 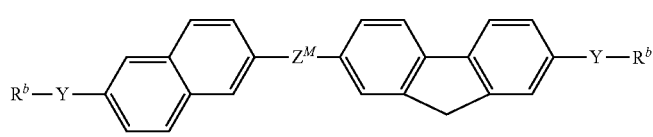

-continued
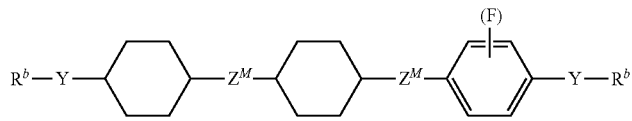
(M2-11)
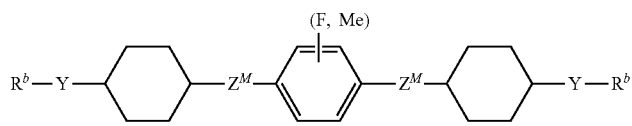
(M2-12)
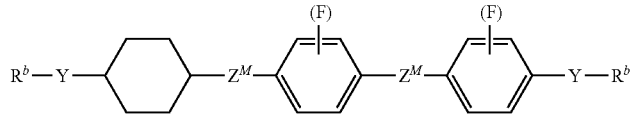
(M2-13)
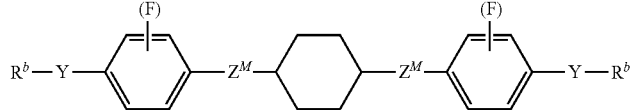
(M2-14)
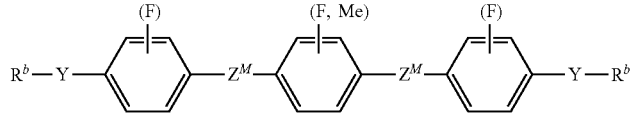
(M2-15)
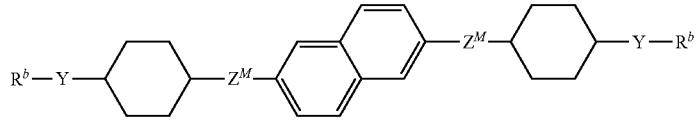
(M2-16)
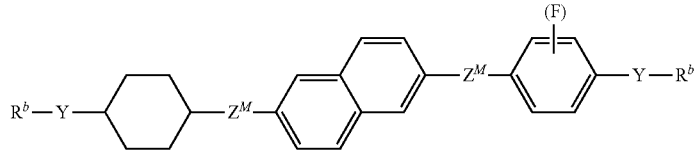
(M2-17)
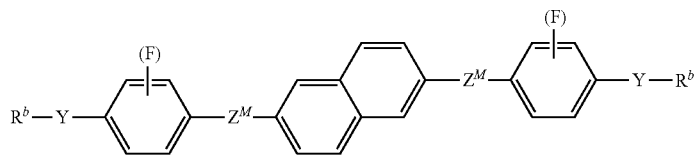
(M2-18)
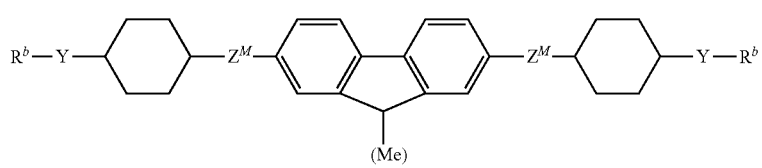
(M2-19)
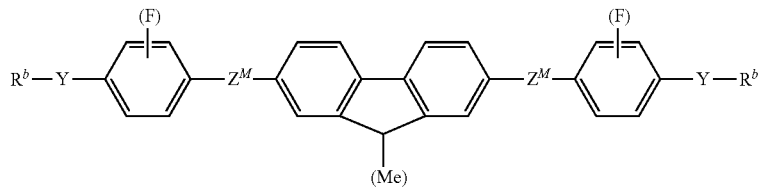
(M2-20)
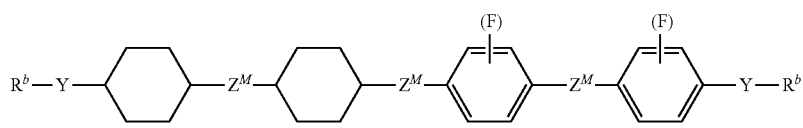
(M2-21)

-continued

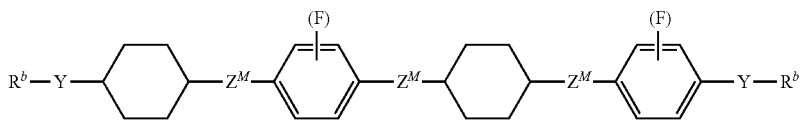
(M2-22)

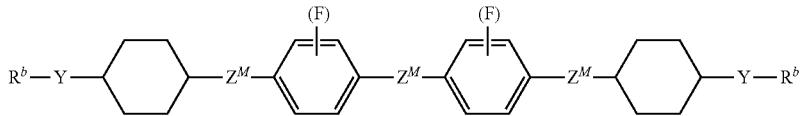
(M2-23)

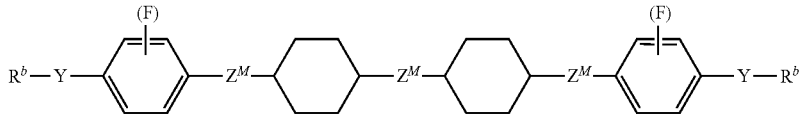
(M2-24)

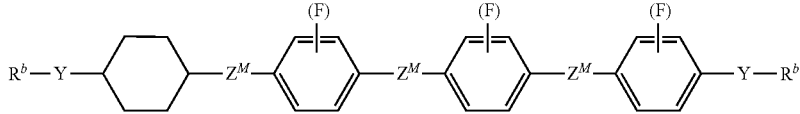
(M2-25)

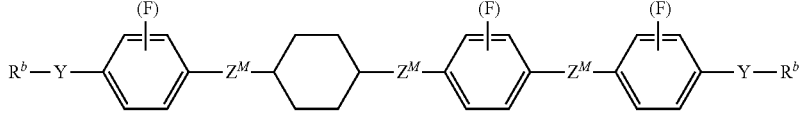
(M2-26)

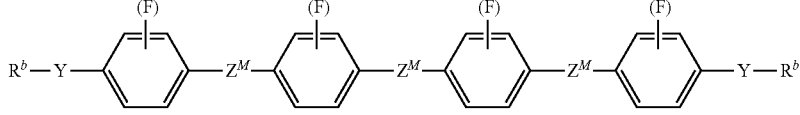
(M2-27)

A polymerizable compound other than the monomer having no mesogen moiety and the monomers (M1) and (M2) having mesogen moiety may be used, if desired.

In order to optimize the optical isotropy of the polymer/liquid crystal composite material of the present invention, a monomer having a mesogen moiety and three or more polymerizable functional groups can also be used. The monomer having a mesogen moiety and three or more polymerizable functional groups is preferably a well-know compound, for example, (M4-1)-(M4-3), and more specifically, the compounds described in Japanese Patent Publication Nos. 2000-327632, 2004-182949, and 2004-59772. In (M4-1)-(M4-3), $R^b$, $Z^m$, Y, and (F) have the same meaning as described above.

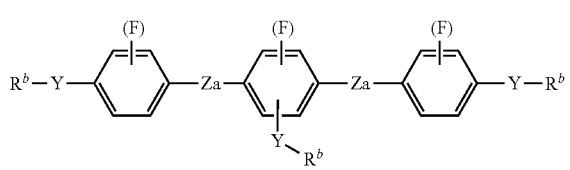
(M4-1)

(M4-2)

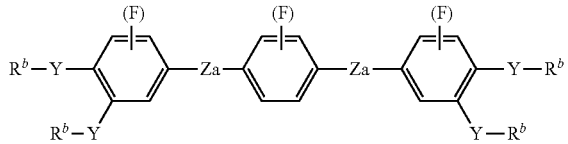
(M4-3)

5-1-2 Monomer Having No Mesogen Moiety and Having Polymerizable Functional Group Examples of the monomer having no mesogen moiety and having a polymerizable group are linear or branched acrylate of 1-30 carbons, linear or branched diacrylate of 1-30 carbons, and a monomer having three or more polymerizable groups, for example, but not limited to, glycerol-propoxide (1PO/OH) triacrylate, pentaerythritol-propoxide triacrylate, pentaerythritol triacrylate, trimethylolpropane-ethoxide triacrylate, trimethylolpropane-propoxide triacrylate, trimethylolpropane triacrylate, di(trimethylolpropane)tetraacrylate, pentaerythritol tetraacrylate, di(pentaerythritol)pentaacrylate, di(pentaerythritol) hexaacrylate, and trimethylolpropane triacrylate.

5-1-3 Polymerization Initiator

The polymerization pattern used to produce the polymer compound for forming the composite material of the present invention has no particular limitation, and may be, for example, photo-radical polymerization, thermo-radical polymerization, and photo-cationic polymerization.

The photo-radical polymerization initiator useful for photo-radical polymerization is, for example, DAROCUR™ 1173 and 4265 (both are trade names, from Ciba Specialty Chemicals); and IRGACURE™ 184, 369, 500, 651, 784, 819, 907, 1300, 1700, 1800, 1850, and 2959 (all are trade names, from Ciba Specialty Chemicals).

Preferred examples of the thermo-radical polymerization initiators useful in thermo-radical polymerization are benzoyl peroxide, diisopropyl peroxydicarbonate, tert-butyl peroxy (2-ethylhexanoate), tert-butyl peroxypivalate, tert-butyl peroxydiisobutyrate, lauroyl peroxide, dimethyl 2,2'-azobisisobutyrate (MAIB), di-t-butyl peroxide (DTBPO), azobisisobutyronitrile (AIBN), and azobiscyclohexanecarbonitrile (ACN), and the like.

Examples of the photo-cationic polymerization initiator useful for photo-cationic polymerization are diaryliodonium salt (referred to as "DAS", hereafter), and triarylsulfonium salt (referred to as "TAS", hereafter), and the like.

Examples of DAS are diphenyliodonium tetrafluoroborate, diphenyliodonium hexafluorophosphate, diphenyliodonium hexafluoroarsenate, diphenyliodonium trifluoromesylate, diphenyliodonium trifluoroacetate, diphenyliodonium p-toluenesulfonate, diphenyliodonium tetrakis(pentafluorophenyl)borate, 4-methoxyphenylphenyliodonium tetrafluoroborate, 4-methoxyphenylphenyliodonium hexafluorophosphate, 4-methoxyphenylphenyliodonium hexafluoroarsenate, 4-methoxyphenylphenyliodonium trifluoromesylate, 4-methoxyphenylphenyliodonium trifluoroacetate, and 4-methoxyphenylphenyliodonium p-toluenesulfonate.

DAS may be sensitized by adding a photosensitizer, such as thioxanthone, phenothiazine, chlorothioxanthone, xanthone, anthracene, diphenyl anthracene, and rubrene.

Examples of TAS are triphenylsulfonium tetrafluoroborate, triphenylsulfonium hexafluorophosphate, triphenylsulfonium hexafluoroarsenate, triphenylsulfonium trifluoromesylate, triphenylsulfonium trifluoroacetate, triphenylsulfonium p-toluenesulfonate, triphenylsulfonium tetrakis(pentafluorophenyl)borate, 4-methoxyphenyldiphenylsulfonium tetrafluoroborate, 4-methoxy phenyldiphenylsulfonium hexafluorophosphate, 4-methoxyphenyldiphenylsulfonium hexafluoroarsenate, 4-methoxyphenyldiphenylsulfonium trifluoromesylate, 4-methoxyphenyldiphenylsulfonium trifluoroacetate, and 4-methoxyphenyldiphenylsulfonium p-toluenesulfonate, and the like.

Specific examples of the photo-cationic polymerization initiator are Cyracure™ UVI-6990, Cyracure UVI-6974, and Cyracure UVI-6992 (all are trade names, from UCC Corporation); Adeka Optomer SP-150, SP-152, SP-170, and SP-172 (all are trade names, from ADEKA Corporation); Rhodorsil Photoinitiator 2074 (trade name, from RHODIA JAPAN Corporation); IRGACURE™ 250 (trade name, from Ciba Specialty Chemicals); and UV-9380C (trade name, from GE TOSHIBA SILICONES Co. Ltd), and the like.

5.1.4 Curing Agents and Others

In preparing the polymer compound for forming the composite material of the present invention, in addition to the monomers and the polymerization initiator above, one or two or more other preferred components, such as, curing agent, catalyst, and stabilizer, may also be further added.

The latent curing agents well-known in the art which are commonly used as curing agent for epoxy resins may be used. Examples of the latent curing agent for epoxy resins are amine-based curing agents, novolac-based curing agents, imidazole-based curing agents, and anhydride-based curing agents, and the like. Examples of amine-based curing agents are aliphatic polyamines such as diethylenetriamine, triethylenetetraamine, tetraethylenepentaamine, m-xylenediamine, trimethyl hexamethylenediamine, 2-methyl pentamethylenediamine, and diethylaminopropylamine; alicyclic polyamines such as isophorone diamine, 1,3-diaminomethylcyclohexane, bis(4-aminocyclohexyl)methane, norbornanediamine, 1,2-diaminocyclohexane, and Laromin; and aromatic polyamines such as diaminodiphenylmethane, diaminodiphenylethane, and m-phenylenediamine.

Examples of novolac-based curing agents are phenol-novolac resin, and bisphenol-novolac resin, and the like. Examples of imidazole-based curing agents are 2-methylimidazole, 2-ethylhexylimidazole, 2-phenylimidazole, and 1-cyanoethyl-2-phenylimidazolium trimellitate, and the like.

Examples of anhydride-based curing agents are tetrahydrophthalic anhydride, hexahydrophthalic anhydride, methyltetrahydrophthalic anhydride, methylhexahydrophthalic anhydride, methylcyclohexene tetracarboxylic dianhydride, phthalic anhydride, trimellitic anhydride, pyromellitic dianhydride, and benzophenone tetracarboxylic dianhydride, and the like.

Furthermore, a curing accelerator may further be used to facilitate the curing reaction of a polymerizable compound with glycidyl, epoxy, or oxetanyl and the curing agent. Examples of the curing accelerator are tertiary amines such as benzyldimethylamine, tris(dimethylaminomethyl)phenol, and dimethylcyclohexylamine; imidazoles such as 1-cyanoethyl-2-ethyl-4-methylimidazole, and 2-ethyl-4-methylimidazole; organophosphorus compounds such as triphenylphosphine; quaternary phosphosium salts such as tetraphenylphosphosium bromide; diazobicyclo alkenes such as 1,8-diazobicyclo[5.4.0]undecene-7 or an organic acid salt thereof; quaternary ammonium salts such as tetraethylammonium bromide, and tetrabutylammonium bromide; boron compounds such as boron trifluoride, and triphenyl borate, and the like. These curing accelerators may be used alone, or in a combination of two or more.

Moreover, a stabilizer is preferably added, for example, to prevent unwanted polymerization during storage. The stabilizer may be any compound well known to those of ordinary skill in the art, representative examples of which are 4-ethoxyphenol, hydroquinone, and butylated hydroxytoluene (BHT), and the like.

5-2 Content of Liquid Crystal Composition

The content of the liquid crystal composition in the polymer/liquid crystal composite material of the present invention is preferably as high as possible, so long as it is within a range in which the composite material exhibits an optically isotropic liquid crystal phase. The reason lies in the fact that the higher the content of the liquid crystal composition is, the greater the electrically controlled birefringence value of the composite material of the present invention is.

In the polymer/liquid crystal composite material of the present invention, the content of the liquid crystal composition is preferably 60-99 wt %, more preferably 60-95 wt %, and particularly preferably 65-95 wt %, with respect to the composite material. The content of the polymer compound is preferably 1-40 wt %, more preferably 5-40 wt %, and particularly preferably 5-35 wt %, with respect to the composite material.

5-3 Other Components

The polymer/liquid crystal composite material of the present invention may also contain, for example, a dichroic dye and a photochromic compound, without prejudice to the effect of the present invention.

The present invention is further described in detail with reference to examples; however, the present invention is not limited to thereto. Furthermore, "%" denotes "wt %", unless specifically indicated.

6 Optical Device

A sixth aspect of the present invention is an optical device, which contains the liquid crystal composition or the polymer/liquid crystal composite material (hereafter, both are sometimes collectively referred to as liquid crystal medium) and is driven in an optically isotropic liquid crystal phase.

The liquid crystal medium is optically isotropic in the absence of an electric field and exhibits an optical anisotropy in the presence of an electric field, such that optical modulation may be achieved with an electric field.

As an example of the structure of the LCD device, as shown in FIG. 1, the electrodes on the comb-like electrode substrate have such a structure that Electrode 1 extending from the left side and Electrode 2 extending from the right side are alternatively arranged. When a potential difference exists between Electrode 1 and Electrode 2, the comb-like electrode substrate is provided with an electric field in two directions (upward and downward), as shown in FIG. 1.

EXAMPLES

The resulting compound is characterized by a nuclear magnetic resonance (NMR) spectrum obtained by $^1$H-NMR analysis and a gas chromatogram obtained by gas chromatography (GC) analysis. The analysis methods are firstly illustrated below.

$^1$H-NMR analysis: $^1$H-NMR analysis was carried out by using DRX-500 (manufactured by Bruker BioSpin Co., Ltd). In the measurement, a sample prepared in an Example was dissolved in a deuterated solvent, such as $CDCl_3$, which is capable of dissolving the sample, and then was measured with a NMR apparatus at 500 MHz at room temperature in 24 times of accumulation. In the resulting NMR spectrum, s denotes singlet, d denotes doublet, t denotes triplet, q denotes quartet, and m denotes multiplet. Furthermore, tetramethylsilane (TMS) was used as the standard of chemical shift $\delta$ of zero.

GC analysis: GC analysis was carried out by using a GC apparatus Model GC-14B (manufactured by Shimazu). The column was the capillary column CBP1-M25-025 (length=25 m, inner diameter=0.22 mm, film thickness=0.25 manufactured by Shimazu); and the stationary liquid phase was polydimethylsiloxane (non-polarity). The carrier gas was helium, and the flow rate was adjusted to 1 ml/min. The sample evaporation chamber was set at 300° C., and the detector (flame ionization detector, FID) was set at 300° C.

A sample was dissolved in toluene to give a solution of 1 wt %, and then 1 of the solution was injected into the sample evaporation chamber.

The recorder used was Chromatopac Model C-R6A (manufactured by Shimazu) or an equivalent thereof. The resulting gas chromatogram exhibited peak retention times and peak areas corresponding to the component compounds.

In addition, the solvent for diluting the sample was, for example, chloroform or hexane. The column used was, for example, capillary column DB-1 (length=30 m, inner diameter=0.32 mm, film thickness=0.25 μm, manufactured by Agilent Technologies Inc.), HP-1 (length=30 m, inner diameter=0.32 mm, film thickness=0.25 p.m., manufactured by Agilent Technologies Inc.), Rtx-1 (length=30 m, inner diameter=0.32 mm, film thickness=0.25 μm, manufactured by Restek Corporation), or BP-1 (length=30 m, inner diameter=0.32 mm, film thickness=0.25 μm, manufactured by SGE International Pty. Ltd.).

The area ratios of the peaks in the gas chromatogram correspond to the ratios of the component compounds. Generally, the weight percentages of the component compounds in the analyzed sample are not completely identical to the area percentages of the peaks. However, in the present invention, when the columns described above are used, the correction coefficient is substantially 1. Therefore, the weight percentages of the component compounds in the analyzed sample are substantially corresponding to the area percentages of the peaks. The reason lies in that there is no significant difference among the correction coefficients of the component compounds. In order to more accurately calculate the ratios of the liquid crystal compounds in the liquid crystal composition with GC, the internal standard method for GC may be used. GC measurements were simultaneously performed on an accurately weighed specified amount of a liquid crystal compound component (detected component) and a liquid crystal compound as standard (standard), and the relative intensity was previously calculated as peak area ratio of the detected component to the standard. If a correction was performed by using the relative intensity expressed as peak area ratio of each component to the standard, then the ratios of the liquid crystal compounds in the liquid crystal composition can be more accurately calculated with GC analysis.

Samples for determining characteristic values of liquid crystal compounds

Two methods may be used to measure the characteristic values of a liquid crystal compound, i.e., taking a pure compound as a sample, or mixing a compound in a mother liquid crystal to form a sample.

When a sample prepared by mixing a compound with a mother liquid crystal is used, the following method is used for the measurement. Firstly, 15 wt % of the resulting liquid crystal compound was mixed with 85 wt % of the mother liquid crystal to prepare a sample, and then an extrapolated value is calculated from the measured value of the sample according to the extrapolation method based on the equation below, as the characteristic value of the compound.

[Extrapolated Value]=(100×[measured value of the sample]−[wt % of the mother liquid crystal]× [measured value of the mother liquid crystal])/ [wt % of the liquid crystal compound]

While the liquid crystal compound and the mother liquid crystal are at this ratio, when it is in a smectic phase or a crystal is precipitated at 25° C., the ratio of the liquid crystal compound and the mother liquid crystal can also be changed to be 10 wt %:90 wt %, 5 wt %:95 wt %, 1 wt %:99 wt % in order, such that the characteristic value of the sample is determined with a composition where it is in a smectic phase or a composition where a crystal is not precipitated again at 25° C., and an extrapolated value is calculated according to the equation above, as the characteristic value of the liquid crystal compound.

There are numerous mother liquid crystals that may be used for the measurement. For example, the composition of the mother liquid crystal A is as follows (wt %).

Mother Liquid Crystal A:

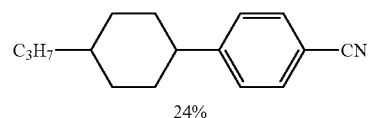

24%

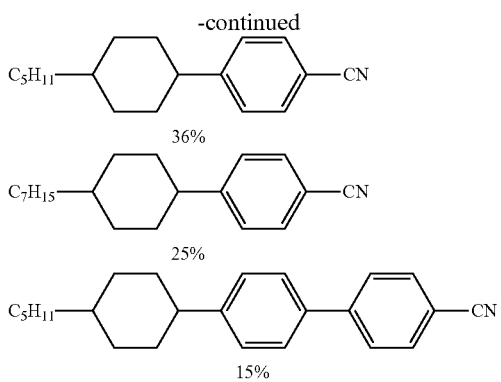

Method for Measuring Characteristic Values of Liquid Crystal Compounds

The measurement of the characteristic values was carried out with the methods below. These methods are mainly those described in EIAJ•ED-2521A of the Standard of Electric Industries Association of Japan, or modifications of the same. Moreover, the TN device used in the measurement was not equipped with TFT.

With respect to the determined values, in case that the liquid crystal compound itself is used as a sample, the obtained values are recorded as experimental data; and in case that a mixture of the liquid crystal compound and a mother liquid crystal is used as a sample, the extrapolated values obtained with the extrapolation method are recorded as experimental data.

The phase structure and the phase transition temperature (° C.) were measured by using the methods (1) and (2) below.

(1) A compound was placed on a heating plate (Hot Stage, Model FP-52, manufactured by Mettler, Corp.) in a melting point measuring apparatus equipped with a polarizing microscope, and the phase behaviour and its change were observed by the polarizing microscope while the sample was heated at a rate of 3° C./min, to determine the type of the liquid crystal phase.

(2) A scanning calorimetry DSC-7 system or Diamond DSC system (manufactured by PerkinElmer Corp.) was used, at a heating or cooling rate of 3° C./min, and the on set of the endothermic peak or the exothermic peak along with the phase change of the sample was calculated with the extrapolation method, to determine the phase transition temperature.

Hereafter, a crystal is expressed as K, and for distinguishing, two crystals are expressed as $K_1$ or $K_2$, respectively. A smectic phase is expressed as Sm, a nematic phase is expressed as N, and a liquid (isotropic phase) is expressed as I. For distinguishing, a smectic B phase and a smectic A phase in the smectic phase are expressed as SmB and SmA, respectively. BP represents a blue phase or an optically isotropic liquid crystal phase. A biphase co-existence is sometimes expressed as (N*+I) or (N*+BP). Specifically, (N*+I) represents a phase in which a non-liquid crystal isotropic phase and a chiral nematic phase coexist, and (N*+BP) represents a phase in which a BP phase or an optically isotropic liquid crystal phase and a chiral nematic phase coexist. Un represents a non-optically isotropic unidentified phase. For the expression of the phase transition temperature, for example, "K 50.0 N 100.0 I" means that the phase transition temperature (KN) from the crystal to the nematic phase is 50.0° C., and the phase transition temperature (NI) from the nematic phase to the liquid is 100.0° C. This rule is also applicable to other expressions.

Upper-limit temperature of a nematic phase ($T_{NI}$, ° C.): a sample (a mixture of a liquid crystal compound and a mother liquid crystal) was placed on a heating plate (Hot Stage, Model FP-52, manufactured by Mettler Corp.) in a melting point measuring apparatus equipped with a polarizing microscope, and was observed with the polarizing microscope while the sample was heated at a rate of 1° C./min. The temperature at which a part of the sample began to change from a nematic phase into an isotropic liquid was recorded as the upper-limit temperature of the nematic phase, sometimes abbreviated as "upper-limit temperature" below.

Low-temperature compatibility: samples were prepared by mixing a mother liquid crystal with a liquid crystal compound in such a manner that the content of the latter was 20 wt %, 15 wt %, 10 wt %, 5 wt %, 3 wt %, and 1 wt %, respectively, and then placed into glass bottles. The glass bottles were kept in a freezer at −10° C. or −20° C. for a specified period of time, and the presence or absence of a crystal or a smectic phase was observed.

Viscosity ($\eta$, determined at 20° C., mPa·s): the viscosity of a mixture of a liquid crystal compound and a mother liquid crystal is measured with an E-type rotational viscometer.

Optical anisotropy ($\Delta n$): the measurement was carried out at 25° C. by using light having a wavelength of 589 nm, with an Abbe refractometer having a polarizing plate mounted on an ocular lens. After the surface of the main prism is rubbed in a direction, a sample (a mixture of a liquid crystal compound and a mother liquid crystal) was dripped onto the main prism. The refractive index ($n_\parallel$) was determined when the polarizing direction was paralleled to the rubbing direction, and the refractive index ($n_\perp$) was determined when the polarizing direction was perpendicular to the rubbing direction. The value of optical anisotropy ($\Delta n$) was calculated according to the equation $\Delta n = n_\parallel - n_\perp$.

Dielectric anisotropy ($\Delta \epsilon$: determined at 25° C.): a sample (a mixture of a liquid crystal compound and a mother liquid crystal) was fed into a liquid crystal cell with a distance (cell gap) of about 9 pin between two glass substrates and a twist angle of 80 degrees. The liquid crystal cell was applied with a voltage of 20 V and the dielectric constant ($\epsilon_\parallel$) in the major-axis direction of the liquid crystal molecule was determined. Then, a voltage of 0.5 V was applied and the dielectric constant ($\epsilon_\perp$) in the minor axis direction of the liquid crystal molecule was determined. The value of dielectric anisotropy was calculated according to the equation $\Delta \epsilon = \epsilon_\parallel - \epsilon_\perp$.

Pitch (P, determined at 25° C., nm)

A pitch length was measured through selective reflection (Handbook of Liquid Crystal, p 196, 2000, Maruzen). For the selective reflection wavelength $\lambda$, the relationship $<n>p/\lambda=1$ exists. Here, $<n>$ denotes the average refractive index, and is calculated according to the equation $<n>=\{(n_\parallel^2+n_\perp^2)/2\}^{1/2}$. The selective reflection wavelength was determined by a microspectrophotometer (Trade name MSV-350, manufactured by Japan Electronics Co., Ltd.). The pitch was calculated by dividing the resulting reflection wavelength by the average refractive index. When the concentration of the optically active compound is low, the pitch of a cholesteric liquid crystal having a reflection wavelength in a region of wavelength longer than that of visible light is proportional to the reciprocal of the concentration. Therefore, multiple points were measured for the pitch length of the liquid crystal having a selective reflection wavelength in the visible light region, and then the pitch was calculated by using a linear extrapolation method. The "optically active compound" is equivalent to the chiral dopant in the present invention.

Synthesis Example 1

Synthesis of Formula (S1-10)

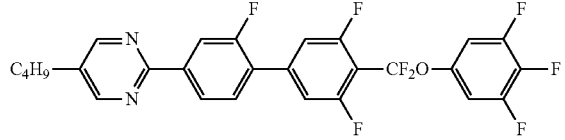
(S1-10)

The synthesis scheme is as shown below.

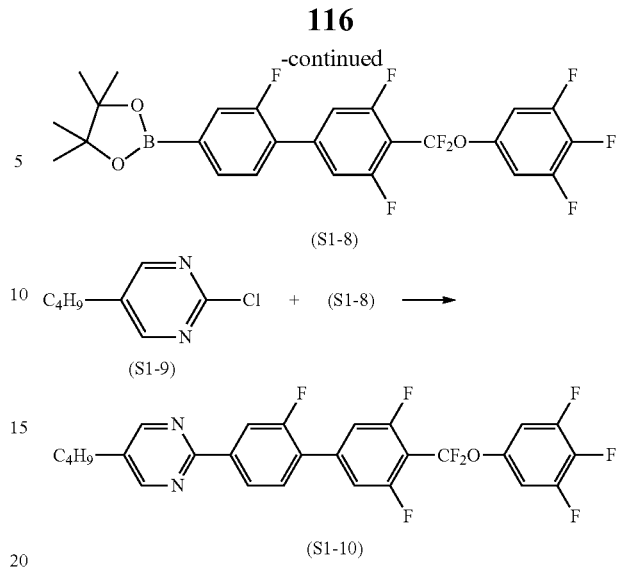

Synthesis of Compound (S1-4)

4.0 g (S1-1) and 20 ml a mixed solvent of toluene/isooctane=1/1 were charged into a reactor, 1.43 g 1,3-malonyl thiol (S1-2) was added thereto, and the mixture was stirred for 30 min. Next, the reaction solution was warmed to 60° C., 3.99 g Trifluoromethanesulfonic Acid (S1-3) was dropped, and the resulting solution was stirred at 60° C. for 1 h and then stirred at 90° C. for 2 h. Then, the reaction solution was cooled to room temperature, and distilled under reduced pressure to remove the solvent, tert-butyl methyl ether is added, and the solution was filtrated. The resulting solid component was dried, to obtain 4.30 g Compound (S1-4).

Synthesis of Compound (S1-6)

1.38 g 3,4,5-trifluorophenol (S1-5), 1.02 g triethylamine, 20 ml dichloromethane were charged into a reactor under nitrogen atmosphere, and the mixture was cooled to −70° C. Next, a mixture of 4.30 g (S1-4) and 20 ml dichloromethane was dropped, and the reaction solution was stirred for 1 h. Then, 2.78 g triethylamine tris(hydrogen fluoride) was dropped, and the reaction solution was stirred for 30 min, and then 6.22 g bromine was dropped and stirred for 1 h. The reaction solution was slowly warmed to 0° C., and slowly added into 100 ml water. Sodium bicarbonate was slowly added into the mixture, to adjust the aqueous phase to be neutral, and the organic phase was washed with water and then dried over sodium sulphate. The resulting solution was distilled at reduced pressure to remove the solvent, and the residue component was purified by silica-gel column chromatography with heptane as eluent, to obtain 2.10 g (S1-6). The yield of (S1-6) from (S1-1) is 36.0%.

Synthesis of Compound (S1-8)

1.70 g (S1-6), 1.07 g (S1-7), 1.03 g potassium acetate, 0.061 g tetrakis(triphenylphosphine) palladium, and 20 ml dioxane were charged into a reactor under nitrogen atmosphere, and then the mixture was stirred at 80° C. for 2 h. Next, the reaction solution was cooled to room temperature, and 50 ml toluene was added thereto, and the organic phase was washed with water, dried over sodium sulphate, and then distilled at reduced pressure to remove the solvent. The residue component was purified by silica-gel column chromatography with a mixed solvent of toluene/ethyl acetate=10/1 as eluent, and then dried at reduced pressure, to obtain about 2 g (S1-8).

Synthesis of Compound (S1-10)

About 2 g Compound (S1-8), 0.65 g Compound (S1-9), 1.60 g potassium phosphate, 0.04 g tetrakis(triphenylphosphine) palladium, 30 ml Solmix were charged into a reactor under nitrogen atmosphere, and the mixture was stirred at 70° C. for 2 h. Next, the reaction solution was cooled to room temperature, 50 ml toluene was added thereto, and the organic phase was washed with water, dried over sodium sulphate, and then distilled at reduced pressure to remove the solvent. The residue component was purified by silica-gel column chromatography with a mixed solvent of heptane/toluene=1/1 as eluent, dried at reduced pressure, and then recrystallized from a mixed solvent of heptane/ethanol=1/1, to obtain 1.02 g (S1-10). The yield of (S1-10) from (S1-6) is 54.3%.

The phase transition temperature of the resulting Compound (S1-10) is as follows.

Phase transition temperature (° C.): K 77.1 SmA 116.7 N 140.2 I

The resulting compound was identified to be (S1-10) through the following chemical shift δ (ppm) obtained with $^{1}$H-NMR analysis using CDCl$_{3}$ as solvent. Chemical shift δ (ppm): 8.66 (s, 2H), 8.31 (ddd, 2H), 7.54 (t, 1H), 7.29 (d, 2H), 7.00-6.98 (m, 2H), 2.67 (t, 2H), 1.69-1.64 (m, 2H), 1.44-1.40 (m, 2H), 0.97 (t, 3H).

Physical properties of Liquid Crystal Compound (S1-10)

The four compounds designated as mother liquid crystal A above were mixed, to prepare a mother liquid crystal A having a nematic phase. The physical properties of the mother liquid crystal A are as follows.

Upper-limit temperature ($T_{NI}$)=71.7° C., dielectric anisotropy ($\Delta\in$)=11.0, and optical anisotropy ($\Delta$n)=0.137.

A liquid crystal composition B containing 85 wt % of the mother liquid crystal A and 15 wt % of (S1-10) obtained in Example 1 was prepared. The characteristic values of the resultant liquid crystal composition B were determined. The extrapolated characteristic values of the Liquid Crystal Compound (S1-10) were calculated from the measured values using an extrapolation method, and the extrapolated values are as follows.

Upper-limit temperature ($T_{NI}$)=102.4° C., dielectric anisotropy ($\Delta\in$)=50.3, optical anisotropy ($\Delta$n)=0.197.

It can be known from the results that, the Liquid Crystal Compound (S1-10) has a high clearing point, is well soluble with other liquid crystal compounds, and has a large dielectric anisotropy (As) and optical anisotropy ($\Delta$n).

According to the method of Synthesis Example 1, Compounds (S2) and (S3) are synthesized.

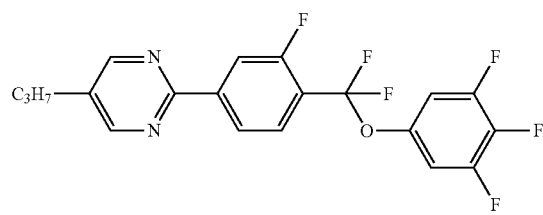

(S2)

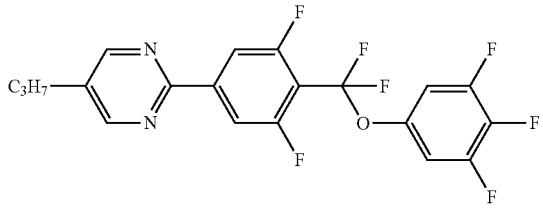

(S3)

The phase transition temperature of the resulting Compound (S2) is as follows.

Phase transition temperature (° C.): K 56.6 I

Physical properties of Liquid Crystal Compound (S2)

A liquid crystal composition C containing 85 wt % of the mother liquid crystal A and 15 wt % of (S2) was prepared. The characteristic values of the resultant liquid crystal composition C were determined. The extrapolated characteristic values of the Liquid Crystal Compound (S2) were calculated from the measured values using an extrapolation method, and the extrapolated values are as follows.

Upper-limit temperature ($T_{NI}$)=34.4° C., dielectric anisotropy ($\Delta\in$)=40.4, optical anisotropy ($\Delta$n)=0.137.

It can be known from the results that, Liquid Crystal Compound (S2) is well soluble with other liquid crystal compounds, and has a large dielectric anisotropy (As) and optical anisotropy ($\Delta$n).

The phase transition temperature of the resulting Compound (S3) is as follows.

Phase transition temperature (° C.): K 53.6 I

Physical properties of liquid crystal compound (S3)

A liquid crystal composition D containing 85 wt % of the mother liquid crystal A and 15 wt % of (S3) was prepared. The characteristic values of the resultant liquid crystal composition D were determined. The extrapolated characteristic values of the Liquid Crystal Compound (S3) were calculated from the measured values using an extrapolation method, and the extrapolated values are as follows.

Upper-limit temperature ($T_{NI}$)=10.4° C., dielectric anisotropy ($\Delta\in$)=43.7, optical anisotropy ($\Delta$n)=0.124.

It can be known from the results that, Liquid Crystal Compound (S3) is well soluble with other liquid crystal compounds, and has a large dielectric anisotropy ($\Delta\in$) and optical anisotropy ($\Delta$n).

(Composition of the Present Invention)

In the present invention, the characteristic values of the liquid crystal composition were measured according to the methods below. The methods are mainly those described in EIAJ•ED-2521A of the Standard of Electric Industries Association of Japan, or modifications of the same. The TN device used in the measurement was not equipped with TFT.

Upper-limit temperature of a nematic phase (NI, ° C.): a sample was placed on a heating plate in a melting point measuring apparatus equipped with a polarizing microscope, and heated at a rate of 1° C./min. The temperature at which a part of the sample began to change from a nematic phase into an isotropic liquid was recorded as the upper-limit temperature of the nematic phase, which is sometimes abbreviated as "upper-limit temperature".

Lower-limit temperature of a nematic phase ($T_c$, ° C.): a sample having a nematic phase was kept in a freezer at 0° C., −10° C., −20° C., −30° C., and −40° C. for 10 days, and observed for the liquid crystal phase. For example, in a case where the sample exhibits a nematic phase at −20° C., and is changed to a crystal or a smectic phase at −30° C., the $T_C$ is recorded as ≦20° C. The lower-limit temperature of a nematic phase is sometimes abbreviated as "lower-limit temperature".

Transition temperature of an optically isotropic liquid crystal phase: a sample was placed on a heating plate in a melting point measuring apparatus equipped with a polarizing microscope, and in a crossed nicols state, initially heated to a temperature allowing the sample to change into a non-liquid crystal isotropic phase, and then cooled at a rate of 1° C./min until a chiral nematic phase or an optically isotropic liquid crystal phase was completely formed. The phase transition temperature during this cooling process was measured. Then, the temperature was raised at a rate of 1° C./min, and the phase transition temperature during this heating process was measured. In the present invention, unless specifically indicated, the phase transition temperature in the heating process was recorded as the phase transition temperature. Where it was difficult to determine the phase transition temperature of the optically isotropic liquid crystal phase in a dark field under crossed nicols, the phase transition temperature could be determined after the polarizing plate is deviated from the crossed polarization state by 1-10 degrees.

Viscosity ($\eta$, determined at 20° C., mPa·s): the viscosity was measured with an E-type rotational viscometer.

Rotational viscosity ($\gamma 1$, determined at 25° C., mPa·s):

1) For a sample with a positive dielectric anisotropy: the measurement was carried out according to the method described in M. Imai et al., *Molecular Crystals and Liquid Crystals*, Vol. 259, 37 (1995). The sample was placed into a TN device with a twist angle of 0 degree and a distance (cell gap) of 5 μm between two glass substrates. The TN device was applied with a voltage in a range of 16 to 19.5 V stepwise by 0.5 V. After a period of 0.2 s without voltage application a voltage application was repeated with a rectangular wave (rectangular pulse of 0.2 s) followed by a period of 2 s without voltage application. The peak current and the peak time of the transient current resulted from the application of the voltage were measured. Then, the value of rotational viscosity was calculated according to the measurements and the Equation (8) described on page 40 of the paper of M. Imai et al. The dielectric anisotropy value required for this calculation was obtained by using the device used in the measurement of the rotational viscosity, according to the method for determining dielectric anisotropy below.

2) For a sample with a negative dielectric anisotropy: the measurement was carried out according to the method described in M. Imai et al., *Molecular Crystals and Liquid Crystals*, Vol. 259, 37 (1995). The sample was placed into a vertical alignment (VA) device with a distance (cell gap) of 20 μm between two glass substrates. The device was applied with a voltage in a range of 30 to 50 V stepwise by 1 V. After a period of 0.2 s without voltage application, a voltage application was repeated with a rectangular wave (rectangular pulse of 0.2 s) followed by a period of 2 s without voltage application. The peak current and the peak time of the transient current resulted from the application of the voltage were measured. Then, the value of rotational viscosity was calculated according to the measurements and the Equation (8) described on page 40 of the paper of M. Imai et al. The dielectric anisotropy value required for this calculation was obtained by using the method for determining dielectric anisotropy below.

Optical anisotropy ($\Delta n$, determined at 25° C.): the measurement was carried out by using light having a wavelength of 589 nm, with an Abbe refractometer having a polarizing plate mounted on the ocular lens. After the surface of the main prism was rubbed in a direction, the sample was dropped onto the main prism. The refractive index ($n_{\parallel}$) was determined when the polarizing direction was paralleled to the rubbing direction, and the refractive index ($n_{\perp}$) was determined when the polarizing direction was perpendicular to the rubbing direction. The value of optical anisotropy was calculated according to the equation $\Delta n = n_{\parallel} - n_{\perp}$. When the sample was a composition, the process could be used to determine the optical anisotropy. When the sample was a compound, the compound was mixed with a suitable composition for determining the optical anisotropy. In this case, the optical anisotropy value of the compound was an extrapolated value.

Dielectric anisotropy ($\Delta \in$, determined at 25° C.): when the sample was a compound, the compound was mixed with a suitable composition for determining the dielectric anisotropy. In this case, the dielectric anisotropy value of the compound was an extrapolated value.

1) For a composition with a positive dielectric anisotropy: a sample was placed into a liquid crystal cell with a distance (gap) of about 9 μm between two glass substrates and a twist angle of 80 degrees. The liquid crystal cell was applied with a voltage of 20 V to determine the dielectric constant ($\in_{\parallel}$) in the major axis direction of the liquid crystal molecule. Then, a voltage of 0.5 V was applied to determine the dielectric constant ($\in_{\perp}$) in the minor axis direction of the liquid crystal molecule. The value of dielectric anisotropy was calculated according to the equation $\Delta \in = \in_{\parallel} - \in_{\perp}$.

2) For a composition with a negative dielectric anisotropy: a sample was placed into a liquid crystal cell which was processed into a homeotropic alignment, and a voltage of 0.5 v was applied to determine the dielectric constant ($\in_{\parallel}$). Then, the sample was placed into a liquid crystal cell which was processed into a homogeneous alignment, and a voltage of 0.5 v was applied to determine the dielectric constant ($\in_{\perp}$). The value of dielectric anisotropy was calculated according to the equation $\Delta \in = \in_{\parallel} - \in_{\perp}$.

Threshold voltage (Vth, determined at 25° C., V): when the sample was a compound, the compound was mixed with a suitable composition for determining the threshold voltage. In this case, the threshold voltage value of the compound was an extrapolated value.

1) For a composition with a positive dielectric anisotropy: a sample was placed into an LCD device of a normally white mode with a distance (gap) of $(0.5/\Delta n)$ μm between two glass substrates and a twist angle of 80 degrees, in which $\Delta n$ was the value of optical anisotropy determined by using the method above. A rectangular wave with a frequency of 32 Hz was applied to the device. Then, the voltage of the rectangular wave was increased, and the voltage value at which the transmittance of light through the device reached 90% was determined.

2) For a composition with a negative dielectric anisotropy: a sample was placed into an LCD device of a normally black mode with a distance (gap) of about 9 μm between two glass substrates, which was processed into a homeotropic alignment. A rectangular wave with a frequency of 32 Hz was applied to the device. Then, the voltage of the rectangular wave was increased, and the voltage value at which the transmittance of light through the device reached 10% was determined.

Voltage holding ratio (VHR, determined at 25° C., %): the TN device used for the determination had a polyimide alignment film and a distance (cell gap) of 6 μm between two glass substrates. A sample was placed into the device, which was then sealed with a UV-polymerizable adhesive. Then, the TN device was charged by applying a pulse voltage (5V, 60 ms). The voltage decay was determined by using a high-speed voltmeter at an interval of 16.7 ms, and the area A between the voltage curve and the horizontal axis per unit cycle was calculated. The area B was an area where no decay occurs. The voltage holding ratio was the percentage of the area A relative to the area B.

Helical pitch (determined at 20° C., μm): The helical pitch was measured according to the wedge cell method of Grandjean-Cano. A sample was injected into a wedge cell of Grandjean-Cano, and then the distance (a, in μm) between the disclination lines observed from the wedge cell was measured. The helical pitch (p) could be calculated according to the equation p=2·a·tan θ, in which θ is the angle between the two glass plates in the wedge cell.

Alternatively, the pitch length can be determined by selective reflection (Handbook of Liquid Crystal, p 196, issued in 2000, by Maruzen). For the selective reflection wavelength λ, the relationship <n>p/λ=1 exists, where <n> denotes the average refractive index, and can be calculated with the equation $<n>=\{(n_{\parallel}^2+n_{\perp}^2)/2\}^{1/2}$. The selective reflection wavelength was determined with a microspectrophotometer (trade name MSV-350, manufactured by Japan Electronics Co., Ltd). The pitch was obtained by dividing the resulting reflection wavelength by the average refractive index.

When the concentration of the chiral dopant is low, the pitch of the cholesteric liquid crystal having a reflection wavelength in a region of wavelength longer than that of visible light is proportional to the reciprocal of the concentration. Therefore, multiple points were measured for the pitch length of the liquid crystal having a selective reflection wavelength in the visible light region, and the pitch was calculated by using a linear extrapolation method.

The proportion (percentage) of a component or a liquid crystal compound is weight percentage (wt %) based on the total weight of the liquid crystal compounds. The composition can be prepared by mixing the components including liquid crystal compounds after being weighed. Thus, the wt % of each component can be easily calculated.

Example 1

A liquid crystal composition NLC-1 was prepared by mixing the liquid crystal compounds shown below in the following ratios.

Liquid Crystal Composition K

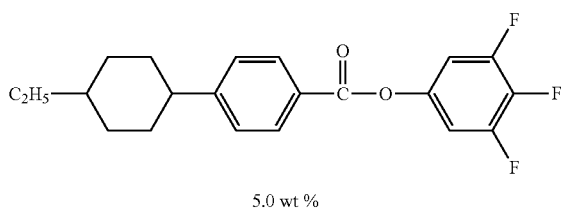

5.0 wt %

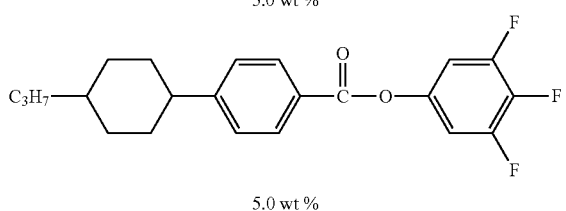

5.0 wt %

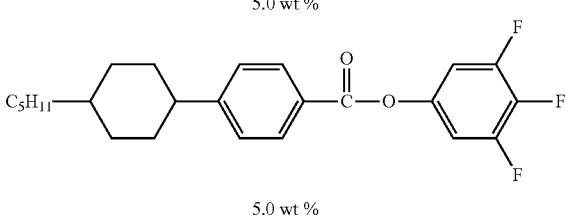

5.0 wt %

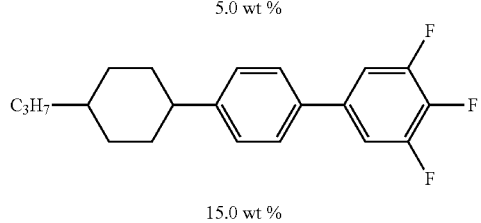

15.0 wt %

-continued

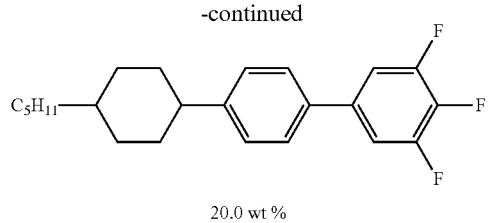

20.0 wt %

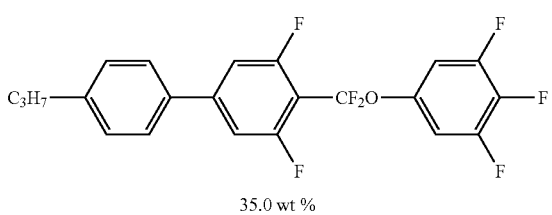

35.0 wt %

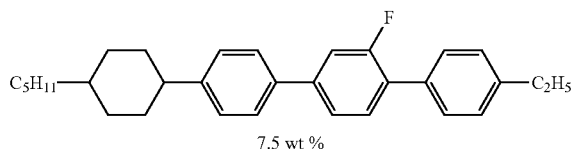

7.5 wt %

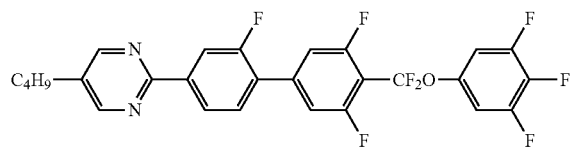

7.5 wt %

A liquid crystal composition NLC-2 was prepared by mixing the liquid crystal composition NLC-1 (80 wt %) with a liquid crystal compound (S1-10) shown below (20 wt %).

Liquid Crystal Compound (S1-10)

Next, a liquid crystal composition CLC-1 containing the liquid crystal composition NLC-2 (95.5 wt %) and a chiral dopant ISO-60BA2 shown below (4.5 wt %) was obtained. The liquid crystal composition CLC-1 has a BP-I point of 75.1° C.

Furthermore, ISO-60BA2 was obtained by esterifying isosorbitol with 4-hexyloxybenzoic acid in the presence of dicyclohexylcarbodiimide (DCC) and 4-dimethylaminopyridine.

ISO-6OBA2

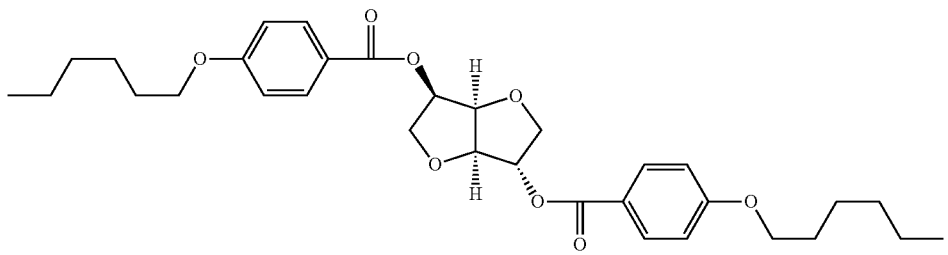

Example 2

Preparation of Mixture of Monomer with Liquid Crystal Composition

As a mixture of a liquid crystal composition and monomers, 79.4 wt % of the liquid crystal composition CLC-1, 10.0 wt % n-dodecyl acrylate, 10.0 wt % 1,4-di(4-(6-(acryloxy)hexyloxy)benzoyloxy)-2-toluene (LCA-6), and 0.6 wt % 2,2'-dimethoxyphenyl acetophenone as photo polymerization initiator were mixed, to prepare a liquid crystal composition CLC-1M.

LCA-6

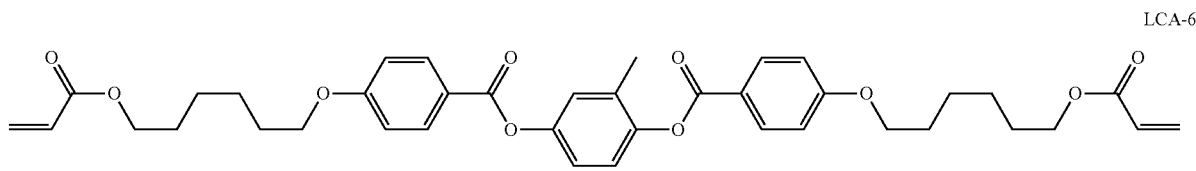 [SMILES: C=CC(=O)OCCCCCCOc1ccc(C(=O)Oc2ccc(OC(=O)c3ccc(OCCCCCCOC(=O)C=C)cc3)c(C)c2)cc1]

Preparation of Polymer/Liquid Crystal Composite Material

The liquid crystal composition CLC-1M was held between a non-aligned comb-like electrode substrate and a glass substrate (without electrode) opposite to the comb-like electrode substrate with a cell thickness of 10 μm, and then the resulting liquid crystal cell was heated to 63.0° C., forming an isotropic phase. In this state, the cell was irradiated with UV light of 365 nm at an intensity of 13 mWcm$^{-2}$ for 1 min for polymerization.

The polymer/liquid crystal composite material CLC-1P thus prepared could maintain an optically isotropic liquid crystal phase even being cooled to room temperature.

Furthermore, as shown in FIG. 1, the electrodes on the comb-like electrode substrate have such a structure that Electrode 1 extending from the left side and Electrode 2 extending from the right side are alternatively arranged. Thus, when a potential difference exists between Electrode 1 and Electrode 2, the comb-like electrode substrate can be provided with an electric field in two directions (upward and downward), as shown in FIG. 1.

Example 3

Figure 2:
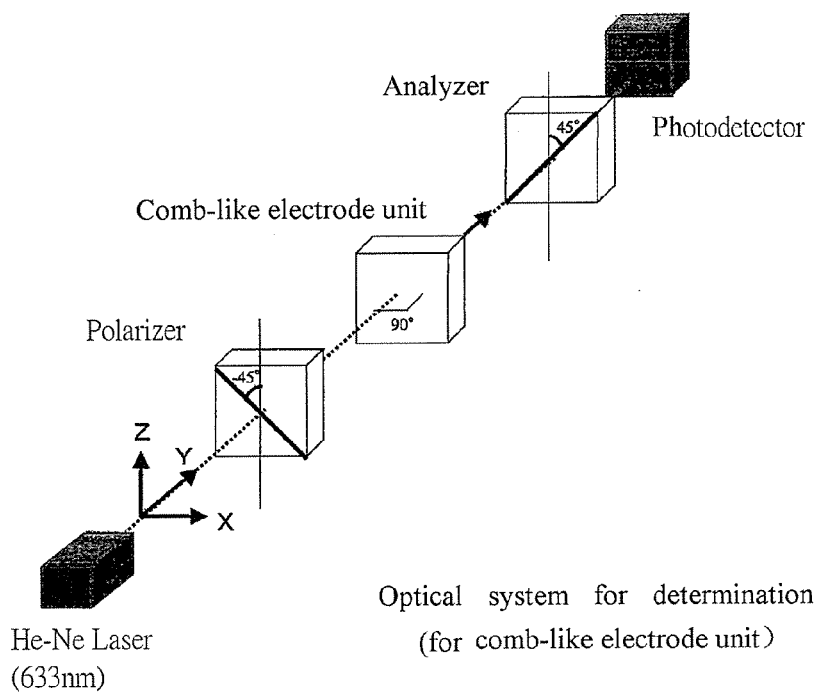
FIG. 2 shows an optical system used in an Example.

A liquid crystal cell holding the polymer/liquid crystal composite material CLC-1P obtained in Example 2 was disposed in the optical system of FIG. 2 to measure the electro-optic properties, as follows. Using the white light source of a polarizing microscope (Optiphot-POL, manufactured by Nikon) as a light source, the incident light from the light source irradiated on the liquid crystal cell was perpendicular to the liquid crystal cell plane, and the line direction of the comb-like electrode was at 45 degrees with respect to the polarizer and the analyzer respectively. The relationship between the applied voltage and the transmittance was investigated by setting the measuring temperature at the clearing point (75° C.)-40° C.=35° C. If a rectangular wave of 86 V was applied, then the transmittance was up to 97%, and the transmitted light intensity was saturated.

INDUSTRIAL APPLICABILITY

The present invention is applicable, for example, in the field of optical devices, such as display devices using a liquid crystal medium.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A liquid crystal composition, comprising a compound of Formula (1) and a chiral dopant, and exhibiting an optically isotropic liquid crystal phase:

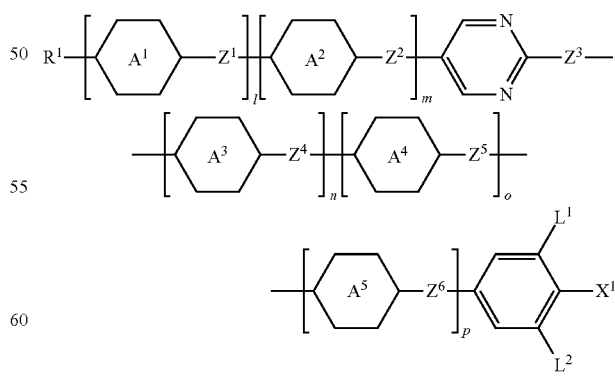

wherein in Formula (1), $R^1$ is hydrogen or a $C_{1-20}$ alkyl, wherein arbitrary —$CH_2$— in the alkyl may be replaced by —O—, —S—, —COO—, —OCO—, —CH=CH—, —CF=CF—, or —C≡C—, and arbitrary hydrogen in the alkyl and the alkyl with arbitrary —CH$_2$— replaced by —O—, —S—, —COO—, —OCO—, —CH=CH—, —CF=CF—, or —C≡C— may be replaced by halogen or a C$_{1-3}$ alkyl; rings A$^1$, A$^2$, A$^3$, A$^4$, and A$^5$ are independently a benzene ring, naphthalene ring, thiophene ring, piperidine ring, cyclohexene ring, bicyclo-octane ring, tetrahydronaphthalene ring, or a cyclohexane ring, where arbitrary hydrogen in the rings may be replaced by halogen, a C$_{1-3}$ alkyl, a C$_{1-3}$ alkoxy, or a C$_{1-3}$ haloalkyl, —CH$_2$— in the rings may be replaced by —O— or —S—, —CH= may be replaced by —N=; Z$^1$, Z$^2$, Z$^3$, Z$^4$, Z$^5$, and Z$^6$ are independently a single bond or a C$_{1-4}$ alkylene, wherein arbitrary —CH$_2$— in the alkylene may be replaced by —O—, —S—, —COO—, —OCO—, —CSO—, —OCS—, —CH=CH—, —CF=CF—, or —C≡C—, and arbitrary hydrogen in the alkylene and the alkylene with arbitrary —CH$_2$— replaced by —O—, —S—, —COO—, —OCO—, —CSO—, —OCS—, —CH=CH—, —CF=CF—, or —C≡C— may be replaced by halogen, provided that at least one of Z$^1$, Z$^2$, Z$^3$, Z$^4$, Z$^5$, and Z$^6$ is —CF$_2$O—; L$^1$ and L$^2$ are independently hydrogen or halogen; X$^1$ is hydrogen, halogen, —C≡N, —N=C=S, —C≡C—C≡N, —SF$_5$, or a C$_{1-10}$ alkyl, wherein arbitrary —CH$_2$— in the alkyl may be replaced by —O—, —S—, —CH=CH—, or —C≡C—, and arbitrary hydrogen in the alkyl and the alkyl with arbitrary —CH$_2$— replaced by —O—, —S—, —CH=CH—, or —C≡C— may be replaced by halogen; and l, m, n, o, and p are independently 0 or 1, and l+m+n+o+p≦4.

2. The liquid crystal composition according to claim 1, wherein in Formula (1), R$^1$ is a C$_{1-20}$ alkyl, a C$_{2-21}$ alkenyl, a C$_{2-21}$ alkynyl, a C$_{1-19}$ alkoxy, a C$_{2-20}$ alkenyloxy, a C$_{1-19}$ alkylthio, a C$_{1-19}$ alkenylthio, or —(CH$_2$)$_v$—CH=CF$_2$, where v is 0 or an integer of 1-19; X$^1$ is hydrogen, halogen, —C≡N, —N=C=S, —SF$_5$, —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$, or —CH=CHCF$_2$CF$_3$.

3. The liquid crystal composition according to claim 1, wherein in Formula (1), Z$^1$, Z$^2$, Z$^3$, Z$^4$, Z$^5$, and Z$^6$ are independently a single bond, —CH$_2$CH$_2$—, —CH=CH—, —C≡C—, —COO—, —CF$_2$O—, —CH$_2$O—, or —OCH$_2$—.

4. The liquid crystal composition according to claim 1, wherein the rings A$^1$, A$^2$, A$^3$, A$^4$, and A$^5$ are independently one of the groups of Formulas (RG-1)-(RG-15), Y$^1$, Y$^2$, Y$^3$, and Y$^4$ are independently hydrogen or halogen, and fn1, fn2, fn3, and fn4 are independently 0, 1, 2, or 3:

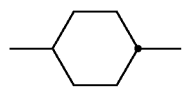 (RG-1)

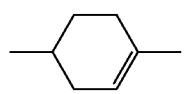 (RG-2)

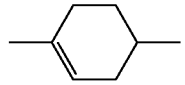 (RG-3)

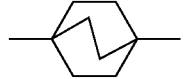 (RG-4)

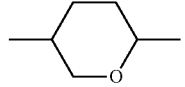 (RG-5)

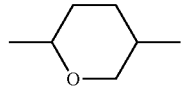 (RG-6)

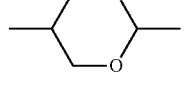 (RG-7)

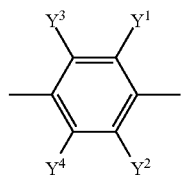 (RG-8)

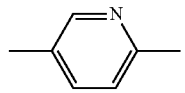 (RG-9)

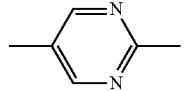 (RG-10)

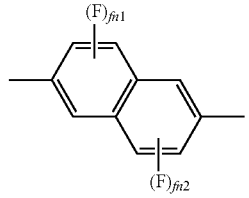 (RG-11)

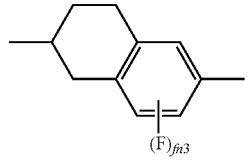 (RG-12)

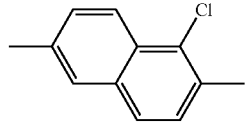 (RG-13)

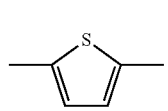 (RG-14)

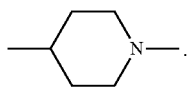
(RG-15)
5. The liquid crystal composition according to claim 1, wherein $R^1$ is any one of the groups of Formulas (CHN-1)-(CHN-19), and $R^{1a}$ is hydrogen or a $C_{1-20}$ alkyl:
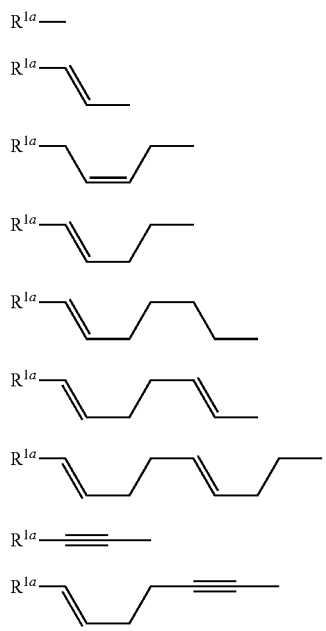
(CHN-1)
(CHN-2)
(CHN-3)
(CHN-4)
(CHN-5)
(CHN-6)
(CHN-7)
(CHN-8)
(CHN-9)
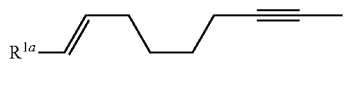 (CHN-10)
 (CHN-11)
 (CHN-12)
 (CHN-13)
 (CHN-14)
 (CHN-15)
 (CHN-16)
 (CHN-17)
 (CHN-18)
 (CHN-19)
6. The liquid crystal composition according to claim 1, comprising at least one compound selected from the group consisting of compounds of Formulas (1-1)-(1-8):
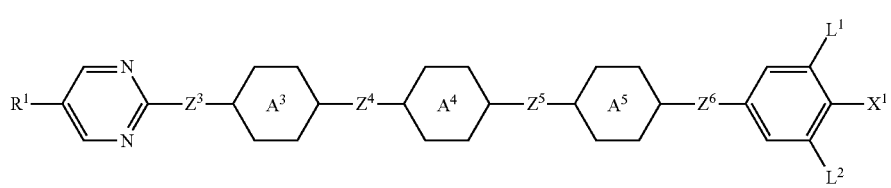
(1-1)
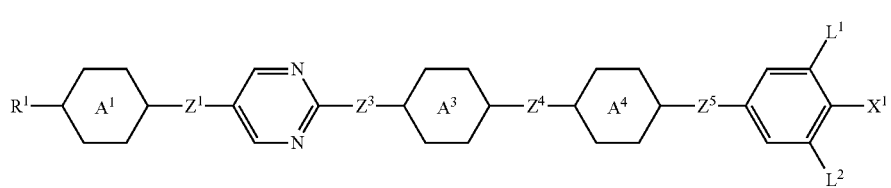
(1-2)
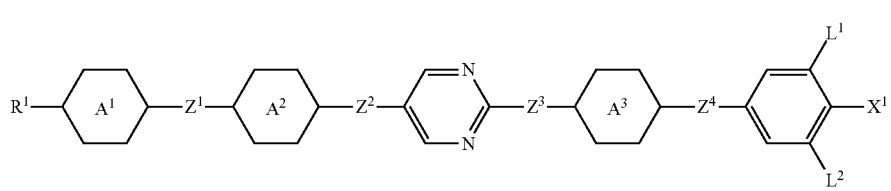
(1-3)

-continued

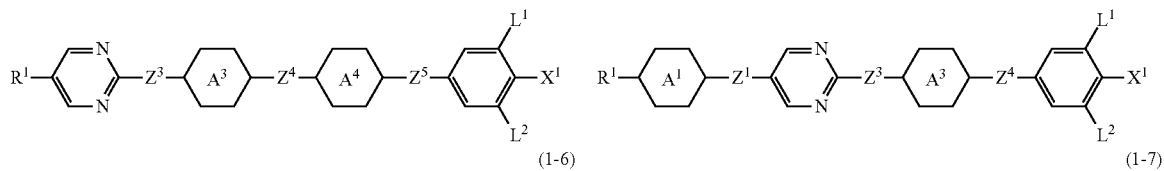

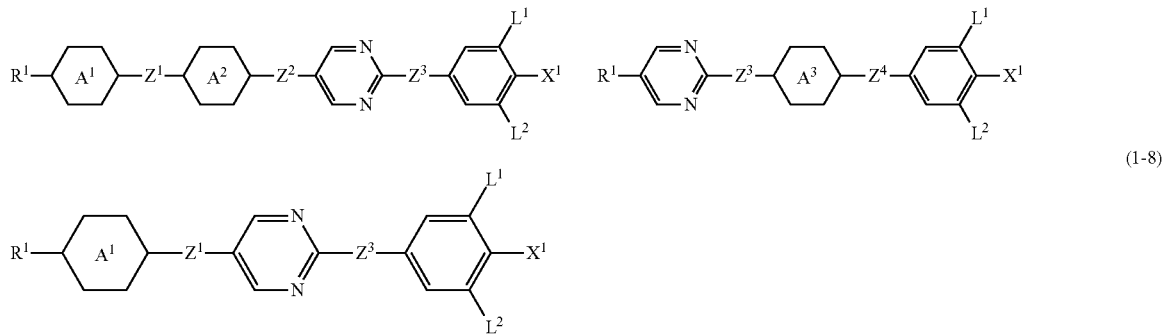

wherein $R^1$ is any one of the groups of Formulas (CHN-1)-(CHN-19), $R^{1a}$ is hydrogen or a $C_{1-20}$ alkyl; rings $A^1$, $A^2$, $A^3$, $A^4$, and $A^5$ are independently a group of Formula (RG-1), (RG-5), (RG-7), (RG-8-1)-(RG-8-5), (RG-9), (RG-10), (RG-11-1), (RG-13), or (RG-15); $Z^1$, $Z^2$, $Z^3$, $Z^4$, $Z^5$, and $Z^6$ are independently a single bond, —$CH_2CH_2$—, —CH=CH—, —C≡C—, —COO—, —$CF_2O$—, —$CH_2O$—, or —$OCH_2$—; $L^1$ and $L^2$ are independently hydrogen, fluorine, or chlorine; $X^1$ is fluorine, chlorine, —C≡N, —$CF_3$, —$CHF_2$, —$CH_2F$, —$OCF_3$, —$OCHF_2$, —$OCH_2F$, or —C≡C—$CF_3$:

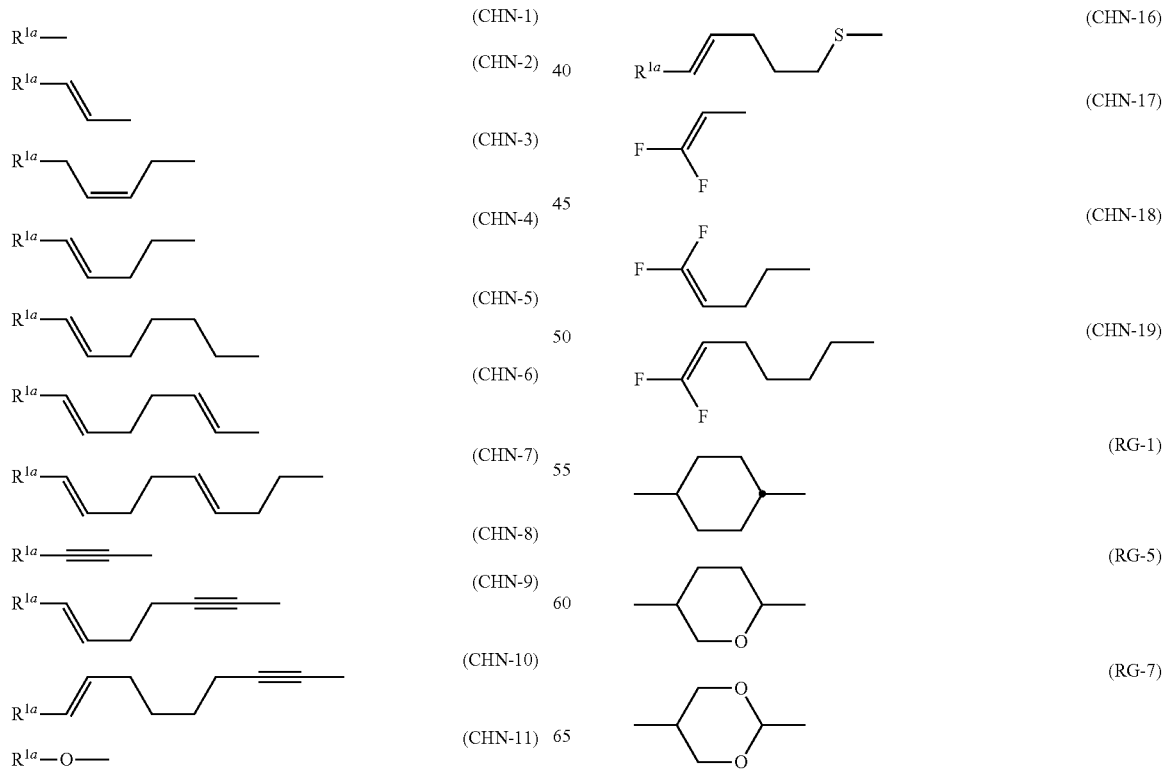

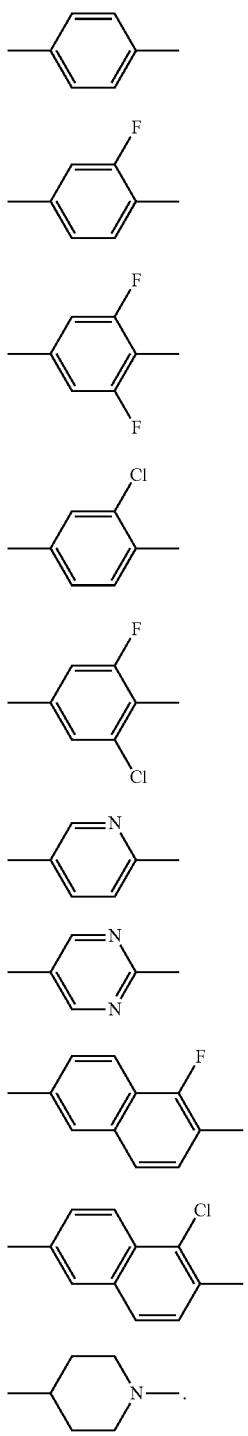

(RG-8-1)
(RG-8-2)
(RG-8-3)
(RG-8-4)
(RG-8-5)
(RG-9)
(RG-10)
(RG-11-1)
(RG-13)
(RG-15)

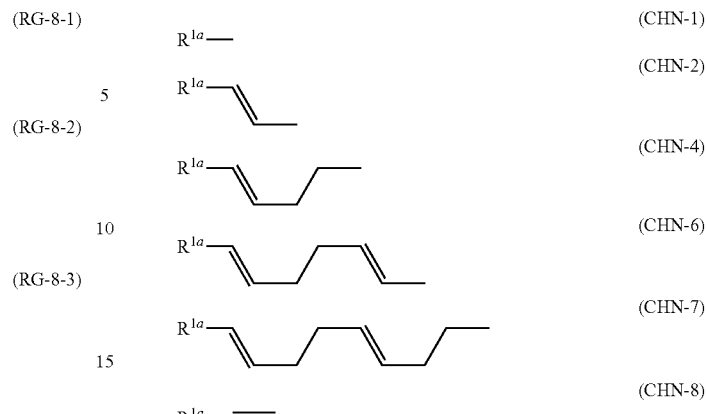

(CHN-1)
(CHN-2)
(CHN-4)
(CHN-6)
(CHN-7)
(CHN-8)

10. The liquid crystal composition according to claim 1, further comprising at least one compound selected from the group consisting of compounds of Formulas (2), (3), and (4):

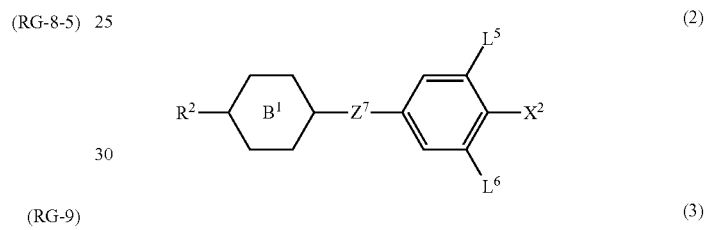

(2)

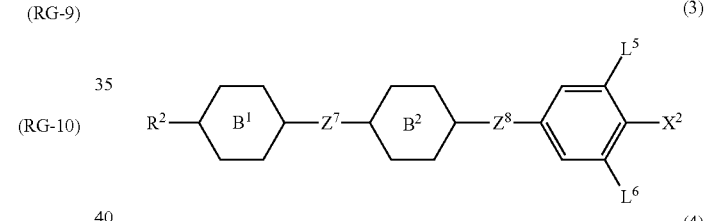

(3)

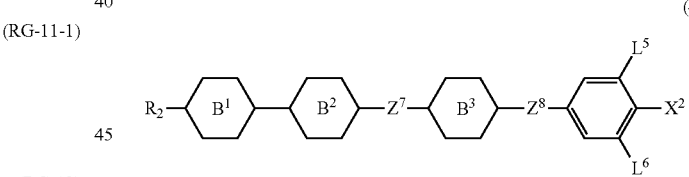

(4)

wherein $R^2$ is a $C_{1-10}$ alkyl or a $C_{2-10}$ alkenyl, wherein arbitrary —$CH_2$— in the alkyl and the alkenyl may be replaced by —O—, and arbitrary hydrogen in the alkyl, the alkenyl, or the alkyl and the alkenyl with arbitrary —$CH_2$— replaced by —O— may be replaced by fluorine; $X^2$ is fluorine, chlorine, —$OCF_3$, —$OCHF_2$, —$CF_3$, —$CHF_2$, —$CH_2F$, —$OCF_2CHF_2$, or —$OCF_2CHFCF_3$; rings $B^1$, $B^2$, and $B^3$ are independently 1,4-cyclohexylene, 1,3-dioxane-2,5-diyl, pyrimidine-2,5-diyl, tetrahydropyrane-2,5-diyl, 1,4-phenylene, naphthalene-2,6-diyl, 1,4-phenylene with arbitrary hydrogen replaced by fluorine, or naphthalene-2,6-diyl with arbitrary hydrogen replaced by fluorine or chlorine; $Z^7$ and $Z^8$ are independently —$(CH_2)_2$—, —$(CH_2)_4$—, —COO—, —$CF_2O$—, —$OCF_2$—, —CH=CH—, —C≡C—, —$CH_2O$—, or a single bond, wherein when at least one of the rings $B^1$-$B^3$ is pyrimidine-2,5-diyl, each of $Z^7$ and $Z^8$ is not —$CF_2O$—; and $L^5$ and $L^6$ are independently hydrogen or fluorine.

7. The liquid crystal composition according to claim 6, wherein in Formulas (1-1)-(1-8), $Z^3$ is a single bond.

8. The liquid crystal composition according to claim 7, wherein in Formulas (1-1)-(1-8), at least one of $Z^1$, $Z^2$, $Z^4$, $Z^5$, and $Z^6$ is —$CF_2O$—, and the others are a single bond.

9. The liquid crystal composition according to claim 6, wherein in Formulas (1-1)-(1-8), $R^1$ is any one of the groups of Formulas (CHN-1), (CHN-2), (CHN-4), and (CHN-6)-(CHN-8), and $R^{1a}$ is hydrogen or a $C_{1-20}$ alkyl:

11. The liquid crystal composition according to claim 1, further comprising at least one compound selected from the group consisting of compounds of Formula (5):

(5)

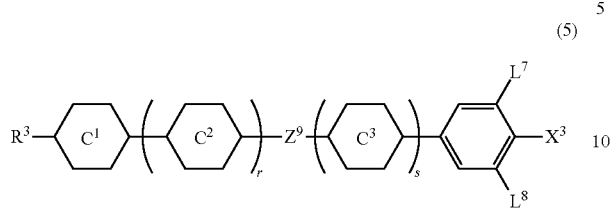

wherein $R^3$ is a $C_{1-10}$ alkyl or a $C_{2-10}$ alkenyl, wherein arbitrary —$CH_2$— in the alkyl and the alkenyl may be replaced by —O—, and arbitrary hydrogen in the alkyl, the alkenyl, or the alkyl and the alkenyl with arbitrary —$CH_2$— replaced by —O— may be replaced by fluorine; $X^3$ is —C≡N or —C≡C—C≡N; rings $C^1$, $C^2$ and $C^3$ are independently 1,4-cyclohexylene, 1,4-phenylene, 1,4-phenylene with arbitrary hydrogen replaced by fluorine, naphthalene-2,6-diyl, naphthalene-2,6-diyl with arbitrary hydrogen replaced by fluorine or chlorine, 1,3-dioxane-2,5-diyl, tetrahydropyrane-2,5-diyl, or pyrimidine-2,5-diyl; $Z^9$ is —$(CH_2)_2$—, —COO—, —$CF_2O$—, —$OCF_2$—, —C≡C—, —$CH_2O$—, or a single bond, wherein when at least one of the rings $C^1$-$C^3$ is pyrimidine-2,5-diyl, $Z^9$ is not —$CF_2O$—; $L^7$ and $L^8$ are independently hydrogen or fluorine; and r is 1 or 2, s is 0 or 1, and r+s=0, 1, or 2.

12. The liquid crystal composition according to claim 1, further comprising at least one compound selected from the group consisting of compounds of Formulas (6), (7), (8), (9), and (10):

(6)

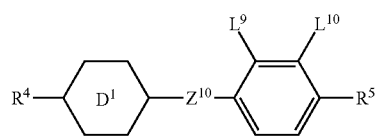

(8)

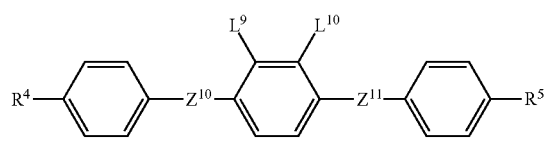

(10)

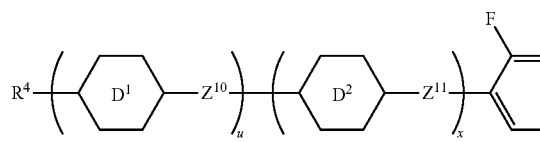

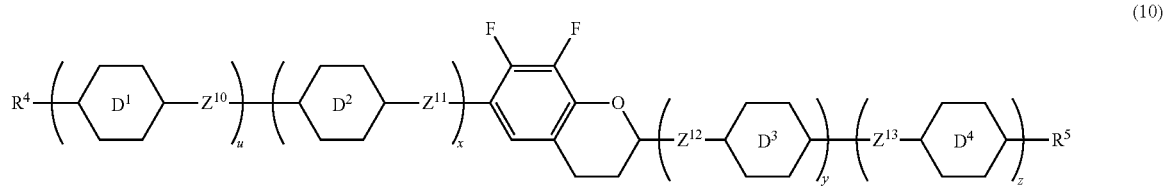

wherein $R^4$ and $R^5$ are independently a $C_{1-10}$ alkyl or a $C_{2-10}$ alkenyl, wherein arbitrary —$CH_2$— in the alkyl and the alkenyl may be replaced by —O—, and arbitrary hydrogen in the alkyl, the alkenyl, or the alkyl and the alkenyl with arbitrary —$CH_2$— replaced by —O— may be replaced by fluorine; rings $D^1$, $D^2$, $D^3$, and $D^4$ are independently 1,4-cyclohexylene, 1,4-cyclohexenylene, 1,4-phenylene, 1,4-phenylene with arbitrary hydrogen replaced by fluorine, tetrahydropyrane-2,5-diyl, or decalin-2,6-diyl; $Z^{10}$, $Z^{11}$, $Z^{12}$, and $Z^{13}$ are independently —$(CH_2)_2$—, —COO—, —$CH_2O$—, —$OCF_2$—, —$OCF_2(CH_2)_2$—, or a single bond; $L^9$ and $L^{10}$ are independently fluorine or chlorine; and t, u, x, y, and z are independently 0 or 1, and u+x+y+z is 1 or 2.

13. The liquid crystal composition according to claim 1, further comprising at least one compound selected from the group consisting of compounds of Formulas (11), (12), and (13):

(11)

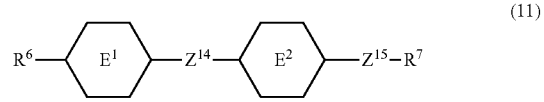

(12)

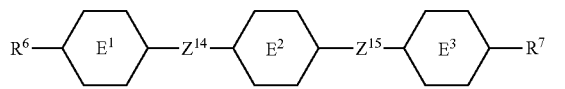

(13)

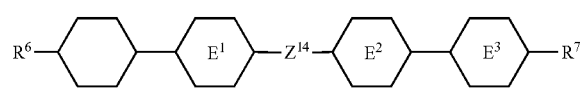

wherein $R^6$ and $R^7$ are independently a $C_{1-10}$ alkyl or a $C_{2-10}$ alkenyl, wherein arbitrary —$CH_2$— in the alkyl and the alkenyl may be replaced by —O—, and arbitrary hydrogen in the alkyl, the alkenyl, or the alkyl and the alkenyl with arbitrary —$CH_2$— replaced by —O— may be replaced by fluorine; rings $E^1$, $E^2$, and $E^3$ are independently 1,4-cyclohexylene, pyrimidine-2,5-diyl, 1,4-phenylene, 2-fluoro-1,4-phenylene, 3-fluoro-1,4-phenylene, or 2,5-difluoro-1,4-phenylene; $Z^{14}$ and $Z^{15}$ are independently —C≡C—, —COO—, —$(CH_2)_2$—, —CH═CH—, or a single bond, wherein when at least one of the rings $E^1$-$E^3$ is pyrimidine-2,5-diyl, each of $Z^{14}$ and $Z^{15}$ is not —$CF_2O$—.

14. The liquid crystal composition according to claim 10, further comprising at least one compound selected from the group consisting of compounds of Formula (5):

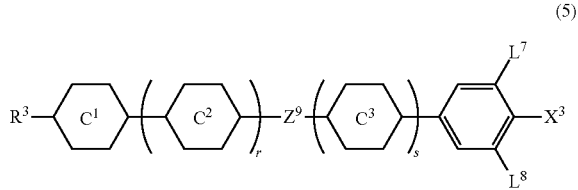
(5)

wherein $R^3$ is a $C_{1\text{-}10}$ alkyl or a $C_{2\text{-}10}$ alkenyl, wherein arbitrary —$CH_2$— in the alkyl and the alkenyl may be replaced by —O—, and arbitrary hydrogen in the alkyl, the alkenyl, or the alkyl and the alkenyl with arbitrary —$CH_2$— replaced by —O— may be replaced by fluorine; $X^3$ is —C≡N or —C≡C—C≡N; rings $C^1$, $C^2$ and $C^3$ are independently 1,4-cyclohexylene, 1,4-phenylene, 1,4-phenylene with arbitrary hydrogen replaced by fluorine, naphthalene-2,6-diyl, naphthalene-2,6-diyl with arbitrary hydrogen replaced by fluorine or chlorine, 1,3-dioxane-2,5-diyl, tetrahydropyrane-2,5-diyl, or pyrimidine-2,5-diyl; $Z^9$ is —$(CH_2)_2$—, —COO—, —$CF_2O$—, —$OCF_2$—, —C≡C—, —$CH_2O$—, or a single bond, wherein when at least one of the rings $C^1$-$C^3$ is pyrimidine-2,5-diyl, $Z^9$ is not —$CF_2O$—; $L^7$ and $L^8$ are independently hydrogen or fluorine; and r is 1 or 2, s is 0 or 1, and r+s=0, 1, or 2.

15. The liquid crystal composition according to claim 10, further comprising at least one compound selected from the group consisting of compounds of Formulas (11), (12), and (13):

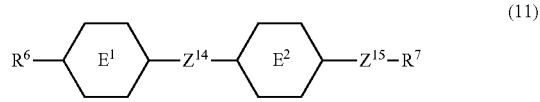
(11)

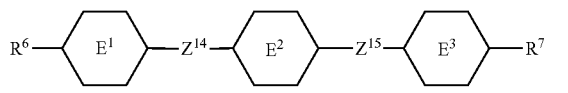
(12)

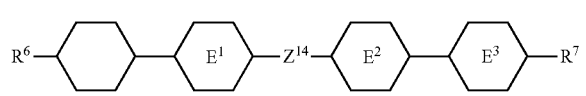
(13)

wherein $R^6$ and $R^7$ are independently a $C_{1\text{-}10}$ alkyl or a $C_{2\text{-}10}$ alkenyl, wherein arbitrary —$CH_2$— in the alkyl and the alkenyl may be replaced by —O—, and arbitrary hydrogen in the alkyl, the alkenyl, or the alkyl and the alkenyl with arbitrary —$CH_2$— replaced by —O— may be replaced by fluorine; rings $E^1$, $E^2$, and $E^3$ are independently 1,4-cyclohexylene, pyrimidine-2,5-diyl, 1,4-phenylene, 2-fluoro-1,4-phenylene, 3-fluoro-1,4-phenylene, or 2,5-difluoro-1,4-phenylene; $Z^{14}$ and $Z^{15}$ are independently —C≡C—, —COO—, —$(CH_2)_2$—, —CH=CH—, or a single bond, wherein when at least one of the rings $E^1$-$E^3$ is pyrimidine-2,5-diyl, each of $Z^{14}$ and $Z^{15}$ is not —$CF_2O$—.

16. The liquid crystal composition according to claim 11, further comprising at least one compound selected from the group consisting of compounds of Formulas (11), (12), and (13):

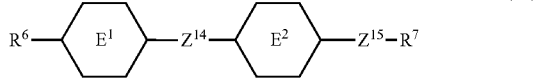
(11)

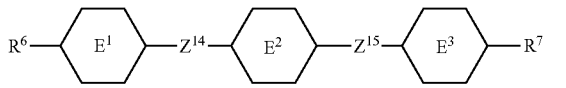
(12)

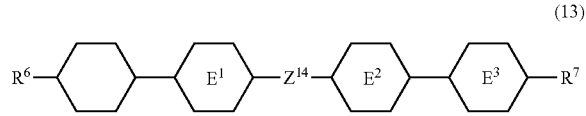
(13)

wherein $R^6$ and $R^7$ are independently a $C_{1\text{-}10}$ alkyl or a $C_{2\text{-}10}$ alkenyl, wherein arbitrary —$CH_2$— in the alkyl and the alkenyl may be replaced by —O—, and arbitrary hydrogen in the alkyl, the alkenyl, or the alkyl and the alkenyl with arbitrary —$CH_2$— replaced by —O— may be replaced by fluorine; rings $E^1$, $E^2$, and $E^3$ are independently 1,4-cyclohexylene, pyrimidine-2,5-diyl, 1,4-phenylene, 2-fluoro-1,4-phenylene, 3-fluoro-1,4-phenylene, or 2,5-difluoro-1,4-phenylene; $Z^{14}$ and $Z^{15}$ are independently —C≡C—, —COO—, —$(CH_2)_2$—, —CH=CH—, or a single bond, wherein when at least one of the rings $E^1$-$E^3$ is pyrimidine-2,5-diyl, each of $Z^{14}$ and $Z^{15}$ is not —$CF_2O$—.

17. The liquid crystal composition according to claim 12, further comprising at least one compound selected from the group consisting of compounds of Formulas (11), (12), and (13):

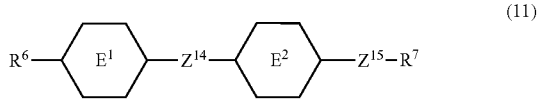
(11)

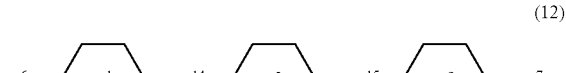
(12)

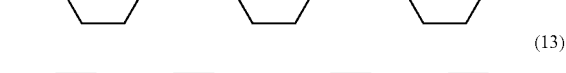
(13)

wherein $R^6$ and $R^7$ are independently a $C_{1\text{-}10}$ alkyl or a $C_{2\text{-}10}$ alkenyl, wherein arbitrary —$CH_2$— in the alkyl and the alkenyl may be replaced by —O—, and arbitrary hydrogen in the alkyl, the alkenyl, or the alkyl and the alkenyl with arbitrary —$CH_2$— replaced by —O— may be replaced by fluorine; rings $E^1$, $E^2$, and $E^3$ are independently 1,4-cyclohexylene, pyrimidine-2,5-diyl, 1,4-phenylene, 2-fluoro-1,4-phenylene, 3-fluoro-1,4-phenylene, or 2,5-difluoro-1,4-phenylene; $Z^{14}$ and $Z^{15}$ are independently —C≡C—, —COO—, —$(CH_2)_2$—, —CH=CH—, or a single bond, wherein when at least one of the rings $E^1$-$E^3$ is pyrimidine-2,5-diyl, each of $Z^{14}$ and $Z^{15}$ is not —$CF_2O$—.

18. The liquid crystal composition according to claim 1, further comprising at least one compound selected from the group consisting of compounds of Formulas (15), (16), (17), and (18):

(15)
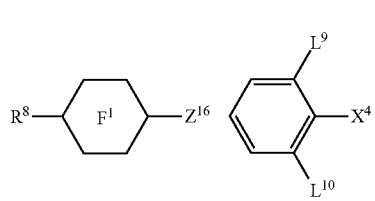

(16)
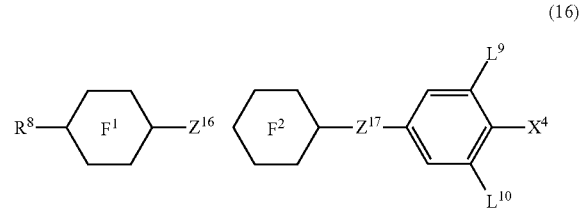

(17)
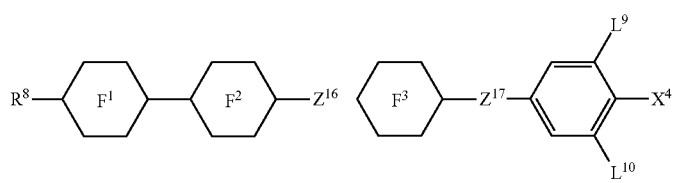

(18)
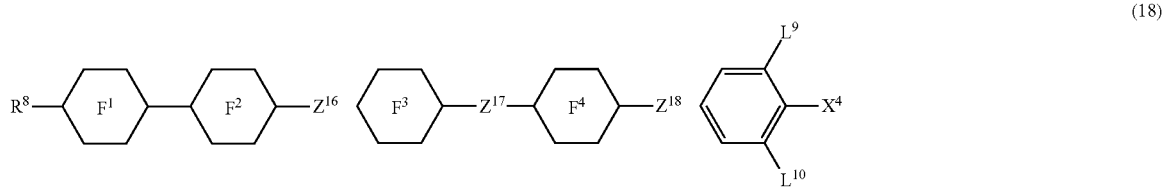

wherein, $R^8$ is a $C_{1-10}$ alkyl, a $C_{2-10}$ alkenyl, or a $C_{2-10}$ alkynyl, wherein arbitrary —$CH_2$— in the alkyl, the alkenyl, and the alkynyl may be replaced by —O—, and arbitrary hydrogen in the alkyl, the alkenyl, the alkynyl, or the alkyl, the alkenyl, and the alkynyl with arbitrary —$CH_2$-replaced by —O— may be replaced by fluorine; $X^4$ is fluorine, chlorine, —$SF_5$, —$OCF_3$, —$OCHF_2$, —$CF_3$, —$CHF_2$, —$CH_2F$, —$OCF_2CHF_2$, or —$OCF_2CHFCF_3$; rings $F^1$, $F^2$, $F^3$, and $F^4$ are independently 1,4-cyclohexylene, 1,3-dioxane-2,5-diyl, pyrimidine-2,5-diyl, tetrahydropyrane-2,5-diyl, 1,4-phenylene, naphthalene-2,6-diyl, 1,4-phenylene with arbitrary hydrogen replaced by fluorine or chlorine, or naphthalene-2,6-diyl with arbitrary hydrogen replaced by fluorine or chlorine; $Z^{16}$, $Z^{17}$, and $Z^{18}$ are independently —$(CH_2)_2$—, —$(CH_2)_4$—, —COO—, —$CF_2O$—, —$OCF_2$—, —CH=CH—, —C≡C—, —$CH_2O$—, or a single bond, wherein when at least one of the rings $F^1$-$F^4$ is pyrimidine-2,5-diyl, each of $Z^{16}$, $Z^{17}$, and $Z^{18}$ is not —$CF_2O$—; and $L^9$ and $L^{10}$ are independently hydrogen or fluorine.

19. The liquid crystal composition according to claim 1, further comprising at least one compound selected from the group consisting of compounds of Formula (19):

(19)
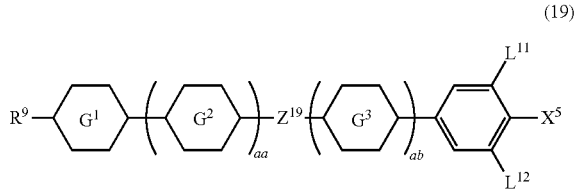

wherein, $R^9$ is a $C_{1-10}$ alkyl, a $C_{2-10}$ alkenyl, or a $C_{2-10}$ alkynyl, wherein arbitrary —$CH_2$— in the alkyl, the alkenyl, and the alkynyl may be replaced by —O—, and arbitrary hydrogen in the alkyl, the alkenyl, the alkynyl, or the alkyl, the alkenyl, and the alkynyl with arbitrary —$CH_2$— replaced by —O— may be replaced by fluorine; $X^5$ is —C≡N, —N=C=S, or —C≡C—C≡N; rings $G^1$, $G^2$, and $G^3$ are independently 1,4-cyclohexylene, 1,4-phenylene, 1,4-phenylene with arbitrary hydrogen replaced by fluorine or chlorine, naphthalene-2,6-diyl, naphthalene-2,6-diyl with arbitrary hydrogen replaced by fluorine or chlorine, 1,3-dioxane-2,5-diyl, tetrahydropyrane-2,5-diyl, or pyrimidine-2,5-diyl; $Z^{19}$ is —$(CH_2)_2$—, —COO—, —$CF_2O$—, —$OCF_2$—, —C≡C—, —$CH_2O$—, or a single bond, wherein when at least one of the rings $G^1$-$G^3$ is pyrimidine-2,5-diyl, $Z^{19}$ is not —$CF_2O$—; $L^{11}$ and $L^{12}$ are independently hydrogen or fluorine; aa is 0, 1, or 2, ab is 0 or 1, aa+ab is 0, 1 or 2.

20. The liquid crystal composition according to claim 1, comprising at least one antioxidant and/or UV absorbent.

21. The liquid crystal composition according to claim 1, wherein the optically isotropic liquid crystal phase does not exhibit two or more colors of diffracted light.

22. The liquid crystal composition according to claim 1, wherein the optically isotropic liquid crystal phase exhibits two or more colors of diffracted light.

23. The liquid crystal composition according to claim 21, obtained by adding the chiral dopant into a composition having a temperature difference between an upper-limit temperature and a lower-limit temperature of 3° C.-150° C. of co-existence of a chiral nematic phase and a non-liquid crystal isotropic phase.

24. The liquid crystal composition according to claim 21, obtained by adding the chiral dopant into a composition having a temperature difference between an upper-limit temperature and a lower-limit temperature of 5° C.-150° C. of co-existence of a chiral nematic phase and a non-liquid crystal isotropic phase.

25. The liquid crystal composition according to claim 21, obtained by adding the chiral dopant into a composition having a temperature difference between an upper-limit temperature and a lower-limit temperature of 3° C.-150° C. of co-existence of a nematic phase and a non-liquid crystal isotropic phase.

26. The liquid crystal composition according to claim 1, wherein a content of the chiral dopant is 1 wt %-40 wt % based on the total weight of the liquid crystal composition.

27. The liquid crystal composition according to claim 1, wherein a content of the chiral dopant is 5 wt %-15 wt % based on the total weight of the liquid crystal composition.

28. The liquid crystal composition according to claim 26, exhibiting a chiral nematic phase at any temperature in the range of 70° C. to −20° C., and having a helical pitch of 700 nm or less within at least a part of the temperature range.

29. The liquid crystal composition according to claim 26, wherein the chiral dopant comprises at least one compound selected from the group of compounds of Formulas (K1)-(K5):

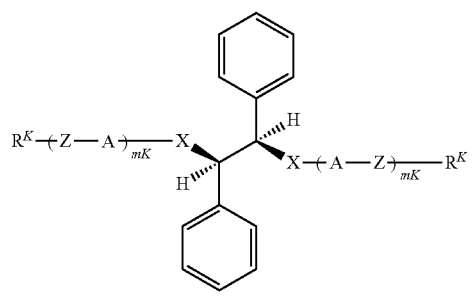
(K1)

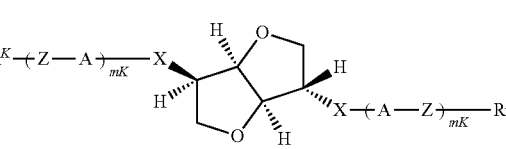
(K2)

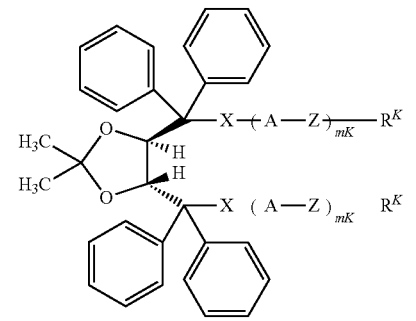
(K3)

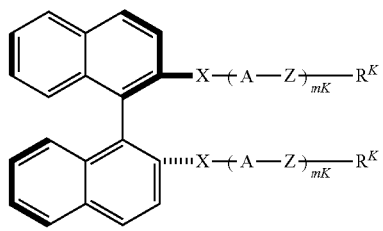
(K4)

(K5)

wherein in Formulas (K1)-(K5), $R^K$ is independently hydrogen, halogen, —C≡N, —N═C═O, —N═C═S, or a $C_{1-20}$ alkyl, wherein arbitrary —$CH_2$— in the alkyl may be replaced by —O—, —S—, —COO—, —OCO—, —CH═CH—, —CF═CF—, or —C≡C—, and arbitrary hydrogen in the alkyl and the alkyl with arbitrary —$CH_2$— replaced by —O—, —S—, —COO—, —OCO—, —CH═CH—, —CF═CF—, or —C≡C— may be replaced by halogen; A is independently an aromatic or non-aromatic 3- to 8-membered ring, or a fused ring having 9 or more carbon atoms, wherein arbitrary hydrogen in the rings may be replaced by halogen, a $C_{1-3}$ alkyl, or a haloalkyl, —$CH_2$— in the rings may be replaced by —O—, —S—, or —NH—, and —CH═ may be replaced by —N═; and Z is independently a single bond or a $C_{1-8}$ alkylene, wherein arbitrary —$CH_2$— may be replaced by —O—, —S—, —COO—, —OCO—, —CSO—, —OCS—, —N═N—, —CH═N—, —N═CH—, —CH═CH—, —CF═CF—, or —C≡C—, and arbitrary hydrogen may be replaced by halogen;

X is independently a single bond, —COO—, —OCO—, —$CH_2O$—, —$OCH_2$—, —$CF_2O$—, —$OCF_2$—, or —$CH_2CH_2$—; and mK is independently an integer of 1-4.

30. The liquid crystal composition according to claim 26, wherein the chiral dopant comprises at least one compound selected from the group consisting of compounds of Formulas (K2-1)-(K2-8) and Formulas (K5-1)-(K5-3):

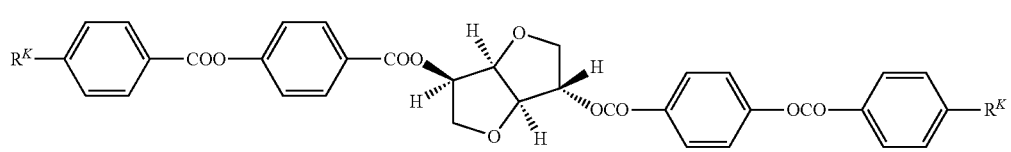
(K2-1)

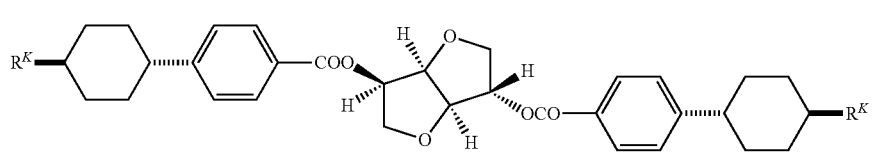
(K2-2)

-continued

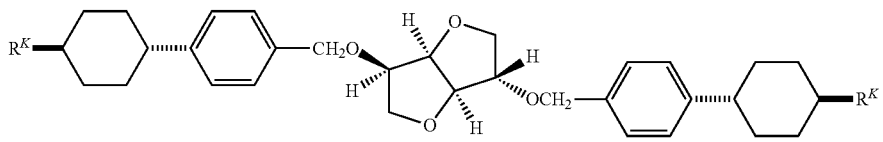 (K2-3)

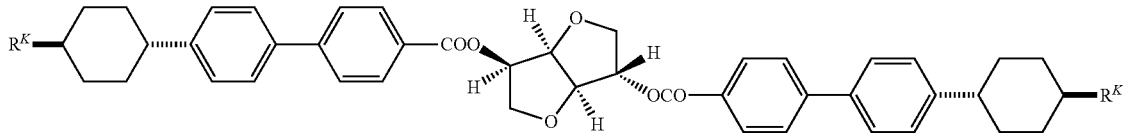 (K2-4)

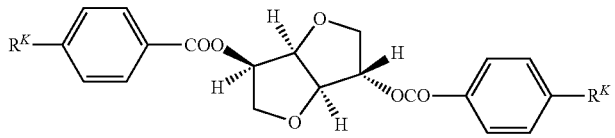 (K2-5)

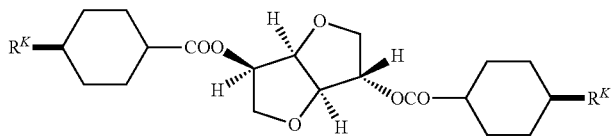 (K2-6)

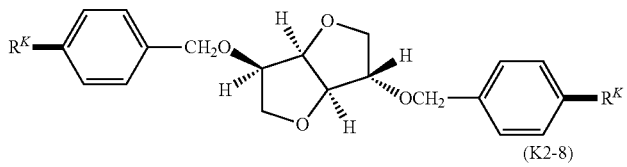 (K2-7)

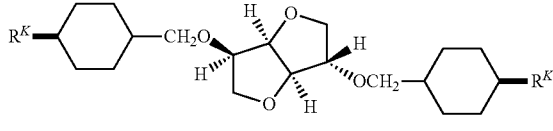 (K2-8)

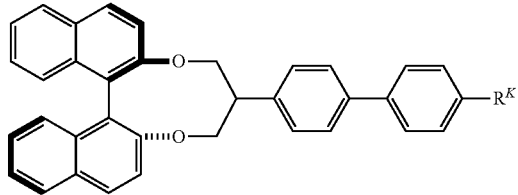 (K5-1)

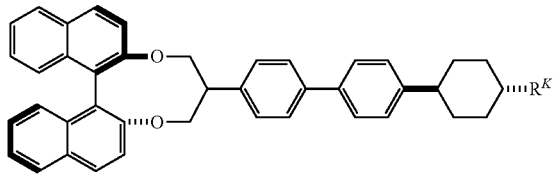 (K5-2)

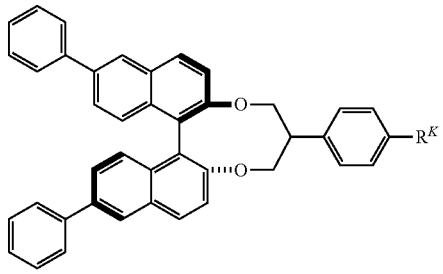 (K5-3)

wherein $R^K$ is independently a $C_{3-10}$ alkyl, wherein —CH$_2$— adjacent to the ring in the alkyl may be replaced by —O—, and arbitrary —CH$_2$— may be replaced by —CH=CH—.

31. A mixture, comprising the liquid crystal composition according to claim 1 and a polymerizable monomer.

32. The mixture according to claim 31, wherein the polymerizable monomer is a photopolymerizable monomer or a thermal-polymerizable monomer.

33. A polymer/liquid crystal composite material, obtained by polymerizing the mixture according to claim 31, for use in a device driven in an optically isotropic liquid crystal phase.

34. A polymer/liquid crystal composite material, obtained by polymerizing the mixture comprising the liquid crystal composition according to claim 1 and a polymerizable monomer in a non-liquid crystal isotropic phase or an optically isotropic liquid crystal phase.

35. The polymer/liquid crystal composite material according to claim 33, wherein the polymer contained in the polymer/liquid crystal composite material has a mesogen moiety.

36. The polymer/liquid crystal composite material according to claim 33, wherein the polymer contained in the polymer/liquid crystal composite material has a cross-linked structure.

37. The polymer/liquid crystal composite material according to claim 33, wherein a content of the liquid crystal composition is 60-99 wt %, and a content of the polymer is 1-40 wt %.

38. An optical device, comprising a liquid crystal medium disposed between substrates having electrodes disposed on either or both surfaces thereof and an electric field-applying means for applying an electric field to the liquid crystal medium via the electrodes, wherein the liquid crystal medium is the liquid crystal composition according to claim 1 wherein a content of the chiral dopant is 1 wt %-40 wt % based on the total weight of the liquid crystal composition or the polymer/liquid crystal composite material obtained by polymerizing the mixture comprising the liquid crystal composition according to claim 1 and a polymerizable monomer.

39. An optical device, comprising a set of substrates having electrodes disposed on either or both surfaces thereof, at least one of which being transparent, a liquid crystal medium disposed between the substrates, a polarizer disposed outside of the substrates, and an electric field-applying means for applying an electric field to the liquid crystal medium via the electrodes, wherein the liquid crystal medium is the liquid crystal composition according to claim 1 wherein a content of the chiral dopant is 1 wt %-40 wt % based on the total weight of the liquid crystal composition or the polymer/liquid crystal composite material obtained by polymerizing the mixture comprising the liquid crystal composition according to claim 1 and a polymerizable monomer.

40. The optical device according to claim 39, wherein on at least one of the set of substrates, the electrodes are constructed in a manner such that an electric field is applied in at least two directions.

41. The optical device according to claim 39, wherein on one or two of the set of substrates disposed in parallel with each other, the electrodes are constructed in a manner such that an electric field is applied in at least two directions.

42. The optical device according to claim 38, wherein the electrodes are disposed in a matrix form to form pixel electrodes, and each pixel is provided with an active element being a thin film transistor (TFT).

* * * * *